(12) United States Patent
Augustine et al.

(10) Patent No.: US 11,583,460 B2
(45) Date of Patent: *Feb. 21, 2023

(54) MEDICAL MODULE INCLUDING AUTOMATED DOSE-RESPONSE RECORD SYSTEM

(71) Applicant: Augustine Biomedical + Design, LLC, Eden Prairie, MN (US)

(72) Inventors: Scott D. Augustine, Deephaven, MN (US); Susan D. Augustine, Deephaven, MN (US); Garrett J. Augustine, Deephaven, MN (US); Brent M. Augustine, Savage, MN (US); Ryan S. Augustine, Minneapolis, MN (US); Randall C. Arnold, Minnetonka, MN (US)

(73) Assignee: Augustine Biomedical + Design, LLC, Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/873,975

(22) Filed: Jul. 26, 2022

(65) Prior Publication Data

US 2022/0362086 A1 Nov. 17, 2022

Related U.S. Application Data

(63) Continuation of application No. 17/245,942, filed on Apr. 30, 2021, now Pat. No. 11,426,318, which is a
(Continued)

(51) Int. Cl.
*A61G 13/10* (2006.01)
*A61B 50/13* (2016.01)
(Continued)

(52) U.S. Cl.
CPC ............ *A61G 13/108* (2013.01); *A61B 50/13* (2016.02); *A61B 50/15* (2016.02); *A61M 16/06* (2013.01);
(Continued)

(58) Field of Classification Search
CPC ..... A61G 13/108; A61M 16/06; A61M 16/18; A61M 16/01; A61B 50/13; A61B 50/15;
(Continued)

(56) References Cited

U.S. PATENT DOCUMENTS

| 4,105,028 A | 8/1978 | Sadlier et al. |
| 4,531,956 A | 7/1985 | Howorth |

(Continued)

FOREIGN PATENT DOCUMENTS

| WO | WO-2019191081 A1 | 10/2019 |
| WO | WO-2021236077 A1 | 11/2021 |

(Continued)

OTHER PUBLICATIONS

"U.S. Appl. No. 15/935,524, Corrected Notice of Allowability dated Jul. 18, 2019", 2 pgs.

(Continued)

*Primary Examiner* — Minh Chau T Pham
(74) *Attorney, Agent, or Firm* — Schwegman, Lundberg & Woessner, P.A.

(57) ABSTRACT

An automated dose-response record system including a module for housing waste-heat producing electronic and electromechanical medical equipment including at least one physiologic monitor, and including a system to measure, temporally correlate and record dose and response events.

30 Claims, 24 Drawing Sheets

Related U.S. Application Data continuation-in-part of application No. 17/167,681, filed on Feb. 4, 2021, now Pat. No. 11,160,710, which is a continuation-in-part of application No. 17/092,681, filed on Nov. 9, 2020, now Pat. No. 10,993,865, which is a continuation of application No. 16/879,406, filed on May 20, 2020, now Pat. No. 10,869,800.

(51) Int. Cl.
| | |
|---|---|
| *A61B 50/15* | (2016.01) |
| *A61B 90/50* | (2016.01) |
| *A61M 16/06* | (2006.01) |
| *A61M 16/18* | (2006.01) |
| *B01D 46/00* | (2022.01) |
| *A61B 46/10* | (2016.01) |
| *A61M 16/01* | (2006.01) |

(52) U.S. Cl.
CPC ............ *A61M 16/18* (2013.01); *A61B 46/10* (2016.02); *A61B 90/50* (2016.02); *A61B 2050/155* (2016.02); *A61M 16/01* (2013.01); *B01D 46/0093* (2013.01)

(58) Field of Classification Search
CPC ... A61B 46/10; A61B 90/50; A61B 2050/155; B01D 46/0093
See application file for complete search history.

(56) References Cited

U.S. PATENT DOCUMENTS

| | | | |
|---|---|---|---|
| 5,399,007 A | 3/1995 | Marconet | |
| 5,409,511 A | 4/1995 | Paul | |
| 5,516,313 A | 5/1996 | Lumpkin | |
| 5,626,140 A | 5/1997 | Feldman | |
| 5,695,536 A | 12/1997 | Fabrizi | |
| 7,494,536 B2 | 2/2009 | Kang et al. | |
| 7,597,731 B2 | 10/2009 | Palmerton et al. | |
| 7,674,436 B1 | 3/2010 | Feldman et al. | |
| 7,753,977 B2 | 7/2010 | Lyons et al. | |
| 9,603,956 B2 | 3/2017 | Newham | |
| 10,312,191 B2 | 6/2019 | Jung et al. | |
| 10,507,153 B2 | 12/2019 | Augustine et al. | |
| 10,512,191 B2 | 12/2019 | Augustine et al. | |
| 10,638,638 B2 | 4/2020 | Augustine et al. | |
| 10,652,577 B2 | 5/2020 | Thoreau et al. | |
| 10,653,577 B2 | 5/2020 | Augustine et al. | |
| 10,702,436 B2 | 7/2020 | Augustine et al. | |
| 10,869,800 B2 * | 12/2020 | Augustine | A61M 16/18 |
| 10,888,482 B2 | 1/2021 | Augustine et al. | |
| 10,993,865 B2 * | 5/2021 | Augustine | A61B 50/15 |
| 10,993,885 B1 | 5/2021 | Fernandez | |
| 11,045,377 B2 | 6/2021 | Augustine et al. | |
| 11,160,710 B1 * | 11/2021 | Augustine | G16H 40/67 |
| 11,173,089 B2 | 11/2021 | Augustine et al. | |
| 11,219,569 B2 | 1/2022 | Augustine et al. | |
| 11,219,570 B2 | 1/2022 | Augustine et al. | |
| 11,285,065 B2 | 3/2022 | Augustine et al. | |
| 11,291,602 B2 | 4/2022 | Augustine et al. | |
| 11,426,318 B2 * | 8/2022 | Augustine | A61B 50/15 |
| 11,426,319 B2 | 8/2022 | Augustine et al. | |
| 11,426,320 B2 | 8/2022 | Augustine et al. | |
| 11,432,982 B2 | 9/2022 | Augustine et al. | |
| 11,432,983 B2 | 9/2022 | Augustine et al. | |
| 11,446,196 B2 | 9/2022 | Augustine et al. | |
| 2001/0035702 A1 | 11/2001 | Murphy et al. | |
| 2002/0120211 A1 | 8/2002 | Wardle et al. | |
| 2003/0033790 A1 | 2/2003 | Hague | |
| 2003/0150328 A1 | 8/2003 | Hansson et al. | |
| 2004/0103789 A1 | 6/2004 | Lan et al. | |
| 2004/0176984 A1 | 9/2004 | White et al. | |
| 2004/0247016 A1 * | 12/2004 | Faries, Jr. | G01K 11/12 374/E11.018 |
| 2004/0249673 A1 | 12/2004 | Smith | |
| 2004/0262146 A1 | 12/2004 | Platt et al. | |
| 2005/0060974 A1 | 3/2005 | Palmerton et al. | |
| 2005/0087256 A1 | 4/2005 | Clark | |
| 2005/0097870 A1 | 5/2005 | Moshenrose | |
| 2006/0042205 A1 | 3/2006 | Kalous et al. | |
| 2007/0199287 A1 | 8/2007 | Wiser | |
| 2007/0225690 A1 | 9/2007 | Sekiguchi et al. | |
| 2008/0097315 A1 | 4/2008 | Miner et al. | |
| 2008/0173178 A1 | 7/2008 | Mette | |
| 2009/0188311 A1 | 7/2009 | Cadieux et al. | |
| 2010/0094262 A1 | 4/2010 | Tripathi et al. | |
| 2010/0324380 A1 | 12/2010 | Perkins et al. | |
| 2011/0030560 A1 | 2/2011 | Bohlen et al. | |
| 2011/0196304 A1 | 8/2011 | Kramer et al. | |
| 2011/0264136 A1 | 10/2011 | Choi et al. | |
| 2011/0317004 A1 | 12/2011 | Tao | |
| 2012/0024154 A1 | 2/2012 | Augustine et al. | |
| 2012/0154120 A1 | 6/2012 | Alloro et al. | |
| 2012/0305787 A1 | 12/2012 | Henson | |
| 2013/0041258 A1 | 2/2013 | Patrick et al. | |
| 2013/0243647 A1 | 9/2013 | Garner et al. | |
| 2014/0081175 A1 | 3/2014 | Telfort | |
| 2014/0262553 A1 | 9/2014 | Pollock et al. | |
| 2015/0168207 A1 | 6/2015 | Pollock et al. | |
| 2015/0224237 A1 | 8/2015 | Reasoner et al. | |
| 2016/0001213 A1 | 1/2016 | Balcik | |
| 2016/0188831 A1 | 6/2016 | Kurtz et al. | |
| 2016/0362234 A1 | 12/2016 | Peret et al. | |
| 2016/0379504 A1 | 12/2016 | Bailey et al. | |
| 2017/0112954 A1 | 4/2017 | Dayton | |
| 2017/0209658 A1 | 7/2017 | Tobia et al. | |
| 2017/0333626 A1 | 11/2017 | Mansour | |
| 2018/0132966 A1 | 5/2018 | Desaulniers et al. | |
| 2019/0105120 A1 | 4/2019 | Norman et al. | |
| 2019/0290524 A1 | 9/2019 | Augustine et al. | |
| 2019/0297745 A1 | 9/2019 | Augustine et al. | |
| 2019/0328598 A1 | 10/2019 | Mangiardi | |
| 2019/0357382 A1 | 11/2019 | Augustine et al. | |
| 2020/0038274 A1 | 2/2020 | Augustine et al. | |
| 2020/0046590 A1 | 2/2020 | Augustine et al. | |
| 2020/0121496 A1 | 4/2020 | Prokop et al. | |
| 2020/0230316 A1 | 7/2020 | Guerra et al. | |
| 2020/0281790 A1 | 9/2020 | Augustine et al. | |
| 2020/0289354 A1 | 9/2020 | Augustine et al. | |
| 2021/0052454 A1 | 2/2021 | Augustine et al. | |
| 2021/0010071 A1 | 4/2021 | Augustine et al. | |
| 2021/0196550 A1 | 7/2021 | Augustine et al. | |
| 2021/0251835 A1 | 8/2021 | Augustine et al. | |
| 2021/0333851 A1 | 11/2021 | Augustine et al. | |
| 2021/0338511 A1 | 11/2021 | Augustine et al. | |
| 2021/0361507 A1 | 11/2021 | Augustine et al. | |
| 2021/0361508 A1 | 11/2021 | Augustine et al. | |
| 2021/0361509 A1 | 11/2021 | Augustine et al. | |
| 2022/0062084 A1 | 3/2022 | Augustine et al. | |
| 2022/0071828 A1 | 3/2022 | Augustine et al. | |
| 2022/0096305 A1 | 3/2022 | Augustine et al. | |
| 2022/0104987 A1 | 4/2022 | Augustine et al. | |
| 2022/0183915 A1 | 6/2022 | Augustine et al. | |
| 2022/0202639 A1 | 6/2022 | Augustine et al. | |
| 2022/0347031 A1 | 11/2022 | Augustine et al. | |
| 2022/0354723 A1 | 11/2022 | Augustine et al. | |
| 2022/0362085 A1 | 11/2022 | Augustine et al. | |
| 2022/0362087 A1 | 11/2022 | Augustine et al. | |
| 2022/0367020 A1 | 11/2022 | Augustine et al. | |
| 2022/0370275 A1 | 11/2022 | Augustine et al. | |

FOREIGN PATENT DOCUMENTS

| | | |
|---|---|---|
| WO | WO-2021236182 A1 | 11/2021 |
| WO | WO-2021236319 A1 | 11/2021 |

OTHER PUBLICATIONS

"U.S. Appl. No. 15/935,524, Corrected Notice of Allowability dated Aug. 21, 2019", 2 pgs.

"U.S. Appl. No. 15/935,524, Non Final Office Action dated Mar. 8, 2019", 8 pgs.

(56) References Cited

OTHER PUBLICATIONS

"U.S. Appl. No. 15/935,524, Non Final Office Action dated Sep. 19, 2018", 8 pgs.
"U.S. Appl. No. 15/935,524, Notice of Allowance dated Jun. 12, 2019", 9 pgs.
"U.S. Appl. No. 15/935,524, Response filed May 15, 2019 to Non Final Office Action dated Mar. 8, 2019", 10 pgs.
"U.S. Appl. No. 15/935,524, Response filed Dec. 12, 2018 to Non Final Office Action dated Sep. 19, 2018", 18 pgs.
"U.S. Appl. No. 16/364,884, Corrected Notice of Allowability dated Aug. 29, 2019", 3 pgs.
"U.S. Appl. No. 16/364,884, Corrected Notice of Allowability dated Nov. 8, 2019", 3 pgs.
"U.S. Appl. No. 16/364,884, Non Final Office Action dated Jul. 3, 2019", 9 pgs.
"U.S. Appl. No. 16/364,884, Notice of Allowance dated Aug. 20, 2019", 10 pgs.
"U.S. Appl. No. 16/364,884, Response filed Jun. 18, 2019 to Restriction Requirement dated May 1, 2019", 9 pgs.
"U.S. Appl. No. 16/364,884, Response filed Jul. 24, 2019 to Non Final Office Action dated Jul. 3, 2019", 9 pgs.
"U.S. Appl. No. 16/364,884, Restriction Requirement dated May 1, 2019", 5 pgs.
"U.S. Appl. No. 16/519,677, Non Final Office Action dated Nov. 13, 2019", 6 pgs.
"U.S. Appl. No. 16/519,677, Response filed Dec. 17, 2019 to Non Final Office Action dated Nov. 13, 2019", 9 pgs.
"U.S. Appl. No. 16/529,283, Corrected Notice of Allowability dated Mar. 6, 2020", 2 pgs.
"U.S. Appl. No. 16/529,283, Non Final Office Action dated Sep. 18, 2019", 8 pgs.
"U.S. Appl. No. 16/529,283, Notice of Allowance dated Jan. 10, 2020", 10 pgs.
"U.S. Appl. No. 16/529,283, Response filed Dec. 13, 2019 to Non Final Office Action dated Sep. 18, 2019", 8 pgs.
"U.S. Appl. No. 16/593,033, Notice of Allowance dated Jan. 14, 2020", 10 pgs.
"U.S. Appl. No. 16/601,924, Non Final Office Action dated Dec. 5, 2019", 6 pgs.
"U.S. Appl. No. 16/601,924, Notice of Allowance dated Mar. 11, 2020", 8 pgs.
"U.S. Appl. No. 16/601,924, Response filed Feb. 26, 2020 to Non Final Office Action dated Dec. 5, 2019", 9 pgs.
"U.S. Appl. No. 16/879,406, Corrected Notice of Allowability dated Oct. 21, 2020", 2 pgs.
"U.S. Appl. No. 16/879,406, Non Final Office Action dated Jun. 9, 2020", 9 pgs.
"U.S. Appl. No. 16/879,406, Notice of Allowance dated Sep. 10, 2020", 8 pgs.
"U.S. Appl. No. 16/879,406, Response filed Sep. 2, 2020 to Non Final Office Action dated Jun. 9, 2020", 12 pgs.
"U.S. Appl. No. 16/885,715, Non Final Office Action dated Jun. 23, 2020", 9 pgs.
"U.S. Appl. No. 16/885,715, Notice of Allowance dated Sep. 22, 2020", 8 pgs.
"U.S. Appl. No. 16/885,715, Notice of Non-Compliant Amendment dated Sep. 10, 2020", 2 pgs.
"U.S. Appl. No. 16/885,715, Response filed Sep. 2, 2020 to Non Final Office Action dated Jun. 23, 2020", 12 pgs.
"U.S. Appl. No. 16/885,715, Response filed Sep. 14, 2020 to Notice of Non-Compliant Amendment dated Sep. 10, 2020", 12 pgs.
"U.S. Appl. No. 17/092,681, Non Final Office Action dated Dec. 17, 2020", 8 pgs.
"U.S. Appl. No. 17/092,681, Notice of Allowance dated Feb. 2, 2021", 9 pgs.
"U.S. Appl. No. 17/092,681, Response filed Jan. 22, 2021 to Non Final Office Action dated Dec. 17, 2020", 13 pgs.
"U.S. Appl. No. 17/103,426, Non Final Office Action dated Jan. 25, 2021", 8 pgs.
"U.S. Appl. No. 17/103,426, Notice of Allowance dated Mar. 12, 2021", 8 pgs.
"U.S. Appl. No. 17/103,426, Response filed Mar. 2, 2021 to Non Final Office Action dated Jan. 25, 2021", 9 pgs.
"U.S. Appl. No. 17/167,681, Corrected Notice of Allowability dated Sep. 21, 2021", 2 pgs.
"U.S. Appl. No. 17/167,681, Non Final Office Action dated Apr. 5, 2021", 8 pgs.
"U.S. Appl. No. 17/167,681, Notice of Allowance dated May 17, 2021", 9 pgs.
"U.S. Appl. No. 17/167,681, Notice of Allowance dated Aug. 25, 2021", 12 pgs.
"U.S. Appl. No. 17/167,681, Response filed May 5, 2021 to Non Final Office Action dated Apr. 5, 2021", 10 pgs.
"U.S. Appl. No. 17/199,722, Non Final Office Action dated May 12, 2021", 7 pgs.
"U.S. Appl. No. 17/199,722, Notice of Allowance dated Jul. 26, 2021", 9 pgs.
"U.S. Appl. No. 17/199,722, Preliminary Amendment filed Apr. 12, 2021", 12.
"U.S. Appl. No. 17/199,722, Response filed Jul. 14, 2021 to Non Final Office Action dated May 12, 2021", 15 pgs.
"U.S. Appl. No. 17/245,942, Final Office Action dated Mar. 2, 2022", 9 pgs.
"U.S. Appl. No. 17/245,942, Non Final Office Action dated Jun. 30, 2021", 11 pgs.
"U.S. Appl. No. 17/245,942, Non Final Office Action dated Nov. 19, 2021", 13 pgs.
"U.S. Appl. No. 17/245,942, Notice of Allowance dated May 2, 2022", 10 pgs.
"U.S. Appl. No. 17/245,942, Notice of Allowance dated Jul. 27, 2021", 9 pgs.
"U.S. Appl. No. 17/245,942, Response filed Feb. 15, 2022 to Non Final Office Action dated Nov. 19, 2021", 14 pgs.
"U.S. Appl. No. 17/245,942, Response filed Apr. 15, 2022 to Final Office Action dated Mar. 2, 2022", 15 pgs.
"U.S. Appl. No. 17/245,942, Response filed Jul. 14, 2021 to Non Final Office Action dated Jun. 30, 2021", 14 pgs.
"U.S. Appl. No. 17/308,437, Non Final Office Action dated Jul. 15, 2021", 8 pgs.
"U.S. Appl. No. 17/308,437, Notice of Allowance dated Dec. 6, 2021", 9 pgs.
"U.S. Appl. No. 17/308,437, Response filed Nov. 10, 2021 to Non Final Office Action dated Jul. 15, 2021", 11 pgs.
"U.S. Appl. No. 17/332,523, Non Final Office Action dated Jul. 29, 2021", 8 pgs.
"U.S. Appl. No. 17/332,523, Notice of Allowance dated Oct. 29, 2021", 9 pgs.
"U.S. Appl. No. 17/332,523, Response filed Sep. 29, 2021 to Non Final Office Action dated Jul. 29, 2021", 13 pgs.
"U.S. Appl. No. 17/375,546, Non Final Office Action dated Oct. 27, 2021", 8 pgs.
"U.S. Appl. No. 17/375,546, Notice of Allowance dated Feb. 25, 2022", 10 pgs.
"U.S. Appl. No. 17/375,546, Response filed Jan. 27, 2022 to Non Final Office Action dated Oct. 27, 2021", 14 pgs.
"U.S. Appl. No. 17/376,469, Non Final Office Action dated Sep. 17, 2021", 9 pgs.
"U.S. Appl. No. 17/376,469, Notice of Allowance dated Nov. 23, 2021", 9 pgs.
"U.S. Appl. No. 17/376,469, Response filed Sep. 29, 2021 to Non Final Office Action dated Sep. 17, 2021", 11 pgs.
"U.S. Appl. No. 17/523,549, Corrected Notice of Allowability dated Jun. 2, 2022", 2 pgs.
"U.S. Appl. No. 17/523,549, Final Office Action dated Apr. 19, 2022", 8 pgs.
"U.S. Appl. No. 17/523,549, Non Final Office Action dated Jan. 13, 2022", 8 pgs.
"U.S. Appl. No. 17/523,549, Notice of Allowance dated May 3, 2022", 9 pgs.
"U.S. Appl. No. 17/523,549, Response filed Apr. 13, 2022 to Non Final Office Action dated Jan. 13, 2022", 12 pgs.

(56) References Cited

OTHER PUBLICATIONS

"U.S. Appl. No. 17/523,549, Response filed Apr. 19, 2022 to Final Office Action dated Apr. 19, 2022", 12 pgs.
"U.S. Appl. No. 17/528,832, Final Office Action dated Apr. 22, 2022", 10 pgs.
"U.S. Appl. No. 17/528,832, Non Final Office Action dated Feb. 8, 2022", 11 pgs.
"U.S. Appl. No. 17/528,832, Notice of Allowance dated Jun. 29, 2022", 10 pgs.
"U.S. Appl. No. 17/528,832, Response filed Apr. 15, 2022 to Non Final Office Action dated Feb. 8, 2022", 13 pgs.
"U.S. Appl. No. 17/528,832, Response filed Jun. 20, 2022 to Final Office Action dated Apr. 22, 2022", 13 pgs.
"U.S. Appl. No. 17/550,611, Corrected Notice of Allowability dated May 4, 2022", 2 pgs.
"U.S. Appl. No. 17/550,611, Corrected Notice of Allowability dated Jul. 15, 2022", 2 pgs.
"U.S. Appl. No. 17/550,611, Non Final Office Action dated Feb. 10, 2022", 8 pgs.
"U.S. Appl. No. 17/550,611, Notice of Allowance dated Apr. 25, 2022", 9 pgs.
"U.S. Appl. No. 17/550,611, Response filed Apr. 15, 2022 to Non Final Office Action dated Feb. 10, 2022", 13 pgs.
"U.S. Appl. No. 17/550,696, Non Final Office Action dated Feb. 10, 2022", 8 pgs.
"U.S. Appl. No. 17/550,696, Notice of Allowance dated May 17, 2022", 10 pgs.
"U.S. Appl. No. 17/550,696, Response filed May 9, 2022 to Non Final Office Action dated Feb. 10, 2022", 12 pgs.
"U.S. Appl. No. 17/678,550, Final Office Action dated Jun. 3, 2022", 7 pgs.
"U.S. Appl. No. 17/678,550, Non Final Office Action dated May 13, 2022", 7 pgs.
"U.S. Appl. No. 17/678,550, Preliminary Amendment filed Apr. 7, 2022", 11 pgs.
"U.S. Appl. No. 17/678,550, Response filed May 23, 2022 to Non Final Office Action dated May 13, 2022", 14 pgs.
"U.S. Appl. No. 17/697,398, Non Final Office Action dated May 27, 2022", 7 pgs.
"International Application Serial No. PCT/US2019/024054, International Preliminary Report on Patentability dated Oct. 8, 2020", 9 pgs.
"International Application Serial No. PCT/US2019/024054, International Search Report dated Jul. 25, 2019", 5 pgs.
"International Application Serial No. PCT/US2019/024054, Invitation to Pay Additional Fees dated May 29, 2019", 3 pgs.
"International Application Serial No. PCT/US2019/024054, Written Opinion dated Jul. 25, 2019", 7 pgs.
"International Application Serial No. PCT/US2020/033804, International Search Report dated Aug. 28, 2020", 3 pgs.
"International Application Serial No. PCT/US2020/033804, Written Opinion dated Aug. 28, 2020", 10 pgs.
"International Application Serial No. PCT/US2021/016585, International Search Report dated Jun. 30, 2021", 5 pgs.
"International Application Serial No. PCT/US2021/016585, Invitation to Pay Additional Fees dated Apr. 22, 2021", 3 pgs.
"International Application Serial No. PCT/US2021/016585, Written Opinion dated Jun. 30, 2021", 13 pgs.
"International Application Serial No. PCT/US2021/030182, International Search Report dated Aug. 16, 2021", 2 pgs.
"International Application Serial No. PCT/US2021/030182, Written Opinion dated Aug. 16, 2021", 17 pgs.
"U.S. Appl. No. 17/862,971, Non Final Office Action dated Nov. 15, 2022", 7 pgs.
"U.S. Appl. No. 17/873,857, Non Final Office Action dated Nov. 14, 2022", 7 pgs.
"U.S. Appl. No. 17/873,907, Non Final Office Action dated Nov. 14, 2022", 7 pgs.
"U.S. Appl. No. 17/874,963, Non Final Office Action dated Nov. 14, 2022", 7 pgs.
"U.S. Appl. No. 17/874,998, Non Final Office Action dated Nov. 15, 2022", 7 pgs.
"U.S. Appl. No. 17/875,055, Non Final Office Action dated Nov. 15, 2022", 8 pgs.
"International Application Serial No. PCT/US2020/033804, International Preliminary Report on Patentability dated Dec. 1, 2022", 12 pgs.
"International Application Serial No. PCT/US2021/016585, International Preliminary Report on Patentability dated Dec. 1, 2022", 15 pgs.
"International Application Serial No. PCT/US2021/030182, International Preliminary Report on Patentability dated Dec. 1, 2022", 19 pgs.
"U.S. Appl. No. 17/678,550, Response filed Aug. 1, 2022 to Final Office Action dated Jun. 3, 2022", 14 pgs.
"U.S. Appl. No. 17/697,398, Response filed Aug. 2, 2022 to Non Final Office Action dated May 27, 2022", 12 pgs.
"U.S. Appl. No. 17/678,550, Supplemental Amendment filed Aug. 2, 2022", 13 pgs.
"U.S. Appl. No. 17/245,942, Corrected Notice of Allowability dated Aug. 2, 2022", 2 pgs.
"U.S. Appl. No. 17/550,696, Corrected Notice of Allowability dated Aug. 8, 2022", 3 pgs.
"U.S. Appl. No. 17/678,550, Notice of Allowance dated Aug. 11, 2022", 9 pgs.
"U.S. Appl. No. 17/697,398, Notice of Allowance dated Aug. 19, 2022", 9 pgs.

\* cited by examiner

MEDICAL MODULE INCLUDING AUTOMATED DOSE-RESPONSE RECORD SYSTEM

PRIORITY

This application is a continuation of U.S. patent application Ser. No. 17/245,942, filed Apr. 30, 2021, now U.S. Pat. No. 11,426,318, which is a continuation-in-part of U.S. patent application Ser. No. 17/167,681, filed Feb. 4, 2021, now U.S. Pat. No. 11,160,710, which is a continuation-in-part of U.S. application Ser. No. 17/092,681, filed Nov. 9 2020, now U.S. Pat. No. 10,993,865, which is a continuation of U.S. patent application Ser. No. 16/879,406, filed May 20, 2020, now U.S. Pat. No. 10,869,800. The disclosure of all of these applications are incorporated herein by reference in their entirety.

TECHNICAL FIELD

This document pertains generally, but not by way of limitation, to systems and methods for improving safety in operating rooms. In particular, the systems and methods described herein may include but are not limited to, anesthetic and surgical equipment storage and operational data capture, automated anesthetic and patient monitoring data capture and electronic record input.

BACKGROUND

Anesthesia monitors and equipment as well as surgical equipment have been invented, developed and sporadically introduced into surgical practice over more than a century. This equipment is made by a wide variety of companies who have no incentive to coordinate with one another to create the most efficient operating room. Equipment throughout the operating room has been placed in one location or another, generally without a plan and then decades later, is still sitting in that unplanned location.

Over the past 20 years, there has been a gradual movement to replacing paper anesthetic records with electronic anesthetic records (EAR). However, the identity, dosing and timing of IV and inhaled drug administration, IV fluid administration, oxygen and ventilation gas administration and anesthetic events such as intubation have required manual input to the EAR by way of a computer keyboard and mouse. Blood, fluid and urine outputs have also required manual input to the EAR by way of a computer keyboard and mouse. The surgical equipment scattered around the operating room either does not produce a digital output that could memorialize the equipment's operation to the electronic record, that output is not automatically captured, or the output is not provided in a way that provides meaningful context or correlation.

Carefully observing the patient in various conditions and situations including surgery is a source of medical information. However, in this age of electronic monitoring, patient observation by the healthcare provider is becoming a lost art that is infrequently done and if it is done it may not be entered into the record so the information is lost.

SUMMARY

As a result of the current medical practices described, the majority of the input to the electronic anesthetic and medical records has been the data from the vital signs monitors, recording the patient's "response." The "dose" events (things that are given or done to the patient leading to the "response") are manually entered into the record, resulting in mistakes, omissions and no temporal correlation between the dose and response. The incomplete and inaccurate records make any analysis with artificial intelligence and machine learning software problematic, either for that individual patient or for "big data" analysis of populations of patients.

This document pertains generally to systems and methods for improving safety for patients receiving intravenous (IV) medications and fluids, by avoiding medication or fluid errors and documenting the administration. This document pertains generally, but not by way of limitation, to systems and methods for constructing granular (beat-by-beat) anesthetic, surgical and patient records that include both "dose" events (things that are given or done to the patient) and "response" events (inputs from electronic monitors, measurement devices and machine vision "observations"). The dose and response events are precisely temporally related and recorded in the patient's electronic record and may be pooled with the records of other patients in a database that can be analyzed with artificial intelligence and machine learning software.

Illustrative examples of an automated dose-response record system that systematizes surgical safety for patients and OR personnel. In some examples, this automated dose-response record system is designed to house nearly all of the operating room patient monitors and support equipment. Even dissimilar types of equipment that are normally kept separate from one another. In some examples, this unique automated dose-response record system is specially designed to fit next to and under the arm-board of the surgical table—a location traditionally occupied by an IV pole. For the past 100 years, this location has been a wasted "no-man's land" between the anesthesia and surgical sides of the operating room. In reality, the unique space next to and under the arm-board, is truly the "prime real estate" of the entire operating room: it is immediately adjacent the patient for optimal monitoring while simultaneously maintaining observation of the patient and surgical procedure; equipment controls can be conveniently accessed by both the anesthesia and surgical staff; short cables and hoses are adequate to reach the patient; and it is uniquely accessible from both the anesthesia and surgical sides of the anesthesia screen. The unique space next to and under the arm-board is the only location in the entire operating room where cables, cords and hoses from both the anesthesia side and the sterile surgical field side, do not need to traverse the floor or even touch the floor in order to connect to their respective monitor or patient support equipment truly a remarkable location that has been wasted by conventional systems.

In some examples, an illustrative automated dose-response record system can house both anesthesia related and non-anesthesia related equipment. In some examples, the illustrative relocation module can house a variety of non-proprietary OR equipment such as patient vital sign monitors, electro-surgical generators, anesthesia machines and mechanical ventilators. In some examples, the automated dose-response record system is designed to also house newer proprietary safety equipment such as: air-free electric patient warming, surgical smoke evacuation, waste alcohol and oxygen evacuation, evacuation of the flow-boundary dead-zones that cause disruption of the OR ventilation and the evacuation and processing of waste heat and air discharged from OR equipment. In some examples, this automated dose-response record system may also house dissimilar equipment (e.g., unrelated to anesthesia monitoring) such as:

air mattress controls and air pumps; sequential compression legging controls and air pumps; capacitive coupling electrosurgical grounding; RFID counting and detection of surgical sponges; the waste blood and fluid disposal systems; and "hover" mattress inflators. Any of these devices may be stored in the automated dose-response record system together with (or without) anesthesia equipment.

In some examples, the automated dose-response record system is a specialized and optimally shaped rack for holding and protecting the patient monitors and other electronic and electromechanical surgical equipment, in a unique location. A location that is very different from just setting anesthesia monitors on top of the anesthesia machine and scattering other equipment across the floor of the operating room.

The various pieces of electronic and electromechanical equipment housed within the automated dose-response record system disclosed herein can produce relatively large amounts of waste heat. The bulbous lower section of the module is placed on the floor next to the surgical table and is below table height since it is under the arm-board. Releasing waste heat in this location on the floor next to the surgical table may cause a risk of sterile field contamination from the rising waste heat that may include squames and other contaminants. In some examples, the automated dose-response record system may include a waste heat management system to safely dispose of the waste heat created by the electronic and electromechanical equipment housed within the automated dose-response record system.

It would be difficult or even impossible to manage the uncontained waste heat produced by electronic and electromechanical equipment mounted on a simple open rack because it can escape in any direction. In some examples, the module can include a "cowling" covering substantially the entire outer or inner surface. The cowling not only protects the equipment from accidental fluid damage but also confines the waste heat from the electronic and electromechanical equipment mounted within the module, to the inside of the module and cowling. In some examples, the confined waste heat can then be safely managed.

In some examples, the cowling cover of the automated dose-response record system can form or support a waste heat management system. In some examples, the cowling can be provided on an inner surface of the housing. In some examples, the cowling can be described as an insulation. In some examples, the housing can include other types of insulation from heat and/or water. Any suitable type of insulated housing suitable for use in a surgical field can be provided.

In some examples, the automated dose-response record system of the instant invention may also contain the components of the anesthesia gas machine. So-called "gas machines" are relatively simple assortments of piping, valves, flow meters, vaporizers and a ventilator. These could be located within the automated dose-response record system or attached to the automated dose-response record system for further consolidation of equipment and for improved access to the patient. The close proximity to the patient not only shortens the ventilation tubing but also shortens the sampling tubing for the carbon dioxide monitor. The close proximity of the anesthesia gas machine to the patient also allows continuous observation of the patient while adjusting the gas and anesthetic flows.

In some examples, locating the anesthesia machine in or on the automated dose-response record system allows direct access for and sensors and monitors related to the anesthesia machine, to input data to the electronic anesthetic record being recorded by equipment in the automated dose-response record system.

In some examples, an illustrative automated dose-response record system can house both anesthesia related and non-anesthesia related equipment. In some examples, the illustrative automated dose-response record system can house a variety of non-proprietary OR equipment such as patient vital sign monitors and electro-surgical generators. In some examples, the automated dose-response record system is designed to also house newer proprietary safety equipment such as: air-free electric patient warming, surgical smoke evacuation, waste alcohol and oxygen evacuation, evacuation of the flow-boundary dead-zones that cause disruption of the OR ventilation and the evacuation and processing of waste heat and air discharged from OR equipment. In some examples, this automated dose-response record system may also house dissimilar equipment (e.g., unrelated to anesthesia monitoring) such as: air mattress controls and air pumps; sequential compression legging controls and air pumps; capacitive coupling electrosurgical grounding; RFID counting and detection of surgical sponges; the waste blood and fluid disposal systems; and "hover" mattress inflators. Any of these devices may be stored in the automated dose-response record system together with (or without) anesthesia equipment and be in electrical communication with processing circuitry of the dose-response system.

In some examples, the automated dose-response record system is a specialized and optimally shaped rack for holding and protecting the patient monitors and other electronic and electromechanical surgical equipment, in a unique location. A location that is very different from just setting anesthesia monitors on top of the anesthesia machine and scattering other equipment across the floor of the operating room.

In some examples, the collection canisters for waste fluid and blood may be conveniently mounted on the module. Mounting the canisters on the automated dose-response record system eliminates the need for vacuum tubing to lay on the floor while traversing from the wall outlet to the canister and from the surgical field to the canister. Optical or infrared fluid level sensors 153 may be conveniently mounted in the module, adjacent the canister(s). In some examples, the fluid level monitors may automatically activate or deactivate the vacuum to a given canister, thereby automatically shifting the blood and fluid flow to a new canister as the previous one is filled.

In some examples, the controls and display screens for the surgical equipment housed in the automated dose-response record system may be wirelessly connected to a portable display screen such as an iPad or "smart tablet," for convenient access by the nurse anywhere in the room. This allows the surgical nurse to monitor and control the equipment without walking across the room. This is convenient for the nurse and increases awareness of equipment conditions. Staff moving around the OR kick up contaminates from the floor into the air where they can be carried to the sterile surgical field by waste heat. A portable display screen minimizes surgical staff movement in the OR which has been shown to reduce airborne contamination and surgical site infections.

Doctors and nurses dislike record keeping and the switch to the electronic record has made the act of record keeping more difficult and time consuming. Entering the electronic record into the computer sometime after the event occurred and the case has settled down, is not only distracting from patient care but leads to inaccurate records. Hand entered records also bypass the opportunity for the computer to add to patient safety by checking drug identities, dosages, side effects, allergies and alerting the clinician to potential problems or even physically stopping the drug administration. Manually entered records are not useful for managing drug inventories because a given medication administration is not tied to a specific drug bottle or syringe. Finally, the computer mouse and keyboards have been shown to be contaminated by a wide variety of infective organisms and are virtually impossible to clean. Automatic anesthetic data entry to the EAR would improve patient safety, improve clinician job satisfaction and improve OR inventory management.

In general, doctors and nurses are not interested in replacing themselves and their jobs with automated drug delivery or automated anesthesia systems. However, they may be more open to automated record keeping. The challenge with automated record keeping is automating the data input that documents the numerous activities, anesthesia related events, fluid, gas and medication administration that constitute an anesthetic experience or another medical situation The second challenge in implementing an automated electronic anesthetic record (EAR) or electronic medical record (EMR) is to force as little change in routine as possible onto the anesthesiologist and other clinicians using this system. Anesthesiologists and surgeons are generally tradition-bound and resistant to any changes in their "tried and true" way of doing things. Therefore, a successful automated EAR should interact seamlessly with current anesthesia practices and operating room workflow without causing any disruptions.

In some examples, the automated EAR of this disclosure includes a system for automatically measuring and recording the administration of IV medications and fluids. The system for automatically measuring and recording the administration of IV medications and fluids can include one or more sensors, such as one or more of a barcode reader and an RFID interrogator for accurately identifying a medication or fluid for IV administration.

The system for automatically measuring and recording the administration of IV medications and fluids can also include one or more digital cameras with machine vision software ("machine vision") for accurately measuring the volume of medication administered from a syringe or fluid administered from an IV bag through a drip chamber into an IV tubing. The digital cameras with machine vision software basically duplicate the clinician's vision of an activity, injection of a drug from a syringe for example, without interfering in the normal activity and yet allows automatic recording of the activity in the EAR. The machine vision software can include one or more machine-readable mediums that when implemented on hardware processing circuitry of the system or in electrical communication with the system, can perform the functions described herein.

In some examples, the automated EAR of this disclosure uses machine vision to unobtrusively "observe" the flow rate of the ventilation gas flow meters and inhaled anesthetic vaporizers.

In some examples, the automated EAR of this disclosure captures input data from the blood and fluid collection and urine output collection systems (e.g., 242) of this disclosure.

In some examples, a system for automatically measuring and recording the administration of IV medications and fluids can also include, or can instead include, one or more digital cameras with machine vision software ("machine vision") for accurately measuring the volume of medication administered from a syringe or fluid administered from an IV bag through a drip chamber into an IV tubing. The digital cameras with machine vision software basically duplicate the clinician's vision of an activity, injection of a drug from a syringe for example, without interfering in the normal activity and yet allows automatic recording of the activity in the EMR. The machine vision software can include one or more machine-readable mediums that when implemented on hardware processing circuitry of the system or in electrical communication with the system, can perform the functions described herein.

In some examples, the automatic EMR of the security system for IV medications of this disclosure lets the computer (e.g., a processor and memory for performing instructions) add to patient safety by checking drug identities, dosages, side effects, allergies, the patients' medical history and vital signs and alerting the clinician to potential problems or even physically stopping the drug administration. In some examples, the automatic EMR of this disclosure eliminates medication errors by checking the drug to be injected against the physician's medication orders before the injection can occur. In some examples, the automatic EMR of this disclosure is useful for managing drug inventories because a given medication administration is tied to a specific drug bottle or syringe. Finally, the computer mouse and keyboards have been shown to be contaminated by a wide variety of infective organisms and are virtually impossible to clean. Automatic data entry to the EMR would improve patient safety, improve clinician job satisfaction and improve medication inventory management.

In some examples, the automatic EMR of the security system for IV medications of this disclosure may also automatically record and display many other functions including but not limited to: IV fluid administration, medication infusions, the patient's vital signs, urine output, blood loss, ventilator settings, inspired gases, electrosurgical settings, pneumoperitoneum insufflation settings, RFID surgical sponge counts, surgical information and video, dialysis or other medical procedure information and patient activity.

The art and science of medicine can include giving something to the patient (a medicine for example) or doing something to the patient (mechanical ventilation or surgery for example)—the "dose", and then observing the patient's "response." The problem now seen with electronic records is that the only data that is timely recorded is the "response" data provided by the physiologic monitors. Even that response data is frequently not recorded beat-by-beat but rather intermittently recorded every 5 minutes or 30 minutes or 4 hours for example. All of the "dose" data is entered into the electronic record by hand and therefore is prone to mistakes, omissions and unknown timing. Therefore, with current EMRs, the dose and response data cannot be temporally correlated with any accuracy, vastly reducing the analytical and predictive value of the electronic database and record.

In some examples, the automatic EMR of the security system for IV medications of this disclosure includes systems and methods for constructing granular (beat-by-beat, second-by-second) anesthetic, surgical and patient records that include both "dose" events—the things that are given or done to the patient (inputs from medication injection and fluid monitors, various support equipment and machine vision "observations" for example) and "response" events (inputs from electronic monitors, measurement devices and machine vision "observations" for example). In some examples, the invention of this disclosure automatically enters both dose and response events into the electronic record. In some examples, the invention of this disclosure automatically enters both dose and response events into the electronic record and temporally correlates the dose and response events, such as but not limited to, when they are recorded. In some examples, the automatically entered, temporally correlated dose and response events in the patient's electronic record may be analyzed by artificial intelligence (AI) and/or machine learning (ML) software stored in a memory of a storage device electrically coupled to the processing circuitry of the module for immediate advice, alerts and feedback to the clinician. In some examples, the automatically entered, temporally correlated dose and response events in the patient's electronic record may be pooled with the records of other patients in a database that can be analyzed with artificial intelligence and machine learning software.

Machine Learning (ML) is an application that provides computer systems the ability to perform tasks, without explicitly being programmed, by making inferences based on patterns found in the analysis of data. Machine learning explores the study and construction of algorithms(e.g., tools), that may learn from existing data and make predictions about new data. Such machine-learning algorithms operate by building an ML model from example training data in order to make data-driven predictions or decisions expressed as outputs or assessments. The principles presented herein may be applied using any suitable machine-learning tools.

In some examples, the AI or ML software can compare dose and response events from different periods of time for the same patient to learn and identify the particular patient's responses. In some examples the machine learning software can be trained to identify a patient's responses using training obtained from a one or more patients that may include or not include the patient being monitored. Any suitable AI or ML can be implemented to interpret the data generated by the module. Current methods of obtaining data in medical settings cannot generate, store or aggregate such data for analysis using AI or ML. Thus, the dose-response systems described herein provide a technical solution to a technical problem.

Machine vision cameras and software are very good at measuring distances, movements, sizes, looking for defects, fluid levels, precise colors and many other quality measurements of manufactured products. Machine vision cameras and software can also be "taught" through AI and ML to analyze complex and rapidly evolving scenes, such as those in front of a car driving down the road.

In some examples, the automatic EMR of the security system for IV medications of this disclosure includes novel systems and methods for using machine vision cameras and software to "observe" the patient. If the patient is in surgery, the patient's head may be the focus of the observation. In some examples, during surgery the machine vision cameras and software may be "looking" for dose events including but not limited to mask ventilation or endotracheal intubation. In some examples, during surgery the machine vision cameras and software may be "looking" for response events including but not limited to grimacing or tearing or coughing or changes in skin color.

If the patient is on the ward or in the nursing home or other long-term care facility, the whole patient may be the focus of the observation. In some examples, if the patient is on the ward or in the nursing home or other long-term care facility the machine vision cameras, processing circuitry and software may be configured to "look" for dose events (e.g., sense, detect, monitor) including but not limited to repositioning the patient, suctioning the airway or assisting the patient out of bed or any other nursing procedure. In some examples, if the patient is on the ward or in the nursing home or other long-term care facility (including at home) the machine vision cameras, processing circuitry and software may be configured to "look" for response events (e.g., sense, detect, monitor) including but not limited to restlessness or getting out of bed without assistance or coughing or breathing pattern. In some examples, the system can go beyond traditional physiologic monitors. Even physiologic response information such as pain may be detected by facial expression analysis.

In some examples, vital signs such as heart rate, respiration rate, blood oxygen saturation and temperature can be measured (e.g., sensed, detected, monitored) remotely via camera-based methods. Vital signs can be extracted from the optical detection of blood-induced skin color variations—remote photoplethysmography (rPPG).

In some examples, the automatic EMR of the security system for IV medications may allow remote viewing of the displayed patient information. In some examples, the remotely displayed patient information may be used for remote medical supervision such as an anesthesiologist providing remote supervision to a nurse anesthetist who is administering the anesthetic. In some examples, the remotely displayed patient information may be used for remote medical consultation. In some examples, the remotely displayed patient information may be used to document the involvement of remote medical supervision or consultation for billing purposes.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document. Any combination of the features shown and described in this disclosure, including combinations of fewer or more features is within the content of this disclosure. Modules, systems and methods including individual features described herein, without combinations of features as shown in the examples (for the sake of brevity), are also within the scope of this disclosure.

DETAILED DESCRIPTION

The following detailed description is exemplary in nature and is not intended to limit the scope, applicability, or configuration of the invention in any way. Rather, the following description provides practical illustrations for implementing exemplary examples of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

As described herein, operably coupled can include, but is not limited to, any suitable coupling, such as a fluid (e.g., liquid, gas) coupling, an electrical coupling or a mechanical coupling that enables elements described herein to be coupled to each other and/or to operate together with one another (e.g., function together).

Dose-response involves giving something to the patient (a medicine for example) or doing something to the patient (mechanical ventilation or surgery for example)—the "dose", and then observing the patient's "response."

Throughout this disclosure, the word "dose" or "dose event" means something that was given to or done to the patient. In some examples, "dose events" involve giving something to the patient including but not limited to: the injection or ingestion of medications, the infusion of medications, the infusion of IV fluids, inspired gases such as oxygen or nitrous oxide or volatile anesthetics or nitric oxide.

In some examples, "dose events" are things done to the patient, including but not limited to: mask ventilation, tracheal intubation, mechanical ventilation, pneumoperitoneum insufflation, patient positioning and surgery.

In some examples, "dose events" are applications of electricity to the patient, including but not limited to: train-of-four determination of muscle relaxation, nerve conduction studies, cardiac pacing, cardioversion, electrical stimulation of nerves and electroconvulsive therapy. Many other "dose events" are anticipated.

Throughout this disclosure, the word "response" or "response event" means a physiologic, reflexive motor response or volitional motor response from the patient. In some examples, "response events" involve measuring a physiologic response of the patient measured by the physiologic monitors (e.g., 270 or others), including but not limited to: an electrocardiogram (EKG), pulse oximetry, blood pressure, end tidal gases, electroencephalogram (EEG), bispectral index (BIS), laboratory blood studies, urine output (e.g., 242), blood loss and pulmonary compliance.

Figure 12:
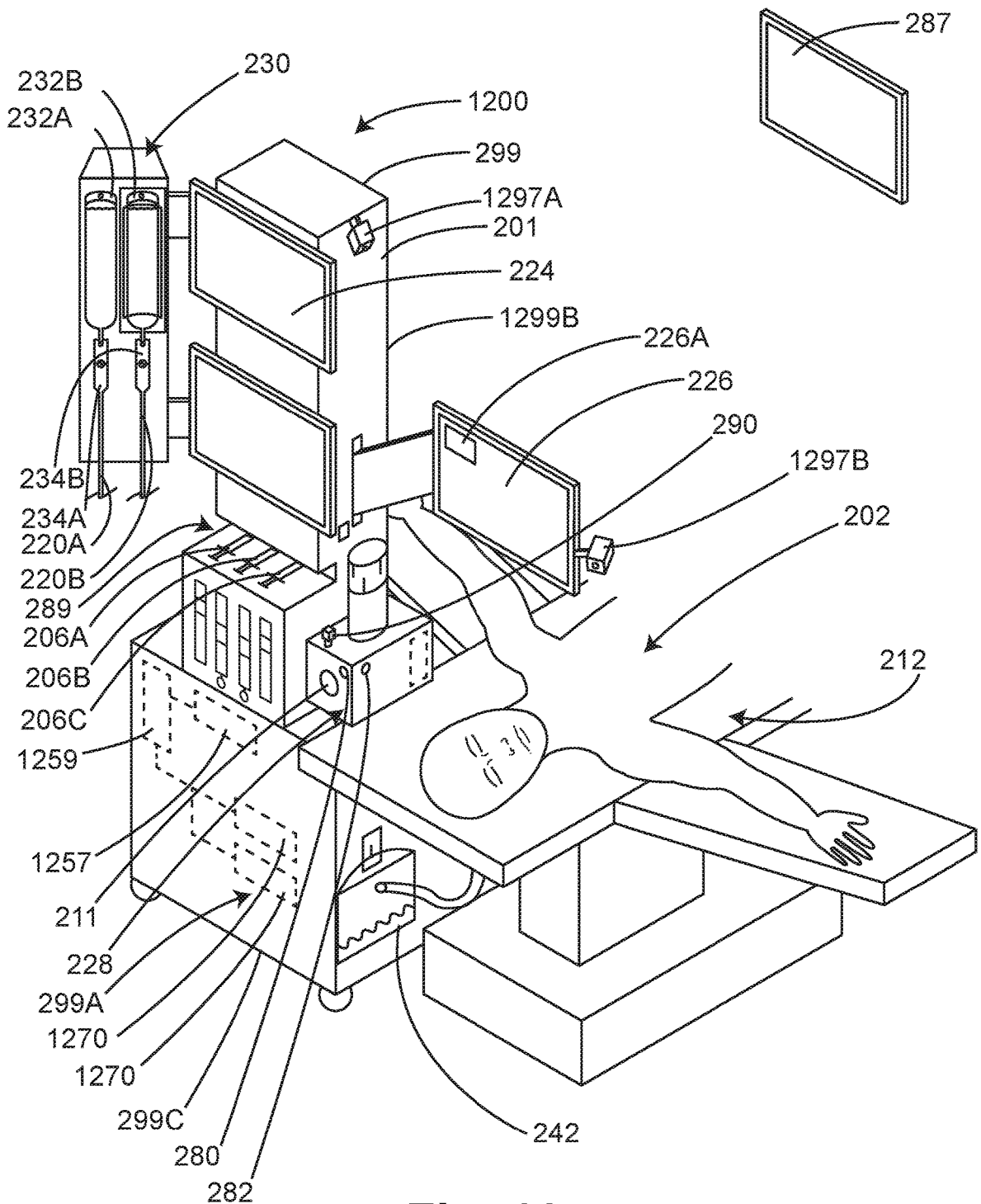
FIG. 12 illustrates an isometric view of another example module including a system for generating an automated electronic anesthetic record located proximate to a patient, in accordance with at least one example of this disclosure.
Figure 13:
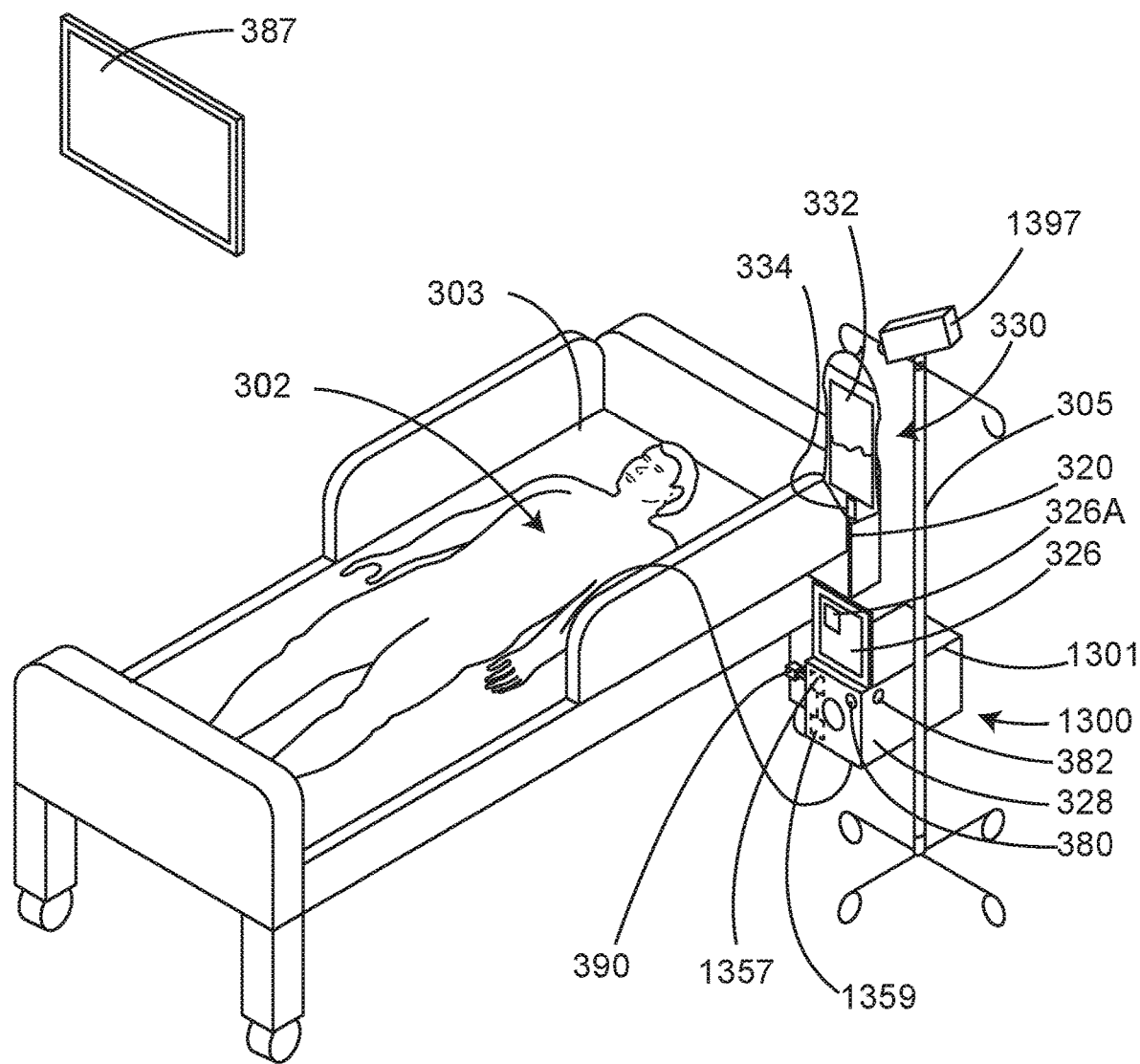
FIG. 13 illustrates an isometric view of another example module including a system for generating an automated electronic anesthetic record located proximate to a patient, in accordance with at least one example of this disclosure.
Figure 15:
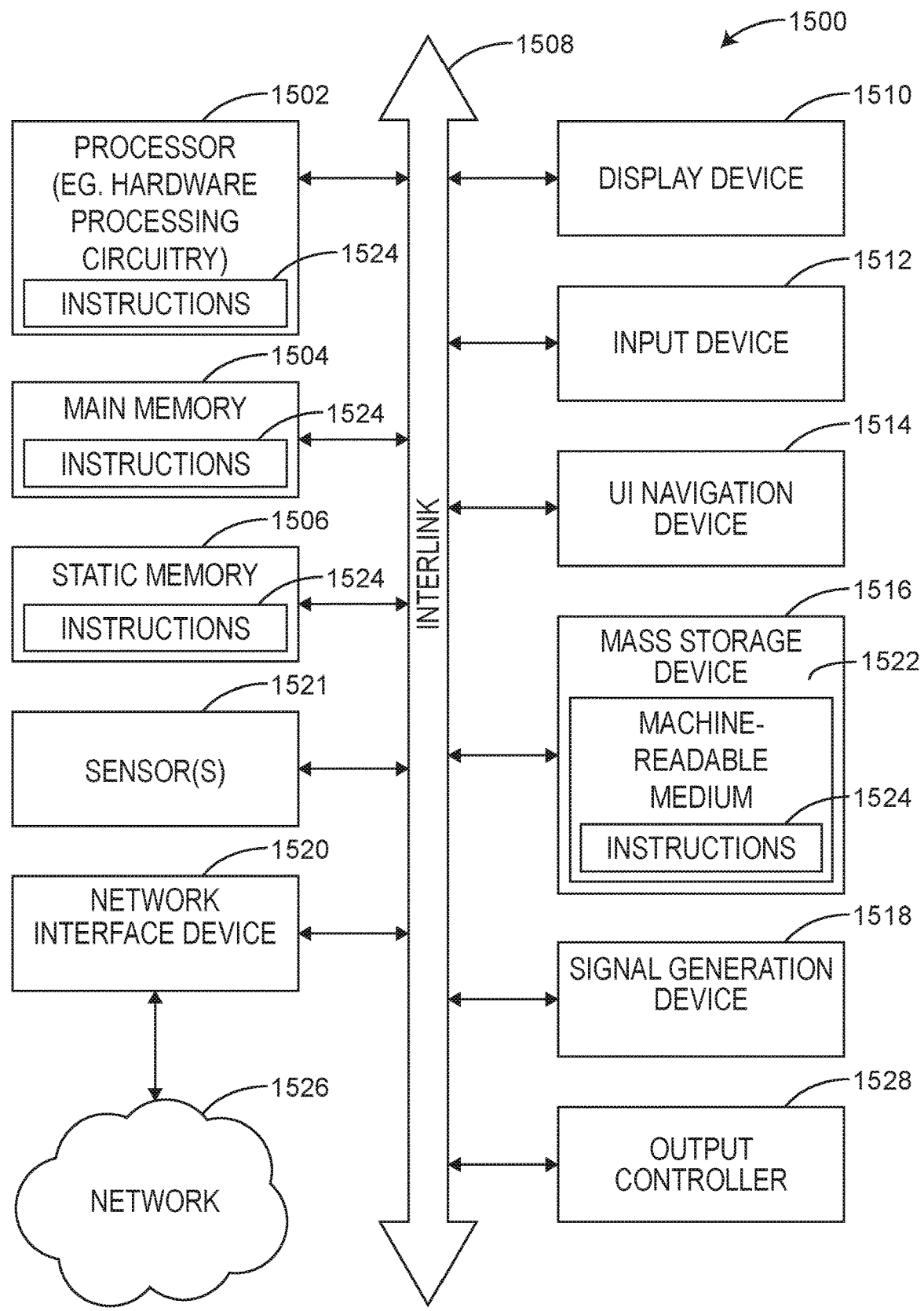
FIG. 15 illustrates generally an example of a block diagram of a machine (e.g., of module 101, 201) upon which any one or more of the techniques (e.g., methodologies) discussed herein may perform in accordance with at least one example of this disclosure.

In some examples, "response events" involve measuring a motor response of the patient, including but not limited to: a train-of-four, grimacing, coughing, movements of many sorts and tearing that may be captured to detect by a machine vision camera in conjunction with software (e.g., 1297A, 1297B, 1397 such as described in at least FIGS. 12, 13 and 15).

Figure 1:
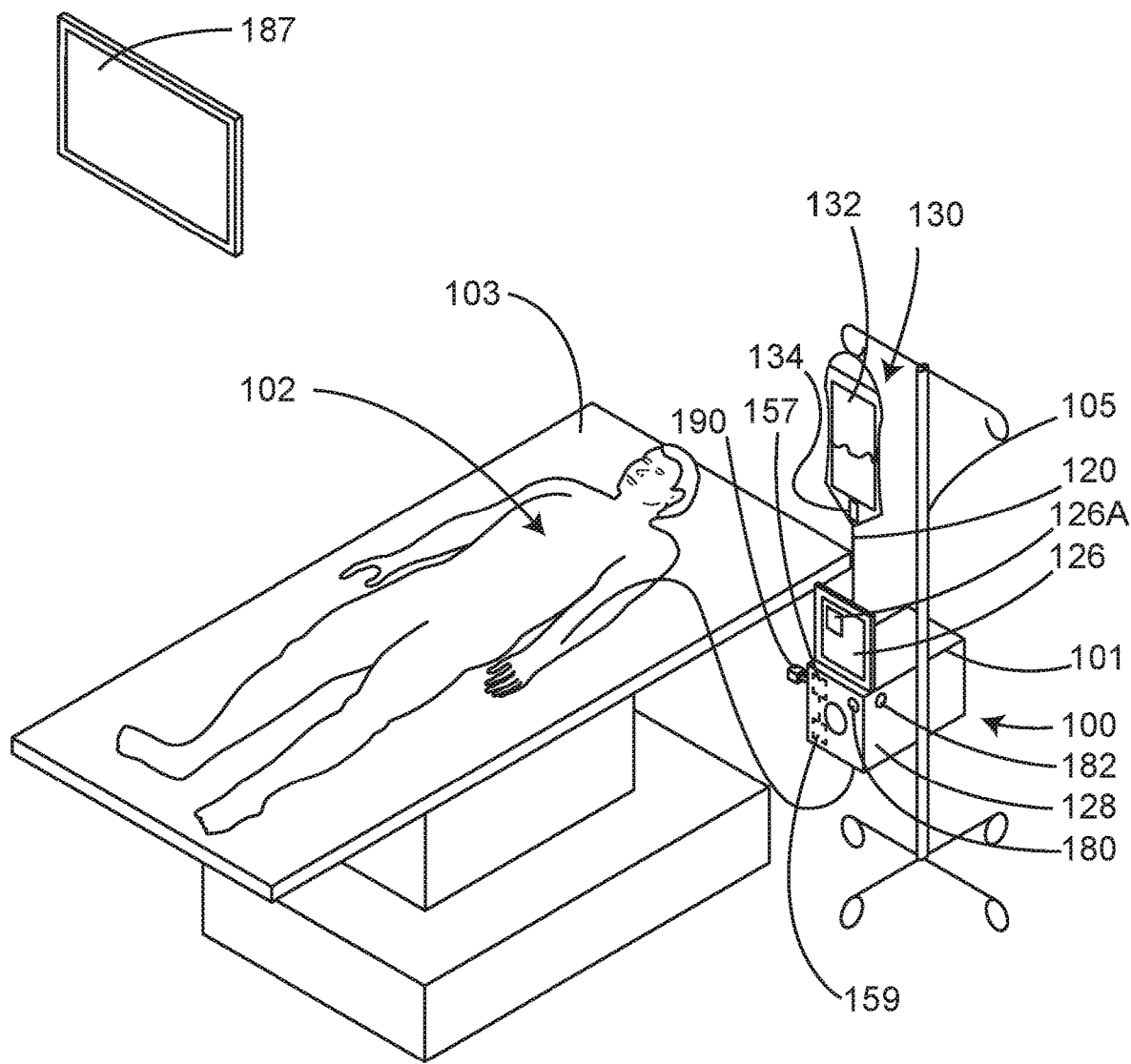
FIG. 1 illustrates an isometric view of an example module including a system for generating an automated electronic anesthetic record located proximate to a patient, in accordance with at least one example of this disclosure.

FIG. 1 illustrates an isometric view of an example automated dose-response record system 100 for generating an automated electronic anesthetic record (EAR) or electronic medical record (EMR) located proximate to a patient. Some aspects of FIG. 1 are also described with respect to the description of other figures, including FIG. 14.

As shown in FIG. 1, the automated dose-response record system 100 may be attached to and portions can be stored within a module 101. The module 101 can conveniently provide direct access to the patient 102. An IV pole 105 may provide a convenient mounting support location for the automated dose-response record system for IV medications 100 (hereinafter, "automated dose-response record system 100"). In some examples, the components and systems of the automated dose-response record system 100 of this disclosure can be supported by other mounting supports, including but not limited to a boom-mounted rack system, a wheeled rack system and a bed 103 mounting bracket. One or more computers including processing circuitry 157, of the automated dose-response record system 100 of this disclosure may be conveniently and safely housed inside the module 101.

In some examples, it is anticipated that some or all of the components of the automated dose-response record system 100 of this disclosure could be used in other healthcare settings such as the intensive care unit, the emergency room or on the ward. As shown in FIG. 1, the module 101 may be mounted on an IV pole 105 or other suitable mounting structure located near the patient 102.

In some examples, a touch-screen electronic record display 126 can convert to a qwerty-type keyboard to allow uncommon anesthetic and surgical events or deviations from pre-recorded scripts, to be manually documented. This allows the standard computer keyboard that is used for data entry in most electronic anesthetic records, to be eliminated. Standard keyboards are known to be contaminated with pathogenic organisms and are nearly impossible to clean and decontaminate due to their irregular surfaces. In contrast, the smooth glass or plastic face of a touch-screen monitor is easy to clean with no crevasses to hide organisms.

In some examples, the automated dose-response record system for IV medications 100 of this disclosure can include a system for automatically measuring and recording the administration of IV medications. In some examples, the system for automatically measuring and recording the administration of IV medications includes a medication identification and measurement system 128. In some examples, aspects of the automated dose-response record system 100 can be provided together with or separately from other aspects of the IV medication identification and measurement system 128 (hereinafter, "medication identification and measurement system 128"). Likewise, aspects of the medication identification and measurement system 128 can be provided together with or separately from other aspects of the automated dose-response record system 100.

Figure 2:
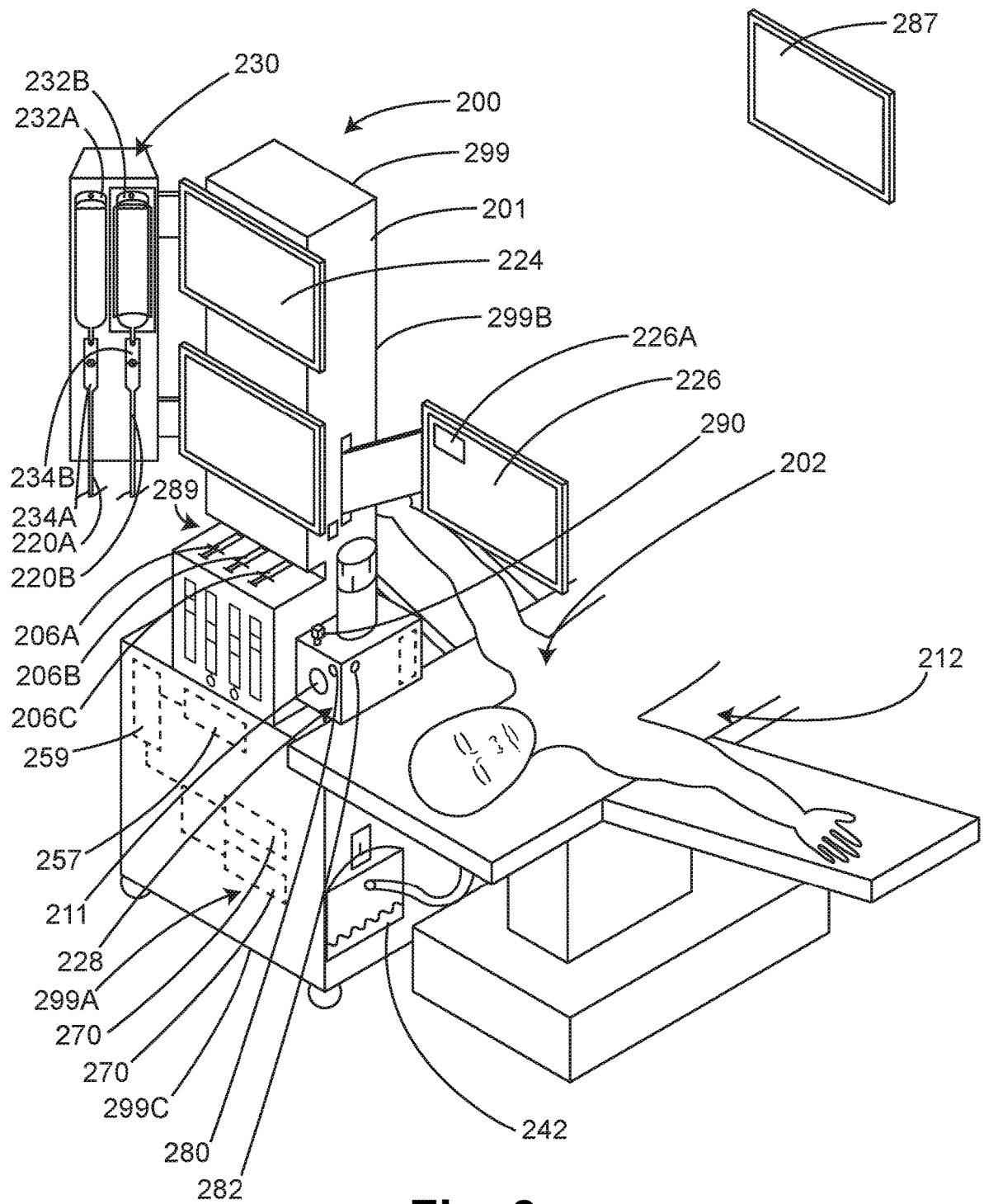
FIG. 2 illustrates an isometric view of an example module including a system for generating an automated electronic anesthetic record located proximate to a patient, in accordance with at least one example of this disclosure.

FIG. 2 illustrates an isometric view of an example automated dose-response record system 200 for generating an automated electronic anesthetic record located proximate to a patient 202. Features of the automated dose-response record system 100 of FIG. 1 may be included in the automated dose-response record system 200 of FIG. 2, and vice-versa, therefore all aspects may not be described in further detail. Like numerals can represent like elements. Aspects of FIGS. 1 and 2 may also be described together.

Figure 14:
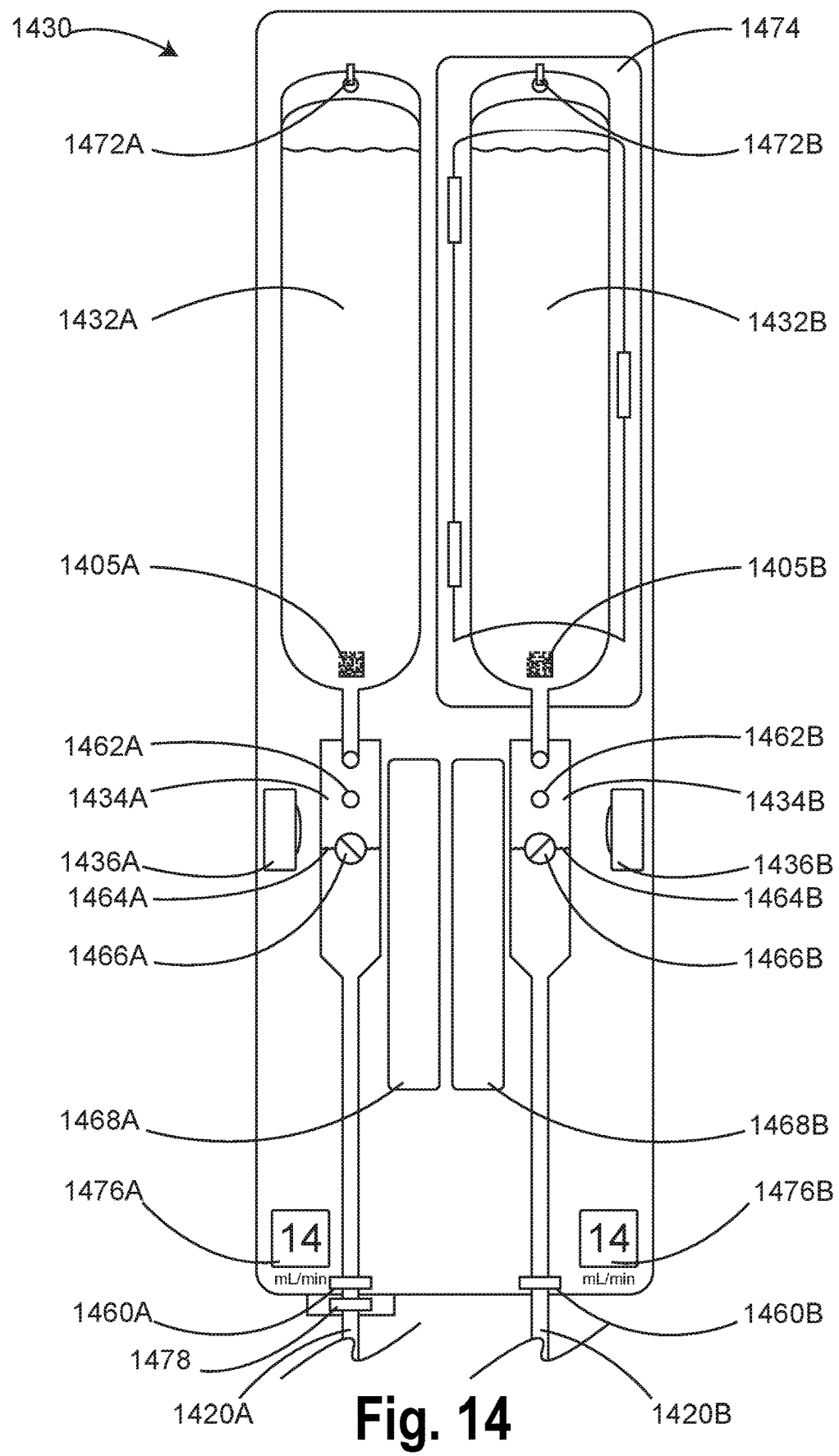
FIG. 14 illustrates a side view of an example IV fluid identification and measurement system that can be used with the systems of FIGS. 1 and 2, and injection port cassette of FIG. 10, in accordance with at least one example of this disclosure.

Some aspects of FIG. 2, including an IV fluid identification and measurement system 130, are described with respect to other figures, including the description of IV fluid identification and measurement system 1430 of FIG. 14.

As shown in FIG. 2, an example medication identification and measurement system 228 may be attached to a relocation module 201 that may be advantageously positioned proximate the patient 202, such as near the patient's head on a surgical table 212. In this position medications can be conveniently administered by medical personnel while also tending to and observing the patient 202 during surgery.

It would be difficult or even impossible to manage the uncontained waste heat produced by electronic and electromechanical equipment mounted on a simple open rack because it can escape in any direction. In some examples, the automated dose-response record system 100,200 can include a cowling (e.g., 299C; FIG. 2) covering substantially the entire outer or inner surface of the housing 299. The cowling 299C not only protects the equipment from accidental fluid damage but also confines the waste heat from the electronic and electromechanical equipment mounted within the automated dose-response record system 100,200 to the inside of the module 201 and cowling 299C. In some examples, the confined waste heat can then be safely managed.

In some examples, the cowling 299C cover of the automated dose-response record system 100,200 can form or support a waste heat management system. In some examples, the cowling 299C can be provided on an inner surface of the housing 299. In some examples, the cowling 299C can be described as an insulation. In some examples, the housing 299 can include other types of insulation from heat and/or water. Any suitable type of insulated housing 299 suitable for use in a surgical field can be provided.

In some examples, the medication identification and measurement system 128 (FIG. 1), 228 (FIG. 2) may include one or more sensors, such as one or more of: a barcode reader or QR code reader (e.g., 436, FIG. 4), a radio-frequency identification (RFID) interrogator (e.g., 438, FIG. 4), or any other suitable sensor for accurately and reliably identifying a medication for IV administration. As defined herein, a barcode reader can include any other type of identifying reader, such as, but not limited to, a QR code reader. Likewise, the RFID interrogator can be any type of interrogator and is not limited to those interrogators based on radio frequency. Examples of such sensors are described herein, such as in FIGS. 4 and 5.

In some examples, instead of, or in addition to one or more of an RFID interrogator 438 and a barcode reader 436, the medication identification and measurement system 128, 228 can receive an input to determine the identity. For example, the medication identification and measurement system 128, 228 can include one or more of: a sensor, such as barcode reader 436 of FIG. 4, configured to identify the one or more IV medications or fluids, or an input configured to receive the identity of the one or more IV medications or fluids, such as via the anesthetic record input component 224.

In some examples, the barcode reader (e.g., 436, FIG. 4) may be a "computer vision" or "machine vision" camera with the capability of reading barcodes. The term "machine vision" is often associated with industrial applications of a computer's ability to see, while the term "computer vision" is often used to describe any type of technology in which a computer is tasked with digitizing an image, processing the data it contains and taking some kind of action. In this disclosure the terms "machine vision" and "computer vision" may be used interchangeably. In some examples, multiple machine vision camera's can be used to perform various functions described herein. Traditionally, machine vision includes technology and methods used to provide imaging-based automatic inspection and analysis, process control, and robot guidance. Machine vision is sometimes used in manufacturing environments. Machine vision refers to many technologies, software and hardware products including processing circuitry, integrated systems and methods.

The inventors have discovered that machine vision can be useful beyond its traditional uses. The inventors discovered that machine vision can be advantageous in implementing an automated dose-response record system 100, 200 because it offers reliable measurements, gauging, object recognition, pattern recognition and liquid fill level measurements. Machine vision does not get tired or distracted. Machine vision excels at quantitative measurement of a structured scene because of its speed, accuracy and repeatability. However, it does require the scene to be structured to perform the desired function.

Machine vision can be very accurate for measuring size of an object at a known distance or the distance of an object of known size. However, it cannot do both. Therefore, in some examples it is important to know the exact location of a syringe (e.g., 406, FIG. 4) and thus know the distance from the camera (e.g., 436, FIG. 4) to the syringe (e.g., 406, FIG. 4) in order for the machine vision to calculate the distance of the movement of the plunger (e.g., 446, FIG. 5) within the syringe (e.g., 406, FIG. 5). This is what we mean by the "scene being structured."

Machine vision may be advantageous for the automated dose-response record system 100, 200 of this disclosure because it "sees" and measures, but does not touch or interfere with the healthcare provider doing their normal job of injecting medications or administering IV fluids. Further, the same visual image that is used by the machine vision software can be transmitted and displayed on a screen 126, 226 to give the operator (whose fingers can be pushing the plunger 446 of the syringe 406, a close-up view of the syringe 406. FIG. 5 is a cross-section view taken at 5-5 of FIG. 4. The machine vision camera 436 can be looking at the same view of the syringe 406 as the operator and it is the same or similar view that the operator would see if they were injecting IV medications the traditional way.

The machine vision camera, or digital camera, can include machine vision software, or the machine vision camera can be in electrical communication with (e.g., operably coupled to) one or more hardware processors, such as processing circuitry 157, 257 and one or more machine-readable mediums 159, 259. The one or more machine-readable mediums 159, 259 can include instructions (e.g., software), that when implemented on the processing circuitry 157, 257, can perform the functions described herein. The processing circuitry 157, 257 can be stored in the module 101, relocation module 201 or remote from the modules 101, 201 (e.g. in a wired or wireless manner). The one or more machine-readable mediums 159 can be a storage device, such as a memory located in the module 201 or remote from the module 101, 201.

In some examples, the RFID interrogator 438 may be either High Frequency (HF) or Near Field (NF) RFID in order to advantageously limit the read-range to a distance of less than 12 inches. In some examples, the RFID read-range may advantageously be limited, such as to less than 8 inches so that only a specific medication injection is identified at any time. In a possibly more preferred example, the RFID read-range may be limited to less than 4 inches to further prevent mis-readings. NF-RFID has a short read-range by definition and the read-range of HF-RFID can be easily limited by restricting the size of the antenna on the tag. In contrast, longer read-range RFID such as Ultra-high Frequency (UHF-RFID) may confusingly interrogate every RFID tag in the operating room and thus be unable to identify which medication is being delivered to the medication identification and measurement system 128, 228. However, any suitable RFID range for a particular application may be used.

Figure 3:
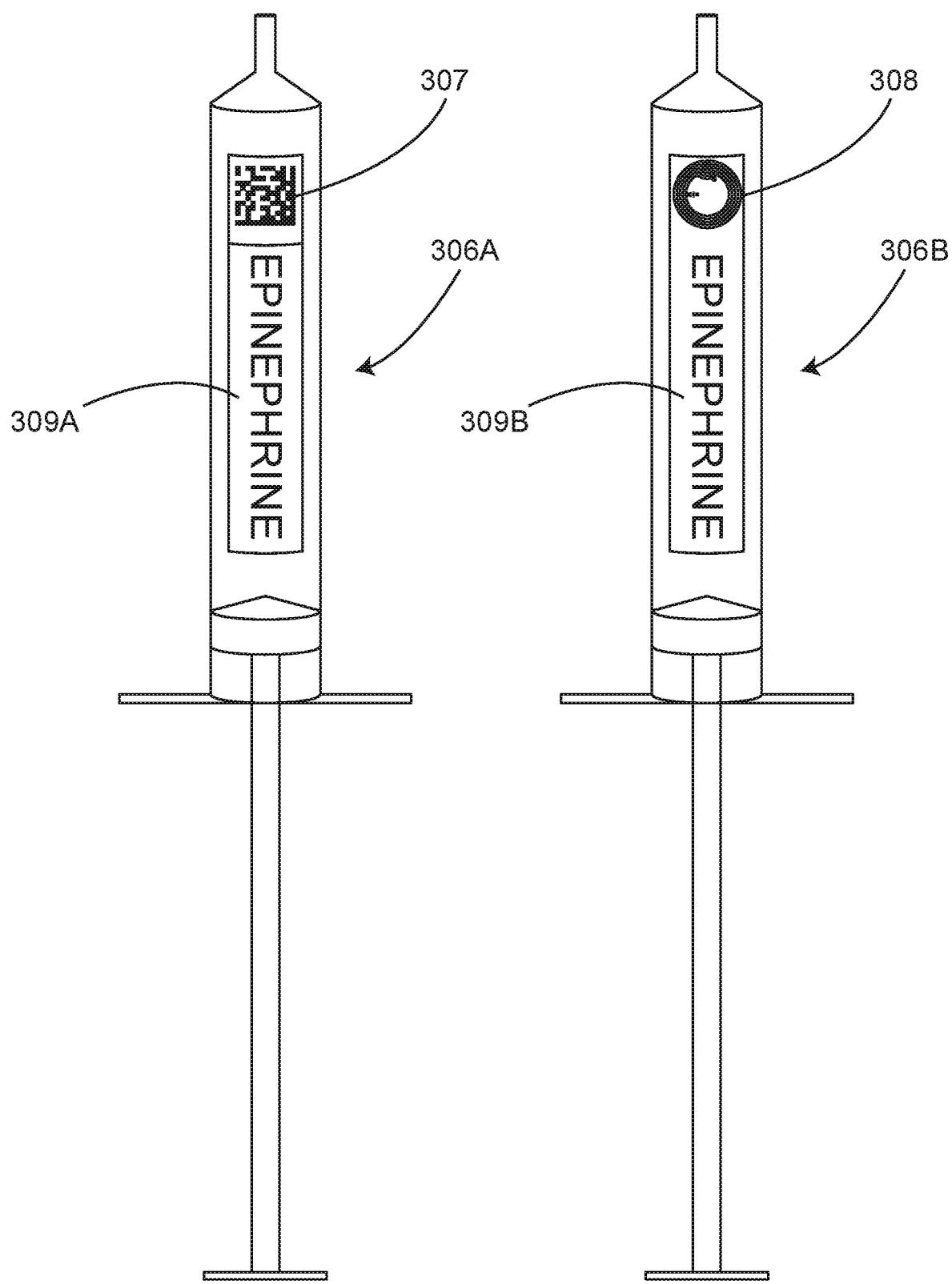
FIG. 3 illustrates a plan view of an example of preloaded syringes that can be used with the system of FIGS. 1 and 2, in accordance with at least one example of this disclosure.

FIG. 3 illustrates a plan view of an example of preloaded syringes 306A and 306B that can be used with the automated dose-response record system 200 of FIG. 2.

The one or more preloaded syringes 306A and 306B may be labeled with a unique barcode label 307 or an RFID tag 308 that may identify one or more of the drug, the concentration, the lot number, the expiration date, the manufacturer and other important information. In some examples, a unique barcode label 307 may be a "2-D" barcode label in order to include more information on a smaller area than traditional barcode labels. In some examples, the barcode label 307 or RFID tag 308 includes the drug identifying label 309A and 309B for convenient use by the caregiver.

In some examples, the syringes 306A and 306B can be filled at the point of use and may be labeled with drug labels 309A and 309B and either barcode labels 307 or RFID tags 308 that are removably attached to the drug bottle or vial at the factory or pharmacy. The drug labels 309A and 309B and either barcode labels 307 or RFID tags 308 may be easily removed from the drug bottle or vial and adhesively attached to the syringe 306A or 306B at the time that the syringe 306A or 306B is loaded with the drug by the caregiver. Instead of, or in addition to the barcode labels 307 or RFID tags 308, any other suitable "tag/reader" system known in the arts, may be used.

Figure 4:
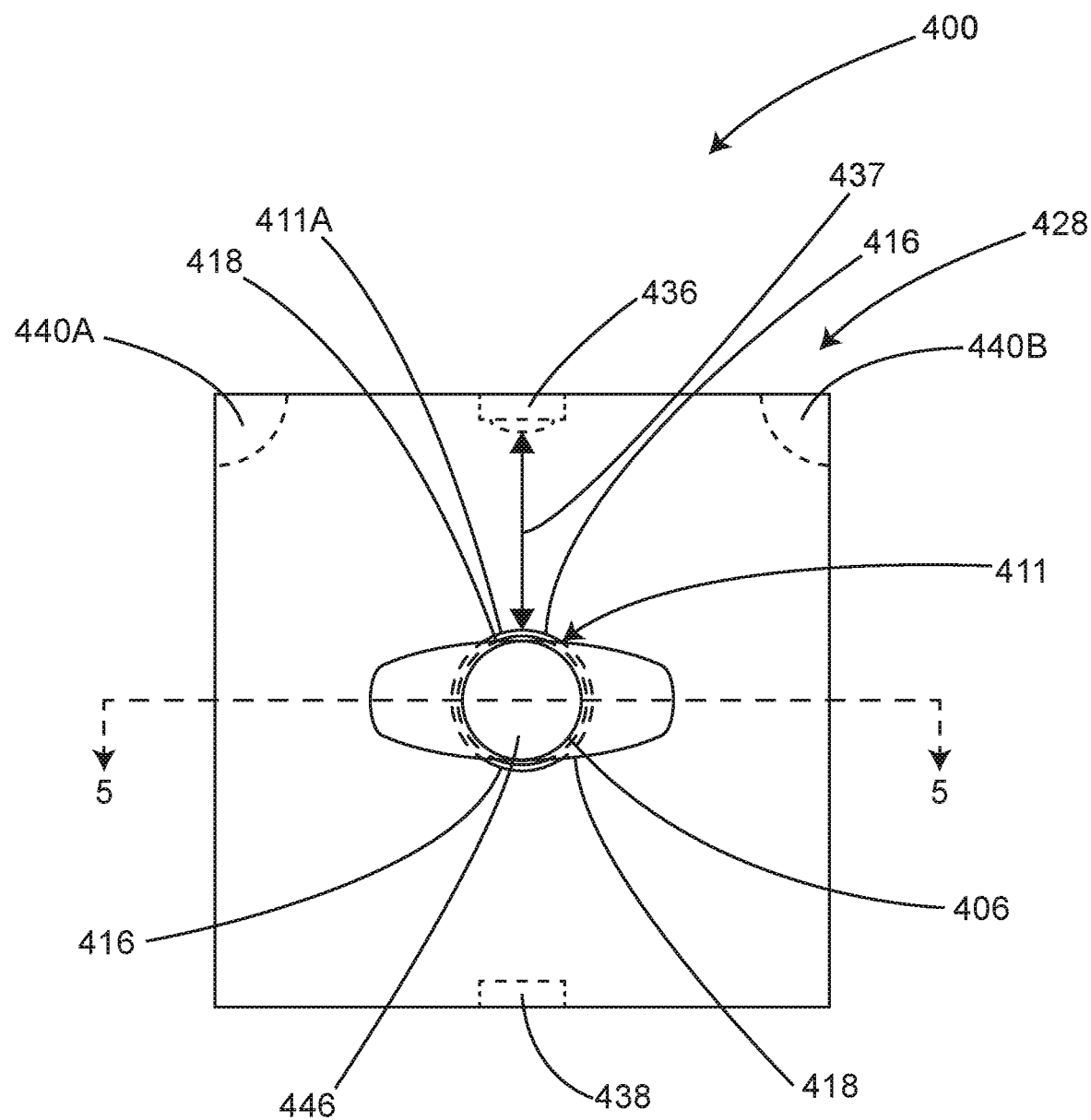
FIG. 4 illustrates a side view of an example medication identification and measurement system and a syringe that can be used with the system of FIGS. 1 and 2, to monitor drug delivery, in accordance with at least one example of this disclosure.
Figure 5:
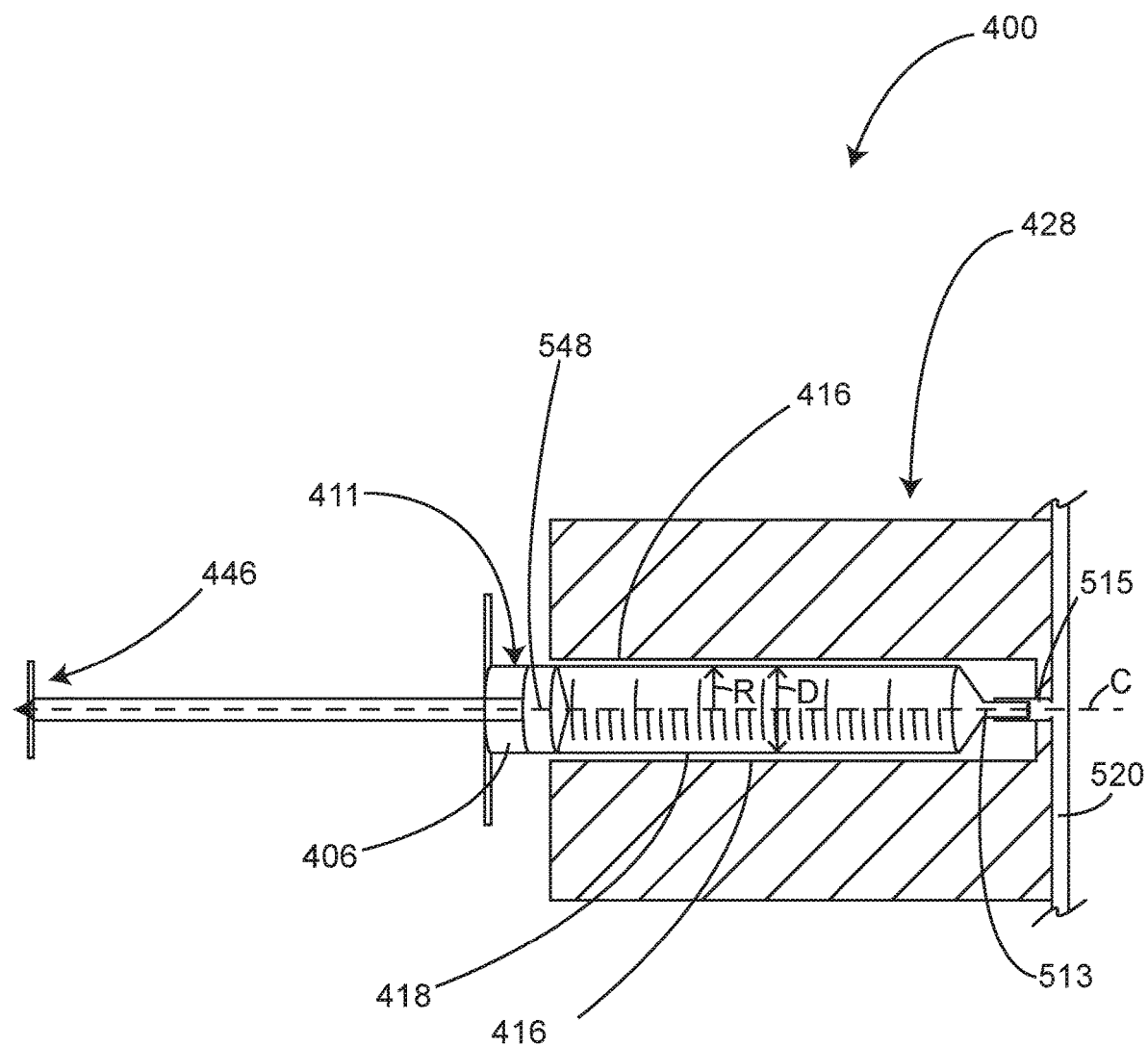
FIG. 5 illustrates a cross-sectional view of the medication identification and measurement system and a syringe (not shown in cross-section) of FIG. 4, taken along line 5-5, in accordance with at least one example of this disclosure.

FIGS. 4-10 illustrate examples of medication identification and measurement systems 428, 628, 828 that can be used with the automated dose-response record systems 100, 200 of FIGS. 1 and 2. However, aspects of the medication identification and measurement systems 428, 628 and 828 may be used with other systems, and other medication identification and measurement systems may be used with the automated dose-response record systems 100, 200. Furthermore, some examples of the automated dose-response record systems 100, 200 can omit aspects of the medication identification and measurement systems, or can omit a medication identification and measurement system altogether. FIG. 4 illustrates a portion of an automated dose-response record system 400 including a side view of an example medication identification and measurement system 428 and a syringe 406 that can be used with the automated dose-response record systems 100, 200 of FIGS. 1 and 2, to monitor drug delivery. FIG. 5 illustrates a cross-sectional view of the medication identification and measurement system 428 and the syringe 406 (not shown in cross-section) of FIG. 4, taken along line 5-5. FIGS. 4 and 5 are described together.

As shown FIGS. 4 and 5, the medication identification and measurement system 428 may include at least one injection portal 411 (also see 211, FIG. 2). The injection portal 411 may be a receptacle for accommodating a syringe 406 in a fixed and known location and can be configured to orient the Luer taper connector 513 to mate with an injection port 515. The injection port 515 can be secured within the injection portal 411 and can be in fluid communication with IV tubing 520. In some examples, the injection portal 411 may include an injection portal tube 416, such as a transparent tube that is sized to receive and accommodate a syringe barrel 418 of a syringe 406. In some examples, the injection portal can be configured to receive a specific size syringe barrel 418. In some examples, multiple injection portals 411 can be provided to accommodate syringes 406 of different sizes.

Figure 6:
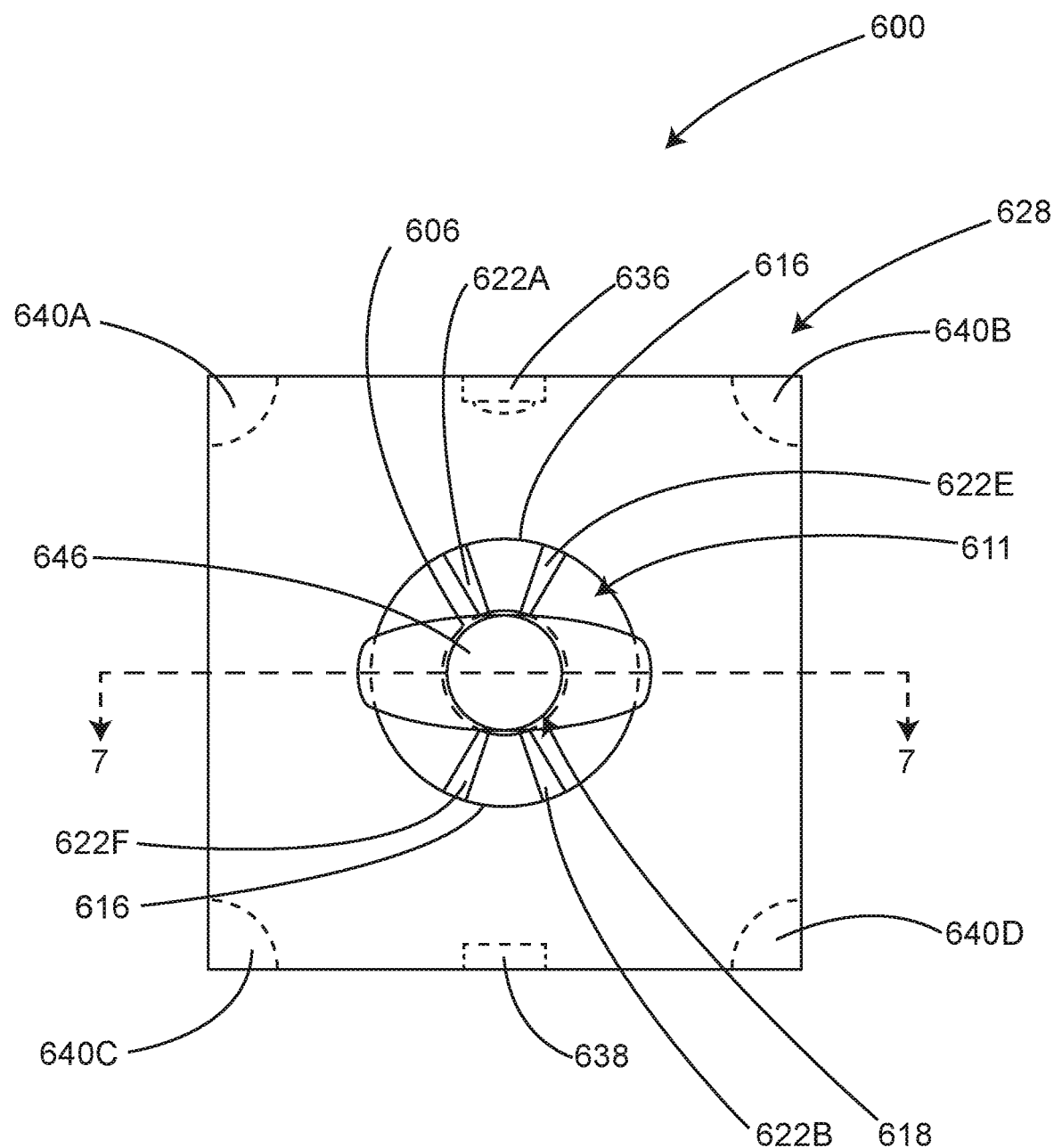
FIG. 6 illustrates a side view of a second example medication identification and measurement system and a syringe that can be used with the system of FIGS. 1 and 2, in accordance with at least one example of this disclosure.
Figure 7:
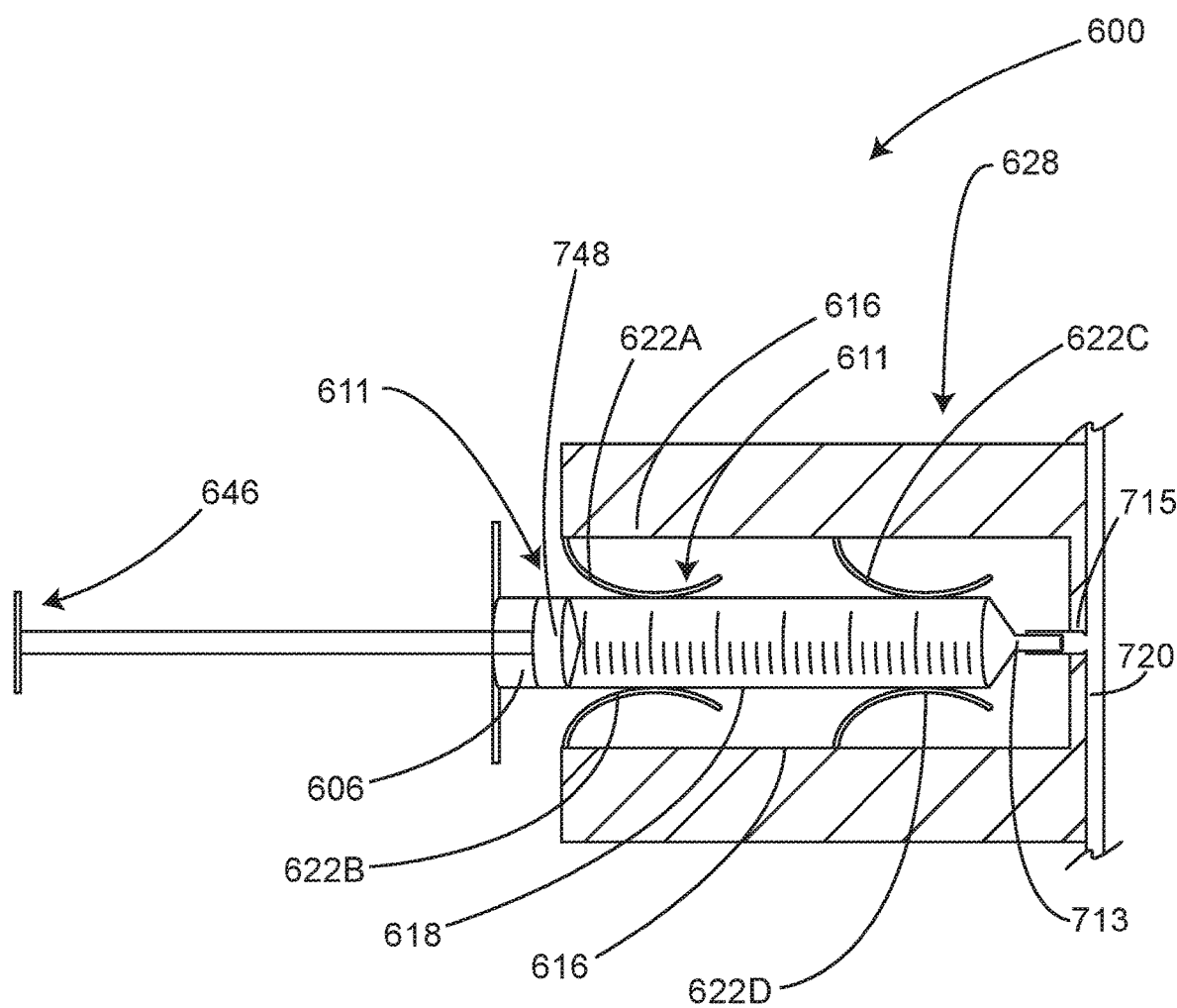
FIG. 7 illustrates a cross-sectional view of the second example of a medication identification and measurement system and the syringe (not shown in cross-section) of FIG. 6, taken along line 7-7, in accordance with at least one example of this disclosure.

FIG. 6 illustrates a portion of an automated dose-response record system 600 including a side view of a second example of a medication identification and measurement system 628 and a syringe 606 that can be used with the automated dose-response record systems 100, 200 of FIGS. 1 and 2, to monitor drug delivery. FIG. 7 illustrates a cross-sectional view of the second example of a medication identification and measurement system 628 and the syringe 606 (not shown in cross-section) of FIG. 6, taken along line 7-7. FIGS. 6 and 7 are described together.

As shown in FIGS. 6 and 7, the injection portal 611 of the medication identification and measurement system 628 may be large enough to accommodate syringes 606 of multiple sizes within the space defined by a real or imaginary injection portal tube 616. In this example, accurately orienting the Luer taper connector 713 to mate with an injection port 715 may be accomplished by one or more orienting members such as one or more spring positioning members 622A-F that engage with the syringe barrel 618 to center it in the injection portal 611. In some examples, there may be two or more rows of spring positioning members 622A-F. For example, spring positioning members 622A, B, E, F may be located near the entrance to the injection portal 611 and spring positioning members 622C, D may be located near the injection port 715 to assure accurate positioning for mating with the Luer taper connector 713. Spring positioning members 622A-F may include not only spring wires or metal or polymer or plastic spring pieces but any flexible material or combination of materials or shapes that can be deformed by the syringe barrel 618 entering the injection portal 611 and retain a memory (e.g., elastically deformable, substantially elastically deformable, resiliently deformable, resilient member) so as to urge the syringe barrel 618 into a centered position within the space defined by a real or imaginary injection portal tube 616.

One objective of the spring positioning members 622A-F can be to "automatically" center and align the Luer taper connector 713 of the syringe 606 with the injection port 715, so that the operator can simply and conveniently push the syringe 606 into the injection portal 611 and no further manual alignment may be needed. The spring positioning members 622A-F can also obviate the need for the operator to touch either the Luer taper connector 713 of the syringe 606 or the injection port 715, thus beneficially preventing accidental infectious contamination by the operators' fingers and gloves.

Figure 8:
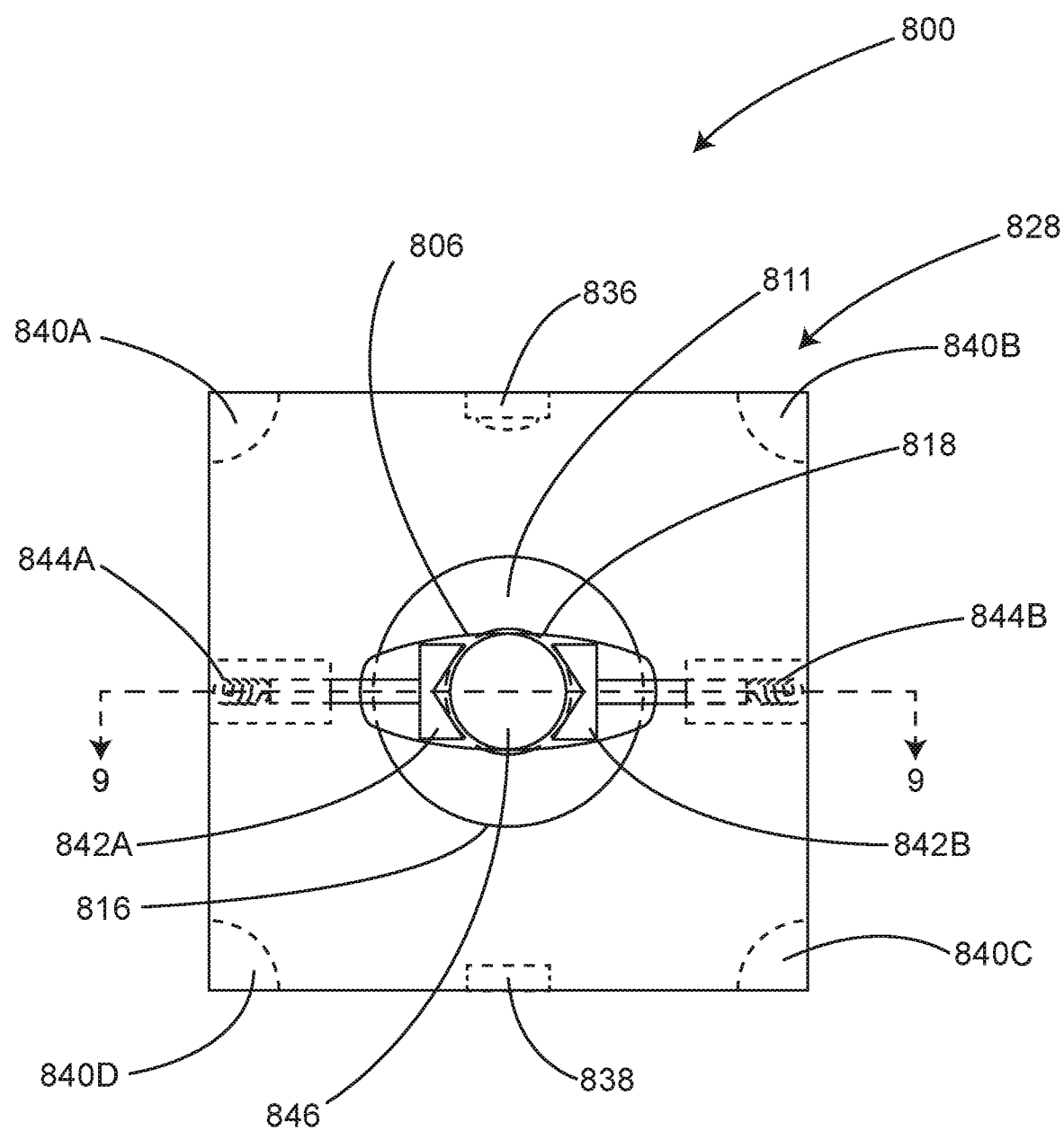
FIG. 8 illustrates a side view of a third example of a medication identification and measurement system and a syringe that can be used with the system of FIGS. 1 and 2, in accordance with at least one example of this disclosure.
Figure 9:
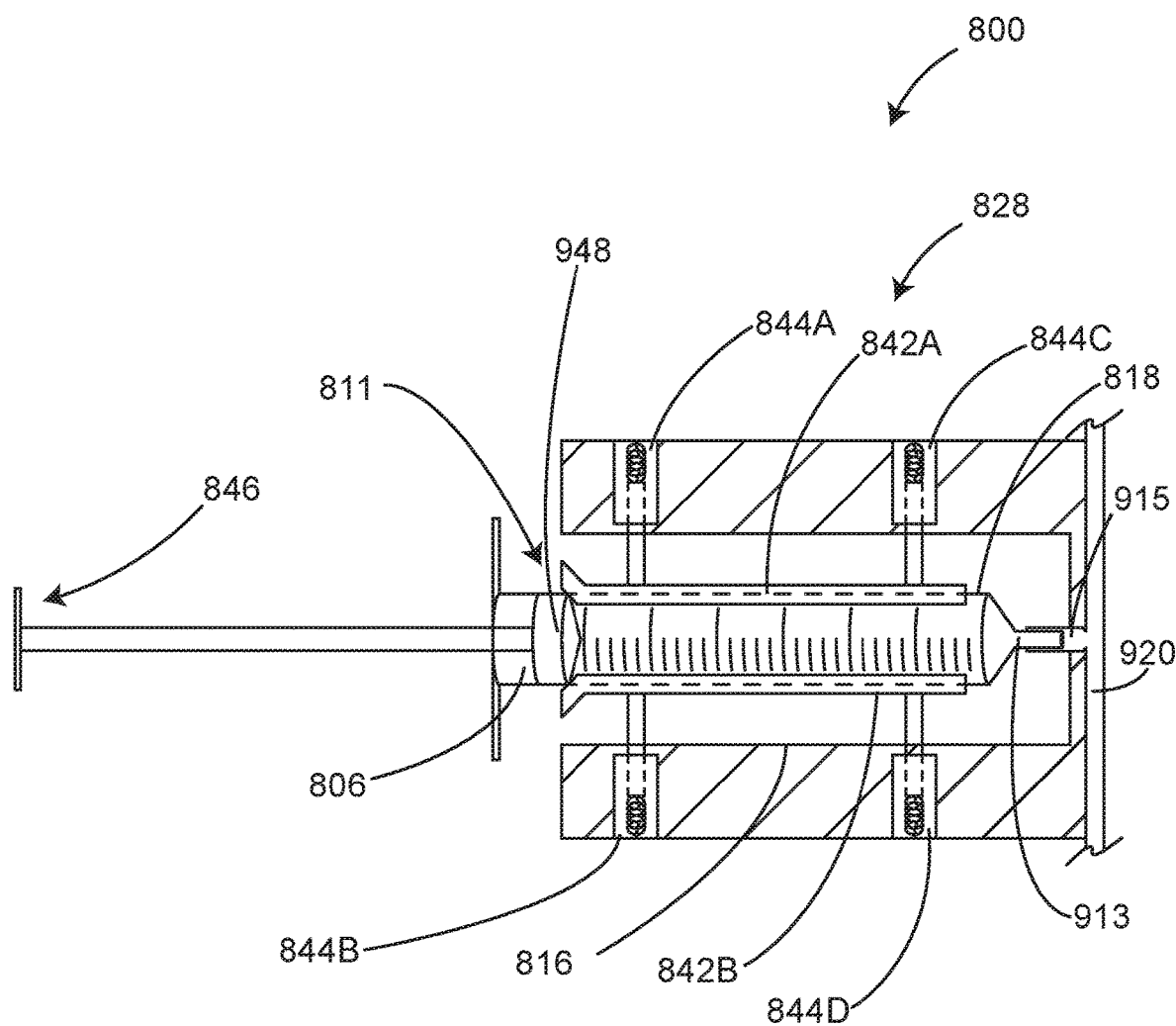
FIG. 9 illustrates a cross-sectional view of the third example of a medication identification and measurement system and the syringe (not shown in cross-section) of FIG. 8, taken along line 9-9, in accordance with at least one example of this disclosure.

FIG. 8 illustrates a portion of an automated dose-response record system 800 including a side view of a third example of a medication identification and measurement system 828 and a syringe 806 that can be used with the automated dose-response record systems 100, 200 of FIGS. 1 and 2. FIG. 9 illustrates a cross-sectional view of the third example of a the medication identification and measurement system 828 and the syringe 806 (not shown in cross-section) of FIG. 8, taken along line 9-9. FIGS. 8 and 9 are described together.

As shown in FIGS. 8 and 9, a syringe barrel 818 may be centered and held in place by one or more orienting members, such as compression positioning members 842A,B. The compression positioning members 842A, B may be urged apart by inserting the syringe barrel 818 there between. Springs 844A-D can compress and create a pressure pushing the compression positioning members 842A,B against syringe barrel 818. The compression positioning members 842A,B shown in FIGS. 8 and 9 are merely illustrative, and many other sizes, shapes, numbers and locations of compression positioning members 842 are anticipated.

Compression positioning members 842A,B may be simple spring 844A-D activated devices (e.g., resilient members) as shown in FIGS. 8 and 9 or may be any mechanism that can expand (e.g., resiliently expand) to accommodate syringe barrels of various sizes and urge the syringe barrel 818 into a centered position within the space defined by a real or imaginary injection portal tube 816. This example shows spring 844A-D activated compression positioning members 842A,B but many other mechanical activation mechanisms are anticipated. The compression positioning members 842A,B can be elastically deformable, substantially elastically deformable, resiliently deformable, include one or more resilient members.

Other examples of positioning members designed to hold an inserted syringe 806 in the center of the injection portal 811 and thus orienting the Luer taper 913 for mating with the injection port 915 are anticipated. Positioning the inserted syringe 806 in the center of the injection portal 811 allows the machine vision to work from a known distance and thus calculations of syringe plunger 948 movement can be very accurate.

In some examples, instead of the positioning members shown in the examples of FIGS. 6-9 holding a syringe centrally, the positioning members 622A or 842A,B can be designed to hold an inserted syringe 606, 806 at a known, but off center position in the injection portal 611, 811, such as when the injection port 715, 915 (FIGS. 7 and 9) is positioned off center in the injection portal 611, 811. Any arrangement of at least one positioning member that aligns an inserted syringe at a known position may be provided.

In some examples, and as shown in FIGS. 4, 6 and 8 the medication identification and measurement system 428, 628, 828 of this disclosure may include one or more "machine vision" cameras 436, 636, 836 that input digital images into one or more processors having processing circuitry 157, 257 as shown and described in FIGS. 1,2, that is programed to analyze machine vision images. In some examples, one of the images that the machine vision cameras 436, 636, 836 may "see" is a barcode label 307 on the syringe 406, 606, 806, that has been inserted into the injection portal 411, 611, 811, for identifying the medication in the syringe 406, 606, 806. As previously noted, the barcode label 307 can identify the brand name and/or generic name of the medication in the syringe. In some examples, the barcode label 307 also may identify one or more of the concentration of the medication, the lot number, the expiration date and other information that may be useful for inventory management.

As shown in FIGS. 4, 6 and 8, the automated dose-response record system 400, 600, 800 of this disclosure can include one or more radio frequency identification (RFID) interrogation antennas 438, 638, 838 that input RFID information into a processor, such as processing circuitry 157, 257 as shown and described in FIGS. 1 and 2, that is programed to analyze RFID data. In some examples, the RFID interrogation antennas 438, 638, 838 can interrogate a RFID tag 308 (FIG. 3) attached to the syringe 406, 606, 806, that has been inserted into the injection portal 411, 611, 811, for identifying the medication in the syringe 406, 606, 806. In some examples, short range RFID such as near field (NF) or high frequency (HF) may be advantageous because they may only detect the syringe 406, 606, 806 that is adjacent to or inside the security system for IV medications 400, 600, 800, and not detect the various other medication syringes that may be sitting on the worktable such as 206A-206C in FIG. 2.

As shown in FIGS. 4, 6 and 8 the medication identification and measurement system 428, 628, 828 of this disclosure may include a RFID interrogator 438, 638, 838. In some examples, the RFID interrogator 438, 638, 838 that can include antennas that may be located inside the medication identification and measurement system 428, 628, 828. In some examples, the RFID interrogator antennas 438, 638, 838 may be located external to but proximate the medication identification and measurement system 428, 628, 828. As the syringe 406, 606, 806 is brought into proximity of the medication identification and measurement system, the RFID interrogator 438, 638, 838 can interrogate the RFID tag 308 on the syringe 406, 606, 806, thereby accurately and reliably identifying a medication for IV administration. In some examples, the RFID tag 308 or other marker may include one or more of: the generic and brand name of the drug, the concentration, the lot number, the expiration date, the manufacturer and other important information that may be recorded. In some examples, the generic and brand name of the drug and the concentration of the drug can be displayed in the injection section of a display such as the display 126, 226 (FIGS. 1, 2).

Machine vision is very accurate for measuring the size of an object at a known distance or the distance of an object of known size. However, it cannot do both. Therefore, in some examples it is important to know the exact location of a syringe and thus know the distance from the camera to the syringe in order to accurately calculate the distance of the movement of the plunger within the syringe.

Syringes are available in multiple sizes such as 3 cc, 6 cc and 12 cc, each of which is a different diameter. The machine vision processor must know both the internal diameter of the barrel of the syringe and the distance that the syringe plunger moves down the barrel, in order to calculate the volume of medication injected, unless it has another source of information. The machine vision of this disclosure can measure the diameter of the syringe because in the examples the syringe 406, 606, 806 is held at known distance and in a centered location relative to the machine vision cameras 436, 636, 836. Alternately, the security system for IV medications 400, 600, 800 of this disclosure may be programed to know that the particular hospital uses only Monoject® syringes for example and the internal diameter of each Monoject® syringe size may be pre-programed into the computer. In this case, the machine vision only needs to differentiate 3 cc, 6 cc and 12 cc syringe sizes from each other. The machine vision processor can determine the internal diameter of the barrel of the syringe. In some examples, the syringe size may be included in the information provided by the barcode 307 or RFID 308 (FIG. 3).

In some examples, such as the examples of FIGS. 4-9, the machine vision system, including the machine vision camera 436, 636, 836 and the processor 157, 257 of FIGS. 1 and 2 (e.g., processing circuitry) in electrical communication with the machine vision camera 436, 636, 836, can visually detect and determine other geometry information about the syringe 406, 606, 806 besides the outside diameter, such as determining the inside diameter, or the inner or outer length of the syringe. The medication identification and measurement systems 428, 628, 828 can use the geometry information to determine the size or type of the syringe 406, 606, 806, or can use the geometry information to calculate a volume of the syringe 406, 606, 806.

In some examples, as the syringe 406, 606, 806 is advanced into the injection portal 411, 611, 811, the image of the syringe 406, 606, 806 entering the injection portal 411, 611, 811 is displayed in real time in an injection section 126a, 226a of the display 126, 226 (FIGS. 1 and 2). Therefore, the caregiver can watch the syringe 406, 606, 806 advance and engage with the injection port 515, 715, 915. In some examples, the injection portal tube 416, 616, 816 or the spring positioning members 622A-E or the compression positioning members 842A,B, urge the syringe 606, 806 into position to mate with the injection port 715, 915 but the actual connection can also be observed as it is happening by the caregiver on the display 126, 226. Even though the caregiver is not physically holding the injection port 515, 715, 915 as they typically would, they can watch the engagement of the Luer connector 513, 713, 913 with the injection port 515, 715, 915 on a display 126, 226, the view is essentially identical to the thousands of injections that they have made during their career. In some examples, the actual image of the syringe 406, 606, 806 can be displayed on the display 126, 226, while in other examples the data obtained by the camera 436, 636, 836 can be converted to a representation of the syringe displayed on the display 126, 226.

In some examples, once the syringe 406, 606, 806 is securely connected to the injection port 515, 715, 915, the caregiver pushes on the plunger 446, 646, 846 of the syringe 406, 606, 806, injecting the medication into the injection port 515, 715, 915 and IV tubing 520, 720, 920. The caregiver can visualize the plunger seal 548, 748, 948 move down the syringe barrel 418, 618, 818 and can determine the volume of medication injected by the graduated markings on the syringe 406, 606, 806. Thus, the engagement of the Luer connector 513, 713, 913 with the injection port 515, 715, 915 and the injected volume are observed by the caregiver on the display 126, 226 and the traditional method and routine of injection is minimally altered by implementing the automated dose-response record system 100, 200 including the example medication identification and measurement systems 428, 628, 828.

In some examples, the processing circuitry 157, 257 (FIGS. 1 and 2) or a computer may also simultaneously generate data representing a running total of the volume and dosage of the injected medication and can transmit the generated data to the display 126, 226 to display volume and dosage information on the display 126, 226. In some examples, the processing circuitry 157, 257 or a computer may also generate its own graduated scale and transmit the generated graduated scale information to the display 126, 226 to superimpose the scale on the image of the syringe 406, 606, 806 or next to the image of the syringe 406, 606, 806, for added visual clarity of the injected volume and dose.

In some examples, the machine vision determination of the injected volume may be calculated by multiplying the internal cross-sectional area of the syringe ($\pi r^2$) by the distance that the syringe plunger moves. The radius of the syringe may be determined in one or more ways. For example, the machine vision function may determine that the syringe approximates a 3 cc or 12 cc syringe and the computer is programed to know that the hospital uses a specific brand of syringes and the internal diameter (radius) of each of these syringe sizes is precisely known. (An example of diameter D, radius R, longitudinal direction, axis or centerline C is shown in FIG. 5) Another example may require the machine vision camera to measure the outer diameter of the syringe and then subtract an approximated wall thickness (either measured or known value stored in a memory) from the measured diameter to determine the internal diameter. In another example, the internal diameter of the syringe may be supplied to the processing circuitry 157, 257 or a computer as part of the RFID 308 or barcode 307 information. In another example, the machine vision may determine the inner diameter of the syringe by determining an outer diameter of the plunger as viewed through the transparent or semi-transparent syringe and determine the wall thickness, In yet another example, the machine vision may be able to visibly determine the inner diameter or radius directly through the transparent or semi-transparent syringe. Any other suitable determination, calculation or algorithm may be used to determine the radius, diameter and injected volume.

In some examples, the machine vision determination of the distance that the syringe plunger 446, 646, 846 moves may be by "observing" the movement of the black rubber plunger seal 548, 748, 948 against the visible scale printed on the syringe 406, 606, 806. In this example, the machine vision can be programed to recognize the markings on the syringe 406, 606, 806.

In some examples, the machine vision determination of the distance that the syringe plunger 446, 646, 846 moves may be by observing the movement of the black rubber plunger seal 548, 748, 948 relative to a scale calculated by the processing circuitry 157, 257 (FIGS. 1 and 2). The geometrical calculation of the scale that determines the distance that the syringe plunger 446, 646, 846 moves may be easiest to determine along the widest part of the syringe that corresponds with the center C (FIG. 5) of the syringe 406, 606, 806, which is a known distance from the machine vision camera 436, 636, 836. Alternatively, the computer-constructed scale may be applied to the side of the syringe 406, 606, 806 facing the camera 436, 636, 836, if the radius of the syringe 406, 606, 806 is subtracted from the known distance to the center C (FIG. 5) of the syringe 406, 606, 806 in order to calculate the distance 437 from the machine vision camera 436, 636, 836 to the near side (e.g., 411A) of the syringe 406, 606, 806.

In some examples, the movement of the black rubber plunger seal 548, 748, 948 of the syringe 406, 606, 806 can be clearly identifiable by the machine vision camera 436, 636, 836 and a scale to determine the distance moved by the plunger 446, 646, 846 can either be "visualized" or constructed by the machine vision computer (e.g., processing circuitry). Multiplying the distance that the plunger seal 548, 748, 948 moves by the known or measured internal diameter d (FIG. 5) of the syringe 406, 606, 806 and thus cross-sectional area of the plunger seal 548, 748, 948, allows the processing circuitry 157, 257 or a computer in electrical communication with the processing circuitry 157, 257 to calculate an accurate injected volume. The measured injection volume and dosage may be displayed on the display 126, 226 of the module 101, 201 (FIGS. 1 and 2). Without interfering with or changing the anesthesiologists' normal or traditional medication injection routines, an unobtrusive machine vision camera 436, 636, 836 and computer (e.g., processing circuitry) can "observe" the medication injections and automatically record them in the EMR.

In some examples, the injected volume of medication may be determined by other sensors or methods. For example, the systems described herein can employ (e.g., substitute) other sensors such as a non-visual optical sensor 436A in place of or in addition to the machine vision camera 436, 636, 638 described in FIGS. 4-9. For example, a light source can shine on one or more light sensitive elements such as photodiodes, and the position of the plunger of the syringe can be roughly determined by the obstruction of the light beam by the plunger. Other fluid measurement methods can have a sensor including adding magnetic material to the syringe plunger and detecting movement of the plunger with a magnetic proximity sensor. Alternatively, fluid flow may be measured with fluid flow meters in the IV fluid stream. These examples are not meant to be an exhaustive list but rather to illustrate that there are alternative technologies to machine vision (e.g., sensors), for noncontact measurement (e.g., sensing) of fluid flow from a syringe that are anticipated in this disclosure.

In some examples, the injected volume of medication may be determined by other sensors or methods. For example, the systems described herein can employ (e.g., substitute) other sensors in place of or in addition to the machine vision cameras for either or both the medication and fluid flows. Other fluid flow sensors anticipated by this disclosure include but are not limited to: ultrasonic flow meters, propeller flow meters, magnetic flow meters, turbine flow meters, differential pressure flow meters, piston flow meters, helical flow meters, vortex flow meters, vane flow meters, paddle wheel flow meters, thermal flow meters, semicylindrical capacitive sensor flow meters and Coriolis flow meters.

Securing the injection port 515, 715, 915 within the injection portal 411, 611, 811 prevents the caregiver from touching the injection port 515, 715, 915. Normally caregivers wear gloves to protect themselves from infectious contaminates from the patient and operating room and their gloves are nearly always contaminated. Anything they touch will be contaminated. They typically pick up and hold the IV injection port 515, 715, 915 with one hand while inserting the Luer taper connector 513, 713, 913 of the syringe 406, 606, 806 into the injection port 515, 715, 915. In the process, the injection port 515, 715, 915 is frequently contaminated with pathogenic organisms from their gloves that can enter the patient's blood stream with the next injection, causing serious infections. It is therefore advantageous from the infection prevention point of view, if the Luer connection and injection can be accomplished while never touching the injection port 515, 715, 915.

In some examples as shown in FIGS. 4, 6 and 8 the medication identification and measurement system 428, 628, 828 can include one or more ultraviolet (UV) lights 440A, 440B, 640A-D, 840A-D that shine on the injection port 515, 715, 915. The one or more UV lights can be located inside the module (e.g., 101, FIG. 1) of the medication identification and measurement system 128, 228, 428, 628, 828, keeping the injection portal 411, 611, 811 and the injection port 515, 715, 915 disinfected. In some examples, the UV lights 440A, 440B, 640A-D, 840A-D may preferably be in the UV-C part of the light spectrum. UV-C light has been shown to have superior germicidal powers over other parts of the UV spectrum. The UV lights 440A, 440B, 640A-D, 840A-D may shine continuously or intermittently. By making the injection port 515, 715, 915 untouchable because it is inside the module 101 and radiating the injection port 515, 715, 915 with UV-C light, the injection port 515, 715, 915 should be effectively disinfected between each injection and thereby eliminate injection port 515, 715, 915 contamination as a source of bloodstream infection.

Figure 11:
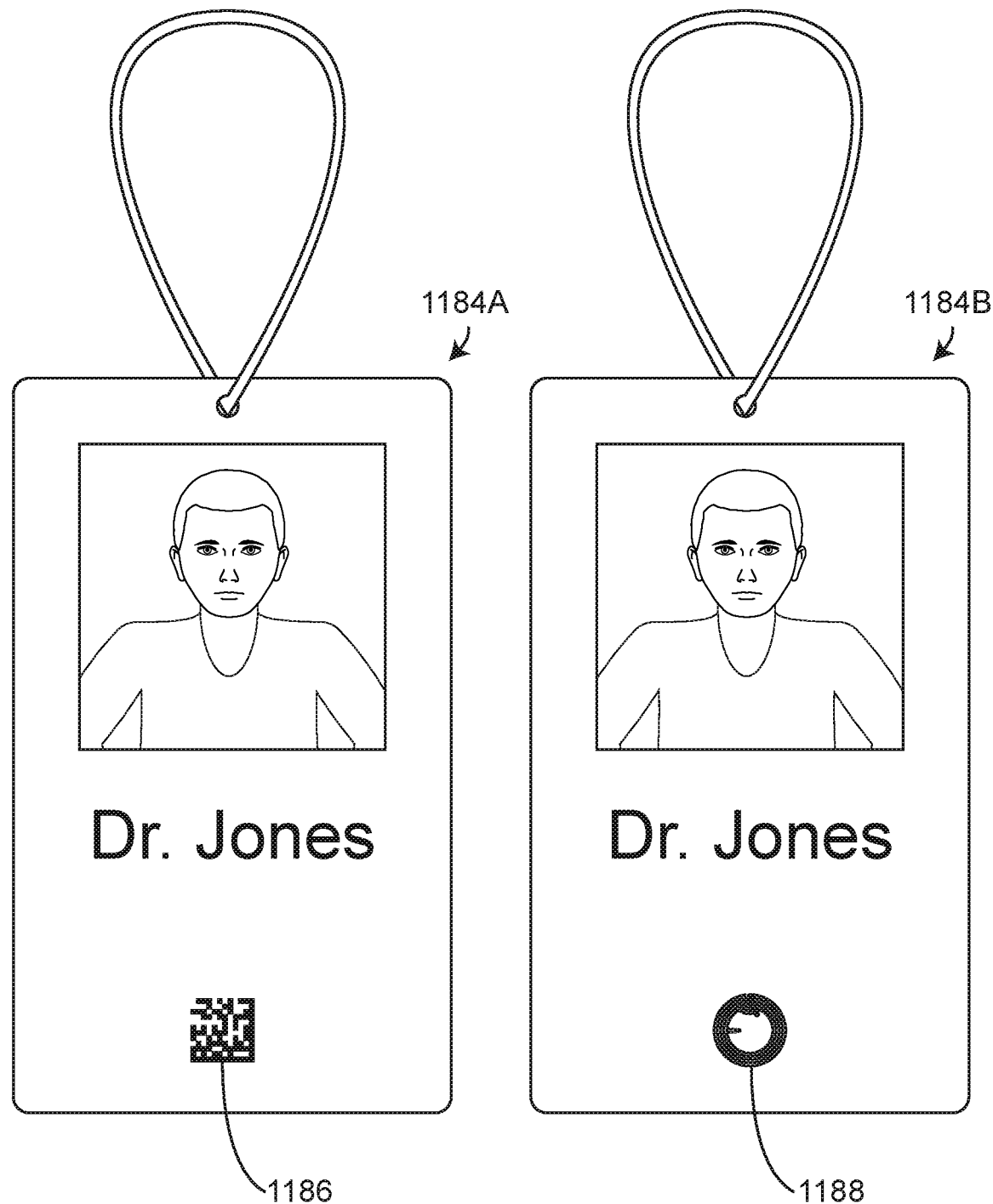
FIG. 11 illustrates a plan view of an example of healthcare provider ID badges that can be used with the system of FIGS. 1 and 2, in accordance with at least one example of this disclosure.

In some examples as shown in FIGS. 1 and 2, the automated dose-response record system 100, 200 may include an external reader, such as barcode reader 180, 280 on the module 101, 201 to read a barcode, QR code or the like for identification. This barcode reader 180, 280 may be used to identify the healthcare provider injecting a medication by reading a barcode or QR code 1186 on the user's ID badge for example (FIG. 11). In some examples as shown in FIGS. 1 and 2, the automated dose-response record system 100, 200 may include an external RFID reader 182, 282 on the module 101, 201. This RFID reader 182, 282 may be used to identify the healthcare provider injecting a medication by reading an RFID tag 1188 on the user's ID badge 1184B for example (FIG. 11). In some examples as shown in FIGS. 4, 6 and 8, the automated dose-response record system 400, 600, 800 may include an internal RFID reader 438, 638, 838 in the module 101, 201. This RFID reader 438, 638, 838 may also be used to identify the healthcare provider injecting a medication by reading an RFID tag on the user's ID badge for example.

It is an important part of the record to know who injected the medication and their identity can be easily verified and documented by the automated dose-response record system 400, 600, 800 using either barcode, QR code or RFID. Other identification technologies are also anticipated.

Figure 10:
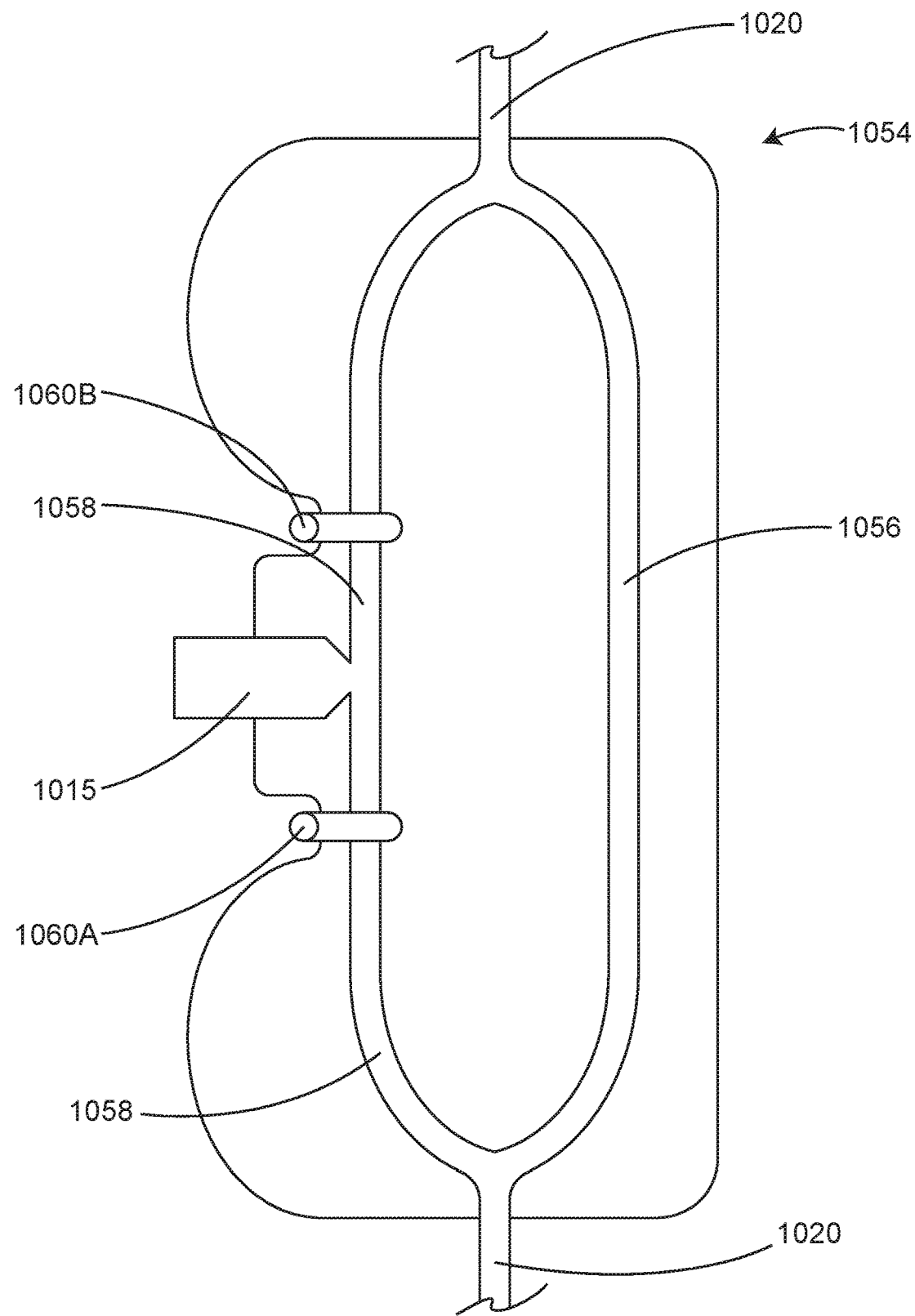
FIG. 10 illustrates an example injection port cassette that can be used with the system of FIGS. 1 and 2, as detailed in FIGS. 5, 7 and 9, in accordance with at least one example of this disclosure.

FIG. 10 illustrates an example injection port cassette 1054 that can be used with the automated dose-response record systems 100, 200 of FIGS. 1 and 2, as detailed in FIGS. 5, 7 and 9. As shown in FIG. 10, the injection port 1015 may be mounted on an injection port cassette 1054 in order to make the attachment to the automated dose-response record system 100, 200, 400, 600, 800 easier and more secure. The injection port cassette 1054 may be a piece of molded polymer or plastic onto which the injection port 1015 and IV tubing 1020 may be attached. The injection port cassette 1054 may be shaped and sized to fit into a slot in the automated dose-response record system 100, 200, 400, 600, 800. When the injection port cassette 1054 is fit into a slot in the automated dose-response record system 100, 200, 400, 600, 800, the injection port 1015 can be positioned substantially in the center of the injection portal 411, 611, 811 for mating with the Luer tapers 513, 713, 913. The injection port cassette 1054 can also be configured to be removed intact from the automated dose-response record system 400, 600, 800 so that the patient can be transferred and the IV tubing 1020 can be moved with the patient and continue to operate normally.

In some examples, and as shown in FIG. 10, the injection port cassette 1054 can include an IV bypass channel 1056 in the IV tubing 1020. The IV bypass channel 1056 can allow the IV fluids to flow unencumbered by the medication injection apparatus. The injection port cassette 1054 can include a medication channel 1058 in the IV tubing 1020 and, the medication channel 1058 may include one or more stop-flow clamps 1060A,B. The one or more stop-flow clamps 1060A,B may be activated by the automated dose-response record system 100, 200, 400, 600, 800 if a medication error is identified. The one or more stop-flow clamps 1060A,B may be powered by one or more electromechanical solenoids that squeeze the IV tubing in the medication channel 1058 flat, obstructing the flow. Other electromechanical flow obstructers are anticipated.

In some situations, such as when administering a drug to a patient allergic to that drug, or administering potent cardiovascular drugs to a patient with normal vital signs, or administering a drug with a likely mistaken identity, the computer, such as processing circuitry 157, 257 (FIGS. 1 and 2) for the automated dose-response record system 100, 200, 400, 600, 800 of this disclosure can automatically activate the stop-flow clamps 1060A,B to compress the medication channel 1058 tubing upstream and/or downstream from the injection port 1015. Compressing the IV tubing both upstream and downstream from the injection port 1015 prevents the injection of any medication into the IV tubing 1020. An alert to the adverse condition of the injection may be displayed on display 126, 226 where the stop-flow condition can be over-ridden by the operator touching a manual override switch on the display 126, 226 or the module 101, 201, if the injection was not erroneous. While the stop-flow can occur in the medication channel 1058, the IV fluid flow can continue normally in the parallel bypass channel 1056.

The stop-flow clamps 1060A,B can allow the processing circuitry 157, 257 (e.g., processor, hardware processing circuitry) of the automated dose-response record system 100, 200, 400, 600, 800 to not only warn the operator of a pending medication error, but physically prevent the injection. Perhaps equally as important is that the stop-flow clamps 1060A,B can be quickly released by the operator touching a manual override switch in the event that the apparent error was in fact a planned event or otherwise desired by the operator.

In some examples, a part of the automated dose-response record system 100, 200, 400, 600, 800 can include the ability for the computer (e.g., machine) to know the patient's medical history, medication orders, vital signs, current medications, medication orders and other important information about that patient. In some examples, the medication in syringe 306 can be identified by RFID tag 308 (FIG. 3) and is detected by RFID interrogator 438, 638, 838 as the syringe 306 enters injection portal 411, 611, 811. The processing circuitry (e.g., 157, 257) of the automated dose-response record system 100, 200, 400, 600, 800 can cross-reference the proposed injection to the patient's medical history, medication orders, vital signs, current medications and other important information about that patient, providing a safety "over-watch" guarding against medication errors. In some examples, the processing circuitry (e.g., 157, 257) of the automated dose-response record system 100, 200, 400, 600, 800 may include algorithms and/or "artificial intelligence" that can provide alternative medication suggestions based on patient's medical history, medication orders, vital signs, current medications and other important information about that patient.

In some examples, the EMRs that are created by the automated dose-response record system 100, 200, 400, 600, 800 of this disclosure can provide accurate and temporally correlated information about the relationship between any injected medication and the resulting physiologic response. This is uniquely accurate dose-response data not available in current processes or systems. In some examples, the EMRs that are created by the automated dose-response record system 100, 200, 400, 600, 800 for hundreds of thousands or even millions of patients, may be aggregated and analyzed as "big data." The "big data" from these EMRs may be used for a variety of purposes including but not limited to medical research, patient and hospital management and the development of "artificial intelligence" algorithms that can provide alternative medication suggestions. Ongoing "big data" from more and more EMRs can be used to continually improve and refine the "artificial intelligence" algorithms. These "artificial intelligence" algorithms can be used to provide automated ("self-driving" or "partially self-driving") anesthesia during surgery or automated medication delivery.

FIG. 11 illustrates a plan view of an example of healthcare provider ID badges 1184A and 1184B that can be used with the system of FIGS. 1 and 2, in accordance with at least one example. In some examples, the "chain of custody" may begin by electronically identifying the healthcare provider as the drugs are checked out from the pharmacy or Pixis medication dispenser. In some examples and as shown in FIG. 11, each provider can have a personalized RFID tag 1186, attached to their hospital ID badge 1184A. In some examples each provider can have a personalized barcode 1188, attached to their hospital ID badge 1184B for example. When the drugs are checked out, the personalized RFID tag 1186 may be read by an RFID interrogator or the personalized barcode 1188 read by a barcode reader in the pharmacy and the ID of the provider checking the drugs out may be noted in the hospital's computer and/or the processing circuitry 157, 257 (FIGS. 1 and 2) for the automated dose-response record system 100, 200, 400, 600, 800 (FIGS. 1, 2, 4, 6 and 8). The specific RFID 308 or barcode 307 (FIG. 3) identification of the injectable drug may also be recorded before the drug leaves the pharmacy and that information may be transmitted to the processing circuitry 157, 257 of the automated dose-response record system 100, 200, 400, 600, 800 of this disclosure. In some examples, instead of an RFID tag 1186 and RFID reader, other provider identification information and sensors for identifying the provider can be used, such provider identification information may include: a barcode, a QR code with the sensor being able to read such codes. In other examples, the sensor can include a retinal scanner, fingerprint reader or a facial recognition scanner that identifies the provider by personably identifiable information (e.g., provider identification information) may be used.

In some examples, when the provider arrives at the patient's bedside, the provider may be identified by their ID badge 1184 A,B. In some examples, an ID badge 1184A that has an RFID tag 1186 may be read by RFID reader 182, 282 (FIGS. 1 and 2) that can be located on the automated dose-response record system 100, 200, 400, 600, 800 or by RFID reader 438, 638, 838 (FIGS. 4, 6 and 8) located inside the automated dose-response record system 100, 200, 400, 600, 800 (FIGS. 1, 2, 4, 6 and 8). In some examples, an ID badge 1184B that has a barcode 1188 may be read by barcode reader 180, 280 that can be located on the automated dose-response record system 100, 200, 400, 600, 800. In some examples, a retinal scanner may be located on or near module 101, 201 in order to positively identify the provider by their retinal vasculature. Other scanners including but not limited to facial recognition scanning are also anticipated in order to positively identify the provider doing the injection in order to automatically document this information to an EMR or other record.

In some examples, the provider's photograph may be taken by camera 190, 290 (FIGS. 1 and 2) for further identification before allowing the injection of scheduled drugs. In some examples, the camera 190, 290 may be triggered, such as by processor 157, 257 (FIGS. 1 and 2), when a syringe e.g., 306B filled with a scheduled drug such as a narcotic is identified as it enters the injection portal 411, 611, 811 and the RFID interrogator 438, 638, 838 interrogates the RFID tag 308 (FIG. 3) or the machine vision camera 436, 636, 836 reads the barcode 307 (FIG. 3) on the syringe 306A. Non-scheduled medications may not need the added security of a photograph.

In some examples as shown in FIGS. 1 and 2, the automated dose-response record system 100, 200 of this disclosure may include a remote monitor with display 187, 287. The remote monitor may include a wired or wireless connection to the automated dose-response record system 100, 200 and may display some or all of the information shown on the electronic record display 126, 226, or other information generated by the automated dose-response record system 100. For example, the processing circuitry 157, 257 can be in electrical communication with the remote display 187, 287 and the processing circuitry 157, 257 can send instructions to the remote display 187, 287 to display the generated information.

The remote monitor may be in the next room or miles away. The remote monitor may allow remote supervision of healthcare delivery. For example, anesthesiologists frequently supervise up to four surgical anesthetics at once, each being delivered by a nurse anesthetist. In this case, the anesthesiologist carrying a wireless remote monitor 187, 287 can have real-time data on each case under their supervision. Similarly, a nurse anesthetist working in a rural hospital may be supervised by an anesthesiologist who is 50 miles away.

In some examples, the remote monitor with display 187, 287 can create a record for billing. For example, when an anesthesiologist is supervising multiple anesthetics at once, the payers may dispute the involvement in each case and refuse to pay. The remote monitor with display 187, 287 may include an RFID reader that documents the close proximity of an RFID tag on the anesthesiologist's ID badge. Any other type of proximity sensor may be used in place of the RFID tag, including but not limited to GPS location sensing. Documenting that the anesthesiologist was carrying the remote monitor with display 187, 287 throughout the time of the surgery is very good evidence that the anesthesiologist was actively participating in the care of the patient.

In some examples, the remote monitor with display 187, 287 allows long-distance medical consultation. For example, an expert at the Mayo Clinic could consult with a physician halfway around the world in Dubai, responding to real-time patient data displayed on the remote monitor with display 187, 287.

FIG. 14 illustrates a side view of an example IV fluid identification and measurement system 1430 that can be used with the systems of FIGS. 1-9, and the injection port cassette of FIG. 10. Some aspects of FIGS. 1-14 are described together, however, the examples are merely illustrative and the features can be used in any suitable combination. In some examples, the automated dose-response record system 100, 200 of this disclosure includes a system for automatically measuring and recording the administration of IV fluids. To accomplish this, as shown in FIGS. 1, 2 and 14, the automated dose-response record system 100, 200 can include an IV fluid identification and measurement system 130, 230, 1430. In some examples, the IV fluid identification and measurement system 130, 230, 1430 can be mounted onto module 101.

Alternately, the IV fluid identification and measurement system 130, 230, 1430 may be mounted to an IV pole 105 or racking system independent from the module 101. The system for automatically measuring and recording the administration of IV fluids is not limited to use in anesthesia or in the operating room, but has applicability for use throughout the hospital and other health care settings, including but not limited to the ICU, ER, wards, rehabilitation centers and long term care settings. In some examples, aspects of the IV fluid identification measurement system 130, 230, 1430 can be provided alone or together with other features of the automated dose-response record system 100, 200 including the medication identification and measurement system 128, 228.

In some examples, the IV fluid identification and measurement system 130, 230, 1430 may be configured to accommodate one or more bags of IV fluid 132, 232A,B and 1432A,B. Each bag of IV fluid can include a drip chamber 134, 234A,B and 1434A,B and IV tubing 120, 220A,B and 1420A,B. IV flow rates may be controlled with the traditional manually operated roller clamp that variably pinches the IV tubing 120, 220A,B and 1420A,B to control or even stop the flow of IV fluids. In some examples, IV flow rates may be controlled with the automatically operated electromechanical flow rate clamps 1478 that variably pinch the IV tubing 1420A to control or even stop the flow of IV fluids. The automatically operated electromechanical flow rate clamps 1478 may be controlled by the processing circuitry 157, 257, such as an electronic anesthetic record computer in module 101 or by any other suitable processor including hardware processing circuitry that is in electrical communication with the IV fluid identification and measurement system 130, 230, 1430 and/or is located within the IV fluid identification and measurement system 130, 230, 1430.

In some examples, the IV fluid identification and measurement system 130, 230, 1430 is configured to automatically measure and record the administration of IV medications and fluids. The system 130, 230 can include one or more of a barcode reader and an RFID interrogator (such as 1436A,B) for accurately and automatically identifying a fluid for IV administration. Because of the close proximity to the adjacent bags, barcode identification may be preferable in order to prevent an RFID interrogator from reading the RFID tag on a neighboring bag. In some examples, as shown in FIG. 14, one or more barcode labels 1405A,B may be applied to the IV bags 1432A,B in a location where they can be read by a sensor such as a barcode reader or machine vision camera 1436A,B, or another machine vision camera located in a suitable position to read the barcode. In some examples, a dedicated barcode reader or a machine vision camera may be positioned adjacent the barcode label 1405A,B location, specifically for reading the barcode label 1405A,B.

In some examples, the drip chamber 234A,B and 1434A,B of the IV set can be positioned adjacent the one or more machine vision cameras 1436A,B. In some examples, a standard background 1468A,B may be positioned on the opposite side of the drip chamber 1434A,B from the machine vision cameras 1436A,B. The standard background 1468A,B may be a plain background or may be an advantageous color, pattern, color design or illumination that highlights each of the falling drops, for easier identification by the processing circuitry 157, 257 (e.g., 1502, FIG. 15). The machine vision software including instructions can be stored on one or more machine-readable mediums (such as 1522 in FIG. 15) that when implemented on hardware processing circuitry (including but not limited to processing circuitry 157, 257) or in electrical communication with the system, can perform the functions described herein. An example of such electrical connection is shown by the connection of processor 1502 with mass storage 1516 in FIG. 15.

In some examples, the processing circuitry 157, 257, 1502 can be configured to look for (e.g., sense, monitor, detect) a fluid meniscus 1464A,B in the drip chamber 1434A,B. In this case "seeing" a fluid meniscus 1464A,B indicates that there is fluid in the drip chamber 1434A,B and therefore the IV bag 1432A,B is not empty, and air is not inadvertently entering the IV tubing 1420A, 1420B.

In some examples, if the IV fluid identification and measurement system 130, 230, 1430 fails to "see" a fluid meniscus 1464A,B meaning that the drip chamber 1434A,B is empty and thus the IV bag 1432A,B is empty, stop-flow clamps 1460A,B can be automatically activated. For example, processing circuitry 157, 257 can send an instruction to activate the stop-flow clamps 1460A,B to compress the IV tubing 1420A,B in order to prevent air from entering the IV tubing 1420A,B. In some examples, the empty IV bag 1432A,B condition detected by the processing circuitry 157, 257 can cause an alert to be displayed to the caregiver on the anesthetic record display 226, such as by sending an instruction to the display.

The combination of the machine vision camera 1436A,B in electrical communication with processing circuitry (e.g., 157, 257, FIGS. 1 and 2) that executes instructions stored on a machine readable medium can count the number of drops of fluid per unit of time in a drip chamber 1434A,B to calculate or to estimate the flow rate of an IV. The size of the drip chamber 1434A,B inlet orifice determines the volume of liquid in each drop. The inlet orifices of standard drip chambers are sized to create drops sizes that result in 10, 12, 15, 20, 45 and 60 drops per ml. Given a particular drop volume (size), 10 drops per ml for example, the system 130, 230, 1430 (e.g., via sensors, processing circuitry and machine readable medium) can count the number of drops falling in a known period of time and use that data to calculate or to estimate the flow rate. If these estimates were attempted by a human, they may be less accurate at higher flow rates (higher drop counts) because the drops are so fast, it can be difficult to count the drops. Eventually, at even higher flow rates the individual drops become a solid stream of fluid and the flow rate cannot be visually estimated.

In some examples, the IV fluid identification and measurement system 130, 230, 1430 is configured to look for falling drops of fluid 1462A,B within the drip chamber 1434A,B. When drops 1462A,B have been identified, the machine vision system (e.g., machine vision camera 1436A or 1436B operably coupled to processing circuitry 157, 257) may first measure the diameter of the drop 1462A,B to determine which of the standard drop sizes or volumes it is counting. Most hospitals standardize on several infusion set sizes, 10, 20 and 60 drops per cc for example. Therefore, when these limited choices of infusion set brands and sizes have been programed into the computer, the machine vision system only needs to differentiate between these choices, which is much easier than accurately measuring the diameter of the drops. Unlike the human eye, the machine vision can accurately count the falling drops even at high flow rates to calculate an IV fluid flow rate.

In some examples, the machine vision system, including the machine vision cameras 1436A,B and instructions 1524 (e.g., software) stored on a machine readable medium 1522 and implemented by hardware processing circuitry 157, 257 does not "see" falling drops 1462A,B. In this situation, either the fluid is flowing in a steady stream that is not identifiable or the fluid has stopped flowing. In some examples, these two opposite conditions can be differentiated by inserting a floating object 1466A,B (hereinafter, "float") into the drip chambers 1434A,B. In some examples, the float 1466A,B may be a ball-shaped float 1466A,B. In some examples, the float may be patterned or multi-colored to more easily identify movement or spinning of the float. In some examples, if the machine vision system cannot identify falling drops 1462A,B, it then looks to the float 1466A,B for additional information. If the float 1466A,B is not moving or spinning, the fluid flow has stopped. If the float 1466A,B is moving or spinning and drops cannot be identified, the fluid is flowing in a steady stream and the flow rate cannot be measured by machine vision. In this situation, the system can determine fluid flow using an alternate method.

In some examples, the IV fluid identification and measurement system 130, 230, 1430 may be configured to accommodate one or more bags of IV fluid 132, 232A,B, 1432A,B and each of these IV bags may be hanging from an electronic IV scale 1472A,B (e.g., a weight, a physical characteristic sensor). The electronic IV scale 1472A can measure the combined weight of the IV bag and fluid 1432A, the drip chamber 1434A and the IV tubing 1420A. The electronic IV scale 1472B can measure the weight or combined weight of one or more of the IV bag and fluid 1432B, the drip chamber 1434B, the IV tubing 1420B and a pressure infuser 1474. In both of these examples, the electronic IV scale 1472A,B can accurately measure the change in combined weight that occurs due to the drainage of the IV fluid from the IV bag 1432A,B. The change in weight per unit time can be converted to flow rates by processing circuitry 157, 257 in electrical communication with the electronic IV scale 1472A, 1472B, for example, by the processing circuitry 157, 257, 1502 and displayed on the electronic record display 126, 226.

In some examples, the calculated flow rates for each IV bag 1432A,B may also be displayed on one or more digital flow-rate displays 1476A,B mounted on the IV fluid identification and measurement system 1430. The digital flow-rate displays 1476A,B may be small LED or LCD displays that conveniently tell the operator the flow rate while they are manually adjusting the flow rate near the IV bags 1432A,B and drip chambers 1434A,B. The digital flow-rate displays 1476A,B are particularly convenient when the IV fluid identification and measurement system 130, 1430 is a free-standing entity mounted on an IV pole 105 for example while being used on the ward or ICU.

In some examples, when the falling drops 1462A,B cannot be detected and yet the floats 1466A,B are moving or spinning, the fluid is determined to be flowing in a steady stream and the flow rate cannot be measured by machine vision. In this case the electronic record computer may automatically query the change in weight per unit time as measured by the electronic IV scale 1472A,B to determine the IV flow rate. At high flow rates, the change in weight per unit time as measured by the electronic IV scale 1472A, B will most likely be more accurate than counting drops, in determining the IV flow rate.

The IV flow rate as determined by the change in weight per unit time can also be compared to the IV flow rates determined by counting drops to verify the accuracy of each method. Without interfering with or changing the healthcare providers normal or traditional IV routines, an unobtrusive machine vision camera and computer can "observe" the IV flow rates and automatically record them in the EMR.

The module or automated EMR system 101, 201 of this disclosure may capture anesthetic event data but it must be noted that the same technologies described herein for capturing anesthetic event data can be used throughout the hospital or outpatient health care system to capture and record medication administration, IV fluid administration, vital signs and patient monitor inputs, provider events and other data. Non-operating room heath care locations are included within the scope of this disclosure. While this disclosure focuses on the totality of functions offered by module 101, 201, each of the individual functions can be offered independently of module 101, 201.

The use of the term Electronic Anesthetic Record (EAR) as defined herein can include any memory such as an electronic surgical record (ESR), or an electronic medical record (EMR), and is not limited to anesthetic or surgical applications. Aspects of the modules 101,201 described herein can also be employed in recovery, hospital room and long-term care settings.

In an example, the module 201 of FIG. 2, can include a housing 299 having a lower section 299A and a tower-like upper section 299B, wherein the lower section 299A can be configured to house unrelated waste heat-producing electronic and electromechanical surgical equipment, and wherein the tower-like upper section 299B can be located on top of the lower section 299A. The module 201 can also include a cowling 299C external or internal to the housing 299 that substantially confines waste heat generated by the unrelated waste heat-producing electronic and electromechanical surgical equipment. In addition, the module 201 can include a system for monitoring the administration of one or more IV medications and fluids 228, 230. As shown in the combination of FIGS. 2, 4, 5 and 14, the system 228, 230 can include any of: a barcode 436 reader or an RFID 438 interrogator configured to identify the one or more IV medications or fluids; a machine vision digital camera 436 to capture an image of one or more of a syringe 406 or a drip chamber 1434A,B; processing circuitry 257 operably coupled to the barcode reader 436 or the RFID interrogator 438 (or the machine vision digital camera 436) to receive the identity of the one or more IV medications or fluids, the processing circuitry 257 operably coupled to the machine vision digital camera 436 to receive the captured image and determine a volume of medication administered from the syringe or fluid administered from an IV bag based on the image; and a display 226 operably coupled to the processing circuitry 257, the display 226 configured to receive instructions from the processing circuitry 257 to output the identity and determined volume of medication administered from the syringe or fluid administered from an IV bag.

"Dose-response" can be a useful medical process. Dose-response includes giving something to the patient (a medicine for example) or doing something to the patient (mechanical ventilation or surgery for example)—the "dose", and then observing the patient's "response."

Healthcare data in general is not automated. Healthcare data in general is also not granular (e.g., beat-by-beat, second-by-second, continuous) but rather very intermittent (e.g., every 15 minutes, every 4 hours, every day etc.). In general, most data in the EMR are simply data that was on the old paper record, manually entered into the EMR. There are known conventional systems including healthcare "dose events" that are automatically digitized and automatically entered into the EMR or other databases.

Manual data entry of dose events, whether they are reporting medication injections, fluid infusions or changes in the ventilator settings or any other "dose events" are laborious, distracting and universally disliked by healthcare providers. Perhaps more important is that the dose events are not accurately recorded. First, there are innocent errors in recording. Second, there are omissions that may be innocent or for lack of time or due to provider sloppiness. Finally, there is no temporal correlation between a dose event and a related response event because the dose event is most likely manually recorded minutes to hours after the dose event occurred (if it is recorded at all).

At this date, even response data generated by physiologic monitors is not recorded beat-by-beat, but rather intermittently recorded every 30 minutes or 4 hours for example—just as it was historically recorded on the paper record. The remainder of the response data must be manually entered into the record and thus suffers from the same limitations as noted above for the manually entered dose events. As a result, with current EMRs the dose and response data cannot be temporally correlated with any accuracy, vastly reducing the analytical and predictive value of the electronic database and record. The systems described herein provide a technical solution to a technical problem. Furthermore, the benefits achieved by the technical solutions of this disclosure exceed what can be accomplished by manual processes.

In some examples, the automated dose-response record system 100,200 of this disclosure includes systems and methods for constructing granular (beat-by-beat, second-by-second) anesthetic, surgical and patient records that include both "dose" events—the things that are given or done to the patient (inputs from medication injection and fluid monitors, various support equipment and machine vision "observations" for example) and "response" events (inputs from electronic physiologic monitors, various measurement devices and machine vision "observations" for example). In some examples, the automated dose-response record system 100,200 of this disclosure automatically enters both dose and response events into the electronic record. In some examples, the dose and response events of this disclosure are continually recorded, creating a much more granular record than is possible in conventional electronic records.

In some examples, the automated dose-response record system 100,200 of this disclosure automatically enters both dose and response events into the electronic record and temporally correlates the dose and response events when they are recorded. Temporally correlating the dose and response data can be accomplished by recording dose and response data in parallel, adding integrated or external time stamps to the dose and response data or any other suitable method of temporally matching the data sets.

In some examples, the automatically entered, temporally correlated dose and response events in the patient's electronic medical record (EMR) may be analyzed by artificial intelligence (AI) and/or machine learning (ML) software in the processing circuitry of the module for immediate advisory, alerts and feedback to the clinician. The patient's own data can be analyzed by AI algorithms that were derived from general medical knowledge and research or may be analyzed by AI algorithms that were derived from AI analysis of the pooled database of many patients, such as machine learning (ML), traditional mathematical analysis or a combination thereof.

In some examples, the automatically entered, temporally correlated dose and response events in the patient's electronic record may be pooled with the records of other patients in a database that can be analyzed with artificial intelligence and machine learning software stored on a memory and executed by processing circuitry. This analysis can occur at the time of temporal correlation or at a later time. This type of analysis is sometimes known as "big data." The pooled data (e.g. aggregated data, compiled data, such as collective data of a group of patients, collective data for a specific patient over different periods of time, doses, responses, medications, providers) may be stored on proprietary servers or may be stored in "the cloud." In any event, the "big data" database of this disclosure is complete and granular (compared to current healthcare databases) because it was automatically entered and at least some of the data is continually recorded. The "big data" database of this disclosure includes both dose events and response events (compared to current healthcare databases that are weighted toward response events) and the dose and response events are temporally correlated (compared to current healthcare databases). Temporal correlation can include time matching different sets of data streams.

"Big data" has been characterized by "four Vs": Volume, Velocity, Variety and Veracity. In some examples, the automated dose-response record system 100 of this disclosure addresses each of these characteristics in order to optimize the acquired data for "big data" use and analysis.

Volume—The more data you have the better it is. The automated dose-response record system 100 of this disclosure can maximize data volume by collecting data not only from the physiologic monitors but also from some or all of the OR equipment and other dose events including machine vision video observations. Velocity—The speed at which you process the data. The automated dose-response record system 100 of this disclosure can maximize data velocity by automatically recording everything which removes the human function that always slow processes down. Variety—How different is the data. The automated dose-response record system 100 of this disclosure maximizes data variety by recording most if not all data sources in the OR or other care locations, including but not limited to: physiologic monitors, equipment, medication injections, fluids and video. Veracity—How accurate is the data, the truthfulness of the data. The automated dose-response record system 100 of this disclosure maximizes data veracity by automatically recording the data without requiring human input. In some examples, the automated dose-response record system 100 of this disclosure includes Sensor Fusion, a data analytic system that monitors input data in order to reject clearly mistaken inputs such as might occur if an EKG lead comes lose for example improving the veracity of the database. In some examples, Sensor Fusion may include a threshold-controlled artifact-removal module and/or a Kalman filter.

In some examples as shown in FIG. 2, module 201 of the automated dose-response record system 200 may consolidate a wide variety of equipment used for anesthesia and surgery. Some of this equipment, including but not limited to: the physiologic monitors, the urine output monitor and the blood loss monitor, produce response event data that can be automatically recorded by the automated dose-response record system 200.

In some examples as shown in FIG. 2, module 201 of the automated dose-response record system 200 may consolidate a wide variety of equipment that produce dose event data, including but not limited to: medication identification and measurement system 228 and the IV fluid identification and measurement system 230, gas flow meters, medical equipment (e.g., 270) such as a mechanical ventilator, a pneumoperitoneum insufflator and a electrosurgical generator—dose event data that can be automatically recorded by the automated dose-response record system 200 (e.g., dose event data can be received by processing circuitry 157, 257 and stored on one or more storage devices).

The automated dose-response record system 100,200 can not only consolidates various electrical and electromechanical equipment 270 but can also consolidate the data outputs of the various equipment for easy electrical communication with the processing circuitry 157, 257. The consolidation of various types of medical equipment 270 described throughout this disclosure in, on or off of the module 201 of the automated dose-response record system 200 solves another practical obstacle currently preventing an automated dose-response record. Currently, much of the equipment mentioned above does not produce digital data that documents the equipment's operation because the various equipment manufacturers have chosen not to provide output data. The practical solution is that the vender of the automated dose-response record system 200 can require that any equipment 270 that is to be located in, on or in electrical communication with the module 201 include data outputs and the vender can also prescribe the digital format. These benefits are not provided in any conventional system.

Machine vision cameras and software are good at measuring distances, movements, sizes, looking for defects, fluid levels, precise colors and many other quality measurements of manufactured products. Machine vision cameras and software can also be "taught" through AI and ML to analyze complex and rapidly evolving scenes such as those in front of a car driving down the road. Machine vision cameras and software don't get bored or distracted.

FIG. 12 illustrates an isometric view of another example module 1201 including an automated dose-response system 1200 for generating an automated electronic anesthetic record where the module can be easily located proximate to a patient. FIG. 12 can be similar to FIG. 2, therefore, for the sake of brevity all elements may not be described in further detail. Like numbers may represent like elements. For example, the module 1201 including the automated dose-response record system 1200 for generating an automated electronic anesthetic record can include any of the features of the module 201 including automated dose-response record system 200 for generating an automated electronic anesthetic record described herein. Further for example, the IV fluid identification and measurement system 230 can be the same or similar as IV fluid identification and measurement systems 230 of FIG. 2 described herein. Likewise, an identification and measurement system 228 can be the same or similar as identification and measurement system 228 described herein. Processing circuitry 1257 and one or more storage devices 1259 can include all the features of the processing circuitry 157, 257 and the one or more storage devices 159, 259, and can include other features described herein. Unless otherwise described, elements performing related functions can be the same or similar, or are interchangeable throughout this disclosure.

In some examples as shown in FIG. 12, the automated dose-response record system 1200 of this disclosure includes systems and methods for using machine vision cameras 1297A,B and software to "observe" the patient. If the patient is in surgery, the patient's head may be the focus of the observation. In some examples, during surgery the machine vision cameras 1297A,B and software may be "looking" for (e.g., sending, detecting, monitoring) various dose events including but not limited to mask ventilation, endotracheal intubation or airway suctioning. In other words, the machine vision cameras 1297A,B can generate and send dose event data (e.g., information) to be received and analyzed by processing circuitry 1257.

In some examples, during surgery the machine vision cameras 1297A,B and software may be "looking" for (e.g., monitoring, sensing, detecting) response events including but not limited to movement, grimacing, tearing or coughing or changes in skin color or sweating. In other words, the machine vision cameras 1297A,B can generate and send response event information to be received and analyzed by processing circuitry 1257. Movement, grimacing, tearing and coughing are all signs of "light" anesthesia and that the patient may be in pain. Subtle changes in skin color from pinkish to blueish or grayish may indicate inadequate oxygenation or low perfusion. Subtle changes in skin color from pinkish to reddish may indicate hyperthermia or an allergic reaction. Sweating may indicate inadequate perfusion or hyperthermia. In any event, observing the patient is regarded by the American Society of Anesthesiologists as the most basic of all monitors. Machine vision cameras 1297A,B and software do not get bored and can be programmed to recognize subtle changes that may be missed by the human observer. Both movements and skin color changes may be subtle. The baseline color may be very difficult for the observer to remember, whereas the machine vision cameras 1297A,B and software can precisely "remember" the baseline color and recognize even subtle changes (e.g., response events) over time. In some examples, pain may be detected by facial expression analysis, such as by processing circuitry 1257 receiving response event information from the machine vision cameras 1297A,B, analyzing such response event data, and recording or displaying the response event data or other information derived from the response event data, or alerting a user via a user or other personnel via a user interface, such as the display 226 or the remote display 287.

In some examples, vital signs such as heart rate, respiration rate, blood oxygen saturation and temperature can be measured remotely via camera-based methods. Vital signs can be extracted from the optical detection of blood-induced skin color variations—remote photoplethysmography (rPPG). In some examples, this technique works best using visible light and Red Green Blue (RBG) cameras. However, it has also been shown to work using near-infrared light (NIR) and NIR cameras. Just like pulse oximetry, a well-known technology for detecting pulse and blood oxygen saturation, rPPG relies on the varying absorption of different wavelengths of light caused by blood volume changes and the oxygen saturation of the blood in the small blood vessels beneath the skin. Unlike pulse oximetry that needs to be in contact with the skin, rPPG enables contactless monitoring of human cardiac activities by detecting the pulse-induced subtle color changes on the human skin surface using a regular RGB camera.

In some examples, this disclosure anticipates automating the remote photoplethysmography using techniques such as, but not limited to, region of interest (RoI) detection and full video pulse extraction (FVP). In some examples, this disclosure also anticipates using a combination of visible light and near-infrared light wavelengths to detect different parameters. In some examples, additional measurements are anticipated using the rPPG technology including but not limited to measuring blood glucose and hemoglobin levels.

FIG. 13 illustrates an isometric view of yet another example module 1301 including a system 1300 for generating an automated electronic anesthetic record located proximate to a patient. FIG. 13 can be similar to FIG. 1, therefore, for the sake of brevity all elements may not be described in further detail. Like numbers may represent like elements. For example, the module 1301 including the automated dose-response record system 1300 for generating an automated electronic anesthetic record can include any of the features of the modules 101, 201, 1201 including automated dose-response record system 100, 200, 1200 for generating an automated electronic anesthetic record described herein. Further for example, the IV fluid identification and measurement system 130 can be the same or similar as IV fluid identification and measurement systems 130 described herein. Likewise, an identification and measurement system 128 can be the same or similar as identification and measurement system 128 described herein. Processing circuitry 1357 and one or more storage devices 1359 can include all the features of the processing circuitry 157, 257, 1257, 1502 and the one or more storage devices 159, 259, 1259, 1504, 1506, 1516 and can include other features described herein. Unless otherwise described, elements performing related functions can be the same or similar, or are interchangeable throughout this disclosure.

In some examples as shown in FIG. 13, if the patient is on the ward, in the nursing home or other long-term care facility or at home, the whole patient may be the focus of the observation. In some examples, if the patient is on the ward, in the nursing home or other long-term care facility or at home the machine vision cameras 1397 and software may be "looking" for (e.g., sensing, monitoring, detecting) dose events including but not limited to repositioning the patient or suctioning the airway or assisting the patient out of bed or any other nursing procedure.

In some examples, if the patient is on the ward, in the nursing home or other long-term care facility or at home, the machine vision cameras 1397 and software may be "looking" (e.g., sensing, monitoring, detecting) for response events including but not limited to restlessness or getting out of bed without assistance or coughing or changes in the breathing pattern. Recent research has shown that machine vision cameras 1397 and software with AI can recognize moods with reasonable accuracy. The patient's mood could be an important response event that can be recorded.

Figure 24:
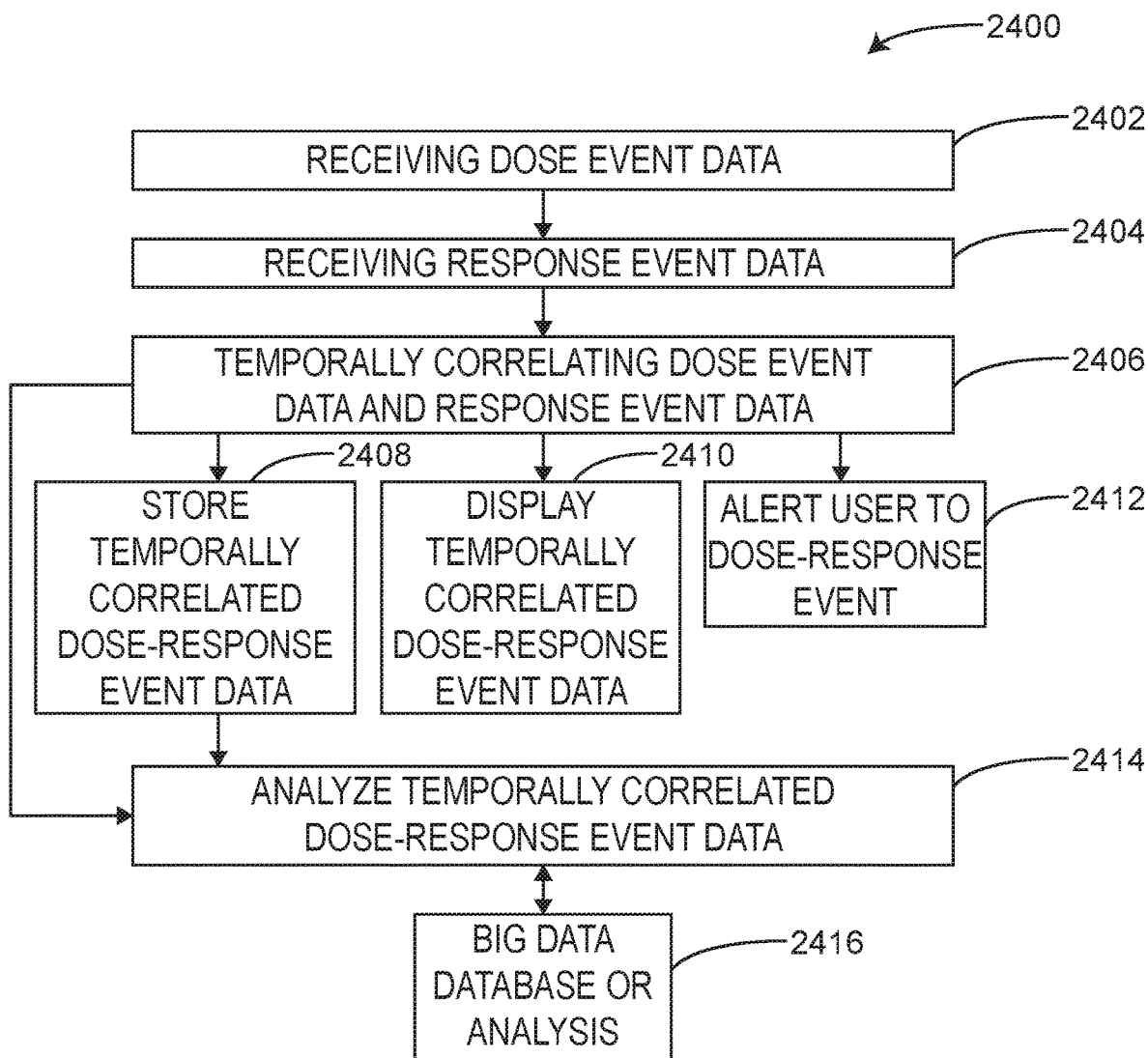
FIG. 24 is a flow chart illustrating a technique 2400 for temporally correlating and analyzing dose-response events, in accordance with at least one example of this disclosure.

As shown in technique 2400 of FIG. 24, various operations can be performed by the dose-response systems 100, 200, 1200, 1300 and subsystems disclosed herein. While the technique 2400 can be performed by the dose-response systems 100, 200, 1200, 1300, the technique 2400 can also be performed by other systems, and the systems 100, 200, 1200, 1300 can perform other techniques In an example, a dose-response system can perform technique 2400 using processing circuitry and one or more storage devices including a memory. The memory can have instructions stored thereon, which when executed by the processing circuitry cause the processing circuitry to perform the operations. For example, operation 2402 can include receiving dose event data (e.g., a dose event, dose information) from one or more dose sensors. Operation 2404 can include receiving response event data (e.g., response event, response information) from one or more response sensors. The dose event data can include information corresponding to a dose provided to the patient, and the response event data can include data corresponding to a response of the patient. Operation 2406 can include temporally correlating the dose event data and the response event data. Operation 2408 can include saving the temporally correlated dose-response event data to at least one of the one or more storage devices, such as storage device 1516 of FIG. 15. Temporally correlating dose-response event data can include continuously temporally correlating the dose-response event data, such as in a processor-based timer, in a beat-by-beat, second-by-second type manner, as opposed to the non-continuous, extended intervals and less accurate methods of traditional medical practice. In some examples, temporally correlating the dose-response event data includes temporally correlating the dose-response event data, such as in a range between about every 0.01 seconds to 15 minutes. In some examples, it may be preferable to temporally correlate in a range between every 0.1 seconds to 5 minutes. It may be more preferable to temporally correlate in a range between every 0.5 second to 1 minute. It may be even more preferable to correlate in a range between every 1 second and 30 seconds, to maximize accuracy while not oversampling the rate of doses and responses, however, any suitable temporal correlation may be used to facilitate accurate, safe and meaningful correlation where a direct, time-based relationship between the dose and the response is captured. In some examples, the dose response event data can be temporally correlated substantially continuously, such as is possible in processor-based systems. Continuous can include data collection that is persistent, consistent and without the errors of scheduled manual entry, result in producing a continuous, consistent data stream.

In some examples, operation 2410 can include displaying information corresponding to the dose-response event data. In operation 2412, if the processing circuitry detects a concerning response, the processing circuitry can cause alerting a user to the response. Operation 2414 can include analyzing the temporally correlated dose-response event data. In some examples, operation 2414 can include aggregating the temporally correlated dose-response event data with temporally correlated dose-response event data collected from other patients. In some examples, operation 2414 can include aggregating the temporally correlated dose-response event data with temporally correlated dose-response information collected from the same patient over a different period of time. Comparing data from the same patient may allow a provider to detect when a patient develops a tolerance to a drug, such as a pain killer. In an example, if the rate of grimacing by the patient increases or they start to grimace sooner (e.g., response) after being given a pain medication (dose), as the pain medication is given over different days, weeks and months. Operation 2414 can also use or facilitate ML. Operation 2416 can include "big data" analysis including AI or ML. The one or more storage devices, which can include an electronic record or database, can be configured to be accessed by artificial intelligence or machine learning algorithms to retrieve the temporally correlated dose-response event and compare the temporally correlated dose-response event to other temporally correlated dose-response events across a population of patients and output big data correlation insights to at least one storage device or display. Data can pass back and forth between operations 2408, operation 2414 and operation 2416 to analyze and understand dose-response events across a population of patients. In some examples, traditional mathematical analysis can be used with or instead of AI or ML, including evaluating an average, median, range, mode, etc. . . .

In technique 2400, the dose information can include data/events generated by one or more of: an RFID interrogator, a barcode reader, a QR reader, a machine vision digital camera, any combination thereof, or any other suitable sensor. The response information can include data/events generated by a machine digital camera or any other suitable sensor. The response information can include an image of one or more movements, secretions or skin color changes, and the processing circuitry can be configured to identify changes in the response information. In some examples the processing circuitry can use machine learning to identify changes in the response information. In some examples, the response information includes physiologic data generated by a physiologic monitor (e.g., 270, urine output collection system 242). For example, the physiologic data can include at least one of: electrocardiogram, pulse oximetry, blood pressure, temperature, end-tidal $CO_2$, expired gases, respiratory rate, hemoglobin, hematocrit, cardiac output, central venous pressure, pulmonary artery pressure, brain activity monitor, sedation monitor, urine output, blood loss, blood electrolytes, blood glucose, blood coagulability, train-of-four relaxation monitor data, IV extravasation monitor data and body weight, and any combination thereof or other suitable physiologic data.

Implementation of any of the techniques described herein may be done in various ways. For example, these techniques may implemented in hardware, software, or a combination thereof. For a hardware implementation, the processing units may be implemented within on or more application specific integrated circuits (ASICs), digital signal processors (DSPs), digital signal processing devices (DSPDs), programmable logic devices (PLDs), field programmable gate arrays (FPGAs),processors, controllers, micro-controllers, microprocessors, other electronic units designed to perform the functions described above, and/or a combination thereof.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine-readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the techniques may be implemented with modules (e.g., procedures, functions, and so on) that perform the functions described herein. Any machine-readable medium tangibly embodying instructions may be used in implementing the techniques described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

There are two common modes for ML: supervised ML and unsupervised ML. Supervised ML uses prior knowledge (e.g., examples that correlate inputs to outputs or outcomes) to learn the relationships between the inputs and the outputs. The goal of supervised ML is to learn a function that, given some training data, best approximates the relationship between the training inputs and outputs so that the ML model can implement the same relationships when given inputs to generate the corresponding outputs. Unsupervised ML is the training of an ML algorithm using information that is neither classified nor labeled, and allowing the algorithm to act on that information without guidance. Unsupervised ML is useful in exploratory analysis because it can automatically identify structure in data. Either of supervised ML or unsupervised ML can be used to train the systems described herein to correlate information from one or more sensors, such as a machine vision digital camera as having a particular meaning. For example, either of supervised or unsupervised ML can be used to train the systems to correlate facial expressions with response events. The system can be trained to "read" a particular patient, or a group of patients that may or may not include the particular patient being monitored.

Common tasks for supervised ML are classification problems and regression problems. Classification problems, also referred to as categorization problems, aim at classifying items into one of several category values (for example, is this object an apple or an orange?). Regression algorithms aim at quantifying some items (for example, by providing a score to the value of some input). Some examples of commonly used supervised-ML algorithms are Logistic Regression (LR), Naive-Bayes, Random Forest (RF), neural networks (NN), deep neural networks (DNN), matrix factorization, and Support Vector Machines (SVM).

Some common tasks for unsupervised ML include clustering, representation learning, and density estimation. Some examples of commonly used unsupervised-ML algorithms are K-means clustering, principal component analysis, and autoencoders.

FIG. 15 illustrates an example electronic and/or electromechanical system 1500 of a medical system in accordance with some examples described herein. The system 1500 will be described with respect to the medical system 20, but can include any of the features described herein to perform any of the methods or techniques described herein, for example, by using the processor 1502. The processor can include processing circuitry 157 or 257 of FIGS. 1 and 2. In some examples, the processing circuitry 1502 can include but is not limited to, electronic circuits, a control module processing circuitry and/or a processor. The processing circuitry may be in communication with one or more memory and one or more storage devices. A single processor can coordinate and control multiple, or even all the aspects of the system 1500 (e.g., of modules 101, 201), or multiple processors can control all the aspects of the system 1500. In some examples the storage device 1516 or memory 1504, 1506, 1516 can include at least a portion of the patient's anesthetic record saved thereon. The system 1500 can also include any of the circuitry and electronic and/or electromechanical components described herein, including but not limited to, any of the sensor(s) described herein (e.g., sensors 1521), such as but not limited to, RFID barcode or QR codes sensors, machine vision cameras, retinal scanners, facial recognition scanners, fingerprint readers, actuators and position sensors described herein. Other sensors 1521 can include medical equipment 270 such as a physiologic monitor or machine vision digital camera (1297A,1297B, 1397 of FIGS. 12 and 13) configured to take images of a patient 202 lying in a bed. The system 1500 may also include or interface with accessories or other features such as any of: a remote display or wireless tablet (e.g., 287, FIG. 2), as well as any of the other systems described herein.

The processing circuitry 1502 can receive information from the various sensors described herein, make various determinations based on the information from the sensors, output the information or determinations from the information for output on the display or wireless tablet, output instructions to provide an alert or an alarm, power various components, actuate actuators such as clamps and flow managing devices, etc., or alert another system or user, as described herein. For the sake of brevity, select systems and combinations are described in further detail above and in the example sets provided in the Notes and Various Examples section below. Other embodiments are possible and within the scope of this disclosure.

Further, FIG. 15 illustrates generally an example of a block diagram of a machine (e.g., of module 101, 201) upon which any one or more of the techniques (e.g., methodologies) discussed herein may be performed in accordance with some embodiments. In alternative embodiments, the machine 1500 may operate as a standalone device or may be connected (e.g., networked) to other machines. In a networked deployment, the machine 1500 may operate in the capacity of a server machine, a client machine, or both in server-client network environments. The machine 1500, or portions thereof may include a personal computer (PC), a tablet PC, a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the execution units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 1500 may include a hardware processor 1502 (e.g., processing circuitry 157, 257, a central processing unit (CPU), a graphics processing unit (GPU), a hardware processor core, or any combination thereof), a main memory 1504 and a static memory 1506, some or all of which may communicate with each other via an interlink (e.g., bus) 1508. The machine 1500 may further include a display unit 1510, an alphanumeric input device 1512 (e.g., a keyboard), and a user interface (UI) navigation device 1514 (e.g., a mouse). In an example, the display device 1510, an input device such as an alphanumeric input device 1512 and UI navigation device 1514 may be a touch screen display. The display unit 1510 may include goggles, glasses, or other AR or VR display components. For example, the display unit may be worn on a head of a user and may provide a heads-up-display to the user. The alphanumeric input device 1512 may include a virtual keyboard (e.g., a keyboard displayed virtually in a VR or AR setting.

The machine 1500 may additionally include a storage device (e.g., drive unit) 1516, a signal generation device 1518 (e.g., a speaker), a network interface device 1520, and one or more sensors 1521, such as a global positioning system (GPS) sensor, compass, accelerometer, or other sensor. The machine 1500 may include an output controller 1528, such as a serial (e.g., universal serial bus (USB), parallel, or other wired or wireless (e.g., infrared (IR), near field communication (NFC), etc.) connection to communicate or control one or more peripheral devices or actuators of the system. Peripheral devices can include but are not limited to any displays, controllers or memories in electrical communication with the system, and actuators can include but are not limited to: one or more stop-flow clamps 1060A,B (FIG. 10) and one or more flow rate clamps 1478 (FIG. 14) of the system.

The storage device 1516 may include a machine readable medium 1522 that is non-transitory on which is stored one or more sets of data structures or instructions 1524 (e.g., software) embodying or utilized by any one or more of the techniques or functions described herein. The instructions 1524 may also reside, completely or at least partially, within the main memory 1504, within static memory 1506, or within the hardware processor 1502 during execution thereof by the machine 1500. In an example, one or any combination of the hardware processor 1502, the main memory 1504, the static memory 1506, or the storage device 1516 may constitute machine readable media that may be non-transitory.

While the machine readable medium 1522 is illustrated as a single medium, the term "machine readable medium" may include a single medium or multiple media (e.g., a centralized or distributed database, or associated caches and servers) configured to store the one or more instructions 1524.

The term "machine readable medium" may include any medium that is capable of storing, encoding, or carrying instructions for execution by the machine 1500 and that cause the machine 1500 to perform any one or more of the techniques of the present disclosure, or that is capable of storing, encoding or carrying data structures used by or associated with such instructions. Non-limiting machine-readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1524 may further be transmitted or received over a communications network 1526 using a transmission medium via the network interface device 1520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1520 may include one or more physical jacks (e.g., Ethernet, coaxial, or phone jacks) or one or more antennas to connect to the communications network 1526. In an example, the network interface device 1520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1500, and includes digital or analog communications signals or other intangible medium to facilitate communication of such software.

Method examples described herein may be machine or computer-implemented at least in part. Some examples may include a computer-readable medium or machine-readable medium encoded with instructions operable to configure an electronic device to perform methods as described in the examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

Some of the benefits of the automated dose-response record systems 100, 200, 1200, 1300 and the subsystems described throughout this disclosure, and including the machine 1500, can include features to help with monitoring medication, fluid and anesthesia delivery, as well as documenting medication, fluid and anesthesia delivery, as well as other functions. In general, doctors and nurses are not interested in replacing themselves and their jobs with automated drug delivery or automated anesthesia systems. However, there is great interest in automated record keeping. Virtually all healthcare providers would prefer the "old" paper record and a pen to the "new" computer records. Filling out the electronic medical record (EMR) using a computer keyboard, mouse and various menus is widely viewed as a slow, cumbersome and distracting process. The challenge with automated record keeping is automating the data input that documents the numerous activities, anesthesia related events, fluid, gas and medication administration, ventilator settings, pressure off-loading effectiveness, as well as outputs such as blood loss and urine output, that constitute an anesthetic experience.

A challenge in implementing the automated dose-response record system and fluids 100, 200, 1200, 1300 with an automated electronic anesthetic record (EAR) or electronic medical record (EMR) is to force as little change in the caregiver's routine as possible onto the clinicians using this system. Medical personnel tend to be creatures of habit and tradition and they generally do not like change. For example, IV medications are traditionally administered from a syringe and the dose is determined by the caregiver observing the plunger moving relative to a scale printed on the syringe. Maintaining this general technique of drug administration may have the highest probability of acceptance by healthcare users who are typically slow to embrace changes in their routine.

Further with regard to benefits of the modules, systems and machines described herein, the automated dose-response record system 200 of module 201 can generate an automated electronic medical record (EMR) with the module 201 locatable proximate the patient 202. The module 201 can be a module for housing unrelated electronic and electromechanical surgical equipment. The module 201 need not necessarily be configured to house unrelated electronic and electromechanical surgical equipment in all examples, and other modules can include the system for generating an automated EMR.

The module 201 can be an automated EMR system that can include one or more systems (e.g., 200, 228, 230) configured to measure (e.g., monitor) and record one or more of functions involved in a surgical anesthetic environment, and can include life support functions. The one or more systems 228, 230 can measure and record data automatically. However, in some examples, a user may initiate any of the systems described herein to measure and/or record data. These various measurements may be electronically recorded (such as on mass storage 1516 (FIG. 15) and displayed on the electronic anesthetic record display 226 (e.g., display device 1510, FIG. 15). Inputs to the automated EMR system may be managed by the anesthetic record input component 224 (e.g., input device 1512; FIG. 15). The anesthetic record input component 224 (e.g., input device 1512; FIG. 15) can include a touch-screen display 226 that organizes all of the inputs to the EMR into easily accessed and utilized information. In some examples, and as shown in FIG. 2, the identification and measurement system 228 of this disclosure may be located proximate the patient 202. The control displays for the identification and measurement system 228 may include a dedicated display proximate the identification and measurement system 228 or may be shared space on the anesthetic record input component 224 or display 226. In these locations, the information and controls of the identification and measurement system 228 can be viewed by the anesthesiologist or other user, in a single field of vision with the patient and surgical field.

Example methods of employing the systems, modules and machines disclosed herein are described throughout this disclosure and in the methods of FIGS. 16-21 which are illustrative in nature. Other methods described herein may also be performed by the systems, modules and machines described herein, and the systems modules and machines described herein may be used to perform other methods.

Figure 16:
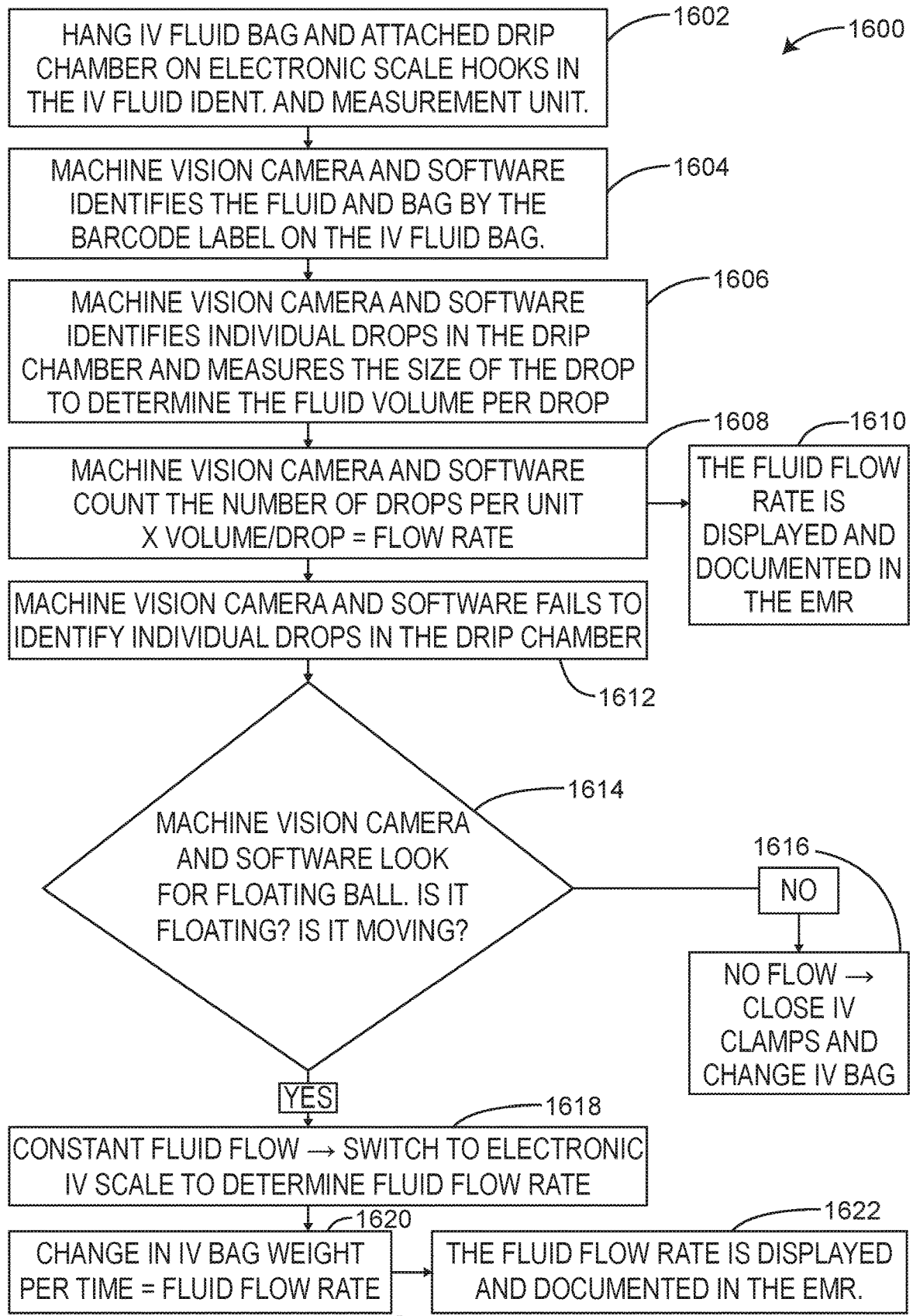
FIG. 16 is a flow chart illustrating a technique of IV fluid identification and measurement, in accordance with at least one example of this disclosure.
Figure 17:
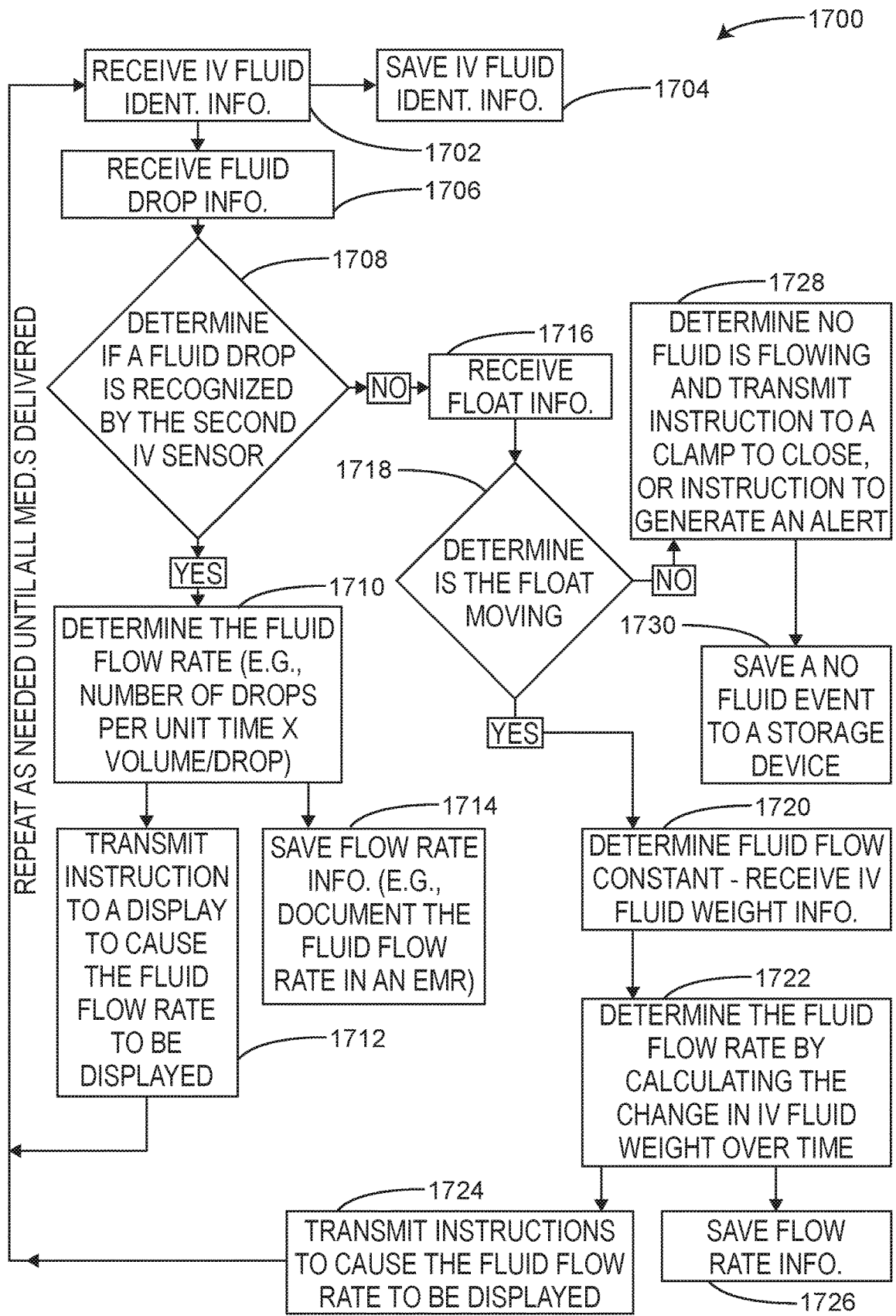
FIG. 17 is a second flow chart illustrating the technique of IV fluid identification and measurement, in accordance with at least one example of this disclosure.
Figure 18:
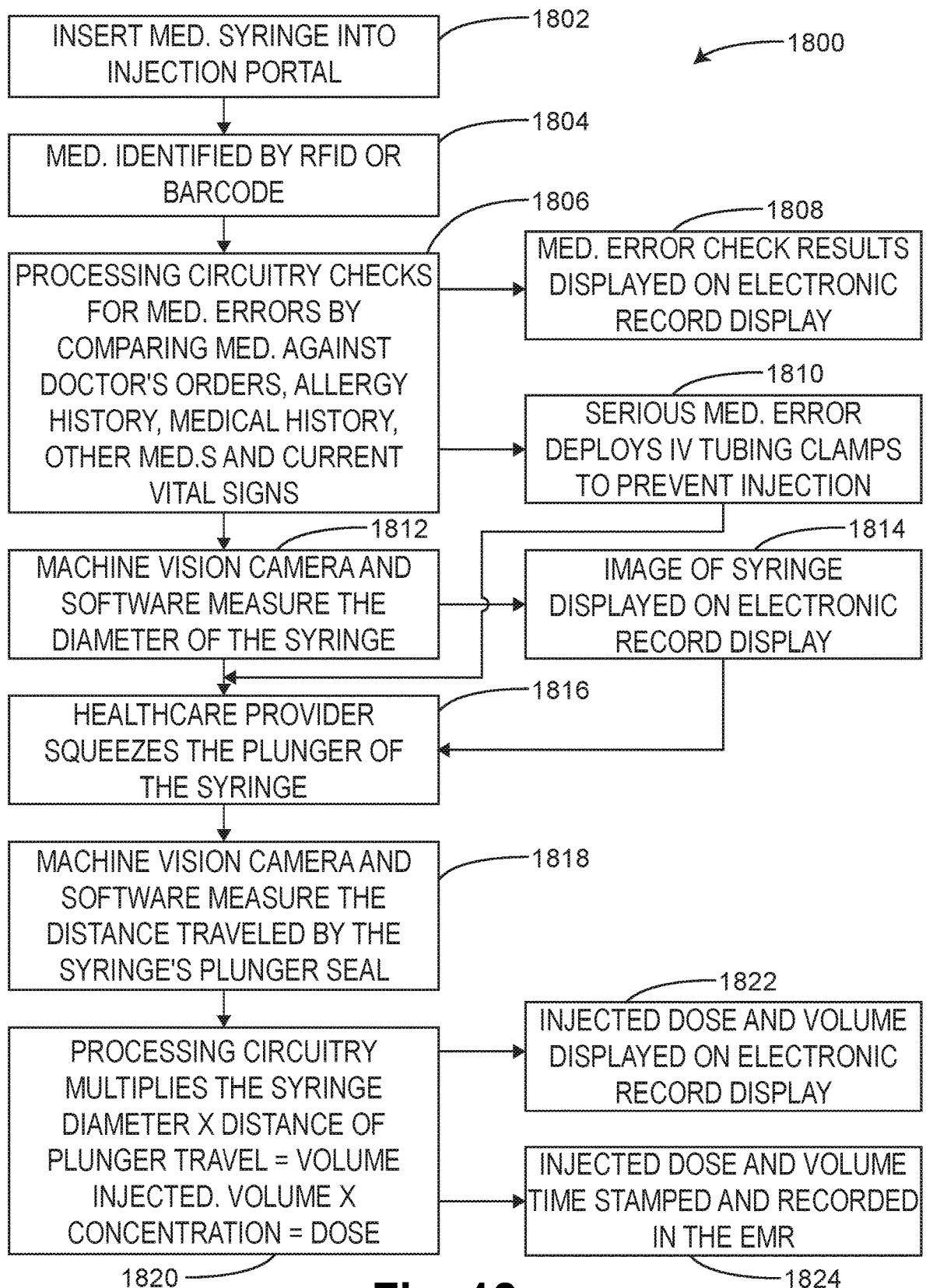
FIG. 18 is a flow chart illustrating a technique of medication identification and measurement, in accordance with at least one example of this disclosure.

FIGS. 16-18 show flow charts illustrating techniques for identification, measurement, monitoring, security and safety related to medications and/or IV fluids. The methods may be used with the systems, sub-systems and modules of FIGS. 1-15 (e.g., 101, 201, 1500), but may also be used with other systems. Likewise, the systems, subsystems of modules of FIGS. 1-15 may also be used with other methods. The techniques 1600, 1700, 1800, 1900, 2000, 2100, 2300 can be performed by at least one non-transitory machine-readable medium (e.g., computer readable) including instructions for operation of the systems described herein. Some steps of techniques may be performed by a provider. The systems can include processing circuitry (e.g., 157, 257, 1500, including one or more processors, processing circuitry hardware) for executing the instructions. The instructions, when executed by the processing circuitry can cause the processing circuitry to perform operations described in FIGS. 16-21 and 23, and as described in the examples throughout this disclosure.

FIG. 16 is a flow chart illustrating an example technique 1600 of IV fluid identification and measurement. To start the technique, in operation 1602 a provider hangs an IV fluid bag and attached drip chamber on electronic scale hooks in an IV fluid identification and measurement unit (e.g., FIG. 14). In operation 1604, a machine vision camera and software can identify the fluid and bag by the barcode label on the IV fluid bag. In operation 1606, the machine vision camera and software can identify the individual drops in the drip chamber and measure the size of the drop to determine the fluid volume per drop and count the number of drops per unit time. In operation 1608 the machine vision camera and software can calculate the flow rate by multiplying the number of drops per unit time by the volume/drop. In operation 1610, the fluid flow rate is displayed and document in the EMR.

In operation 1612, if the machine vision camera and software fails to identify individual drops in the drip chamber, in operation 1614 the machine vision camera and software can look for a floating ball (e.g., float) that is located in the drip chamber to determine if the ball is floating and if the ball is moving. In operation 1616, when the ball is not floating and/or moving, IV clamps are closed and the provider can change the empty IV bag if necessary. In operation 1618, if the machine vision camera and software can determine that the ball is floating and moving, the system determines that the fluid flow is so fast that the fluid flow is constant or continuous such that individual drops cannot be measured. In operation 1618, because individual drops cannot be determined, the system switches to measuring the fluid flow rate using an electronic IV scale (FIG. 14) to determine the fluid flow rate. In operation 1620, the fluid flow rate can be determined by monitoring the change in IV bag weight per time. In operation 1622, the fluid flow rate can be displayed and documented in the EMR.

FIG. 17 is a second flow chart illustrating a technique 1700 including aspects of the technique 1600 of IV fluid identification and measurement from the perspective of processing circuitry (e.g., 257, FIG. 2; 1502, FIG. 15). The technique 1700 may include an operation 1702 to receive IV fluid identification information from a first IV sensor (e.g., one or more sensors), such as an RFID or barcode reader to identify the fluid or other characteristics of an IV fluid bag as described herein. Operation 1704 can include saving the IV identification information to a storage device (e.g., one or more storage devices, memory, EMR). Operation 1706 can include to receive fluid drop information from a second IV sensor, such as a machine vision camera that detects, senses and measures an individual drop in a drip chamber to determine a fluid volume per drop and measure the number of drops per unit of time. While the illustrative example of FIG. 17 includes the first IV sensor and the second IV sensor, in some examples the first IV sensor and the second IV sensor can be the same sensor or same one or more sensors. Operation 1708 can include to determine if a fluid drop was recognized by the second IV sensor. If in operation 1708 it is determined that a fluid drop was recognized, operation 1710 can include determining a fluid flow rate, such as by calculating the flow rate by multiplying the number of drops per unit time by the volume per drop. In some examples, the volume per drop is measured, while in other examples the volume per drop may be input by a user, or can be a value retrieved from a memory. Operation 1712 can include transmitting instructions to a display to cause a fluid flow rate to be displayed. Operation 1714 can include saving flow rate information to the storage device to document the fluid flow rate in the EMR. Any time a change is input or detected in the system, updated flow rate information can be displayed and saved.

If in operation 1708 it is determined that a fluid drop was not recognized, operation 1716 can include receiving float information from the second IV sensor or another IV sensor. The float information can include information about a float in the drip chamber including is the float still (e.g., not moving), moving, or is movement of the float slowing down. Operation 1718 can include determining if the float is moving. If the float is moving, Operation 1720 can include determining the fluid flow is constant. In such a scenario, the fluid is flowing but the fluid is flowing so quickly that individual drops of fluid cannot be distinguished because the fluid is flowing as a steady stream. Operation 1720 can further include determining the fluid flow rate by receiving IV bag physical characteristic information from a physical characteristic sensor, such as a weight sensor. The physical characteristic information can include weight information from the weight sensor (e.g., scale). Operation 1722 can include determining the fluid flow rate by calculating the change in IV bag weight over a period of time. Operation 1726 can include saving flow rate information based on the determined flow rate in operation 1722. Operation 1724 can include transmitting instructions to cause the fluid flow rate to be displayed on a display (e.g., outputting the fluid flow rate to be displayed on a display). In other examples, instead of weight information, the physical characteristic information can include a position of the IV bag that changes as a result of a change in weight, without the physical characteristic data corresponding directly to a weight measurement. Other physical characteristics and other physical characteristic sensors configured to monitor IV fluid delivery may be provided such that an automated, or at least partially automated EMR system is enabled. Technique 1700 can be repeated as needed until all medications are delivered.

If in operation 1718 it is determined that the float is not moving, operation 1728 can include determining that no fluid is flowing from the IV bag and transmitting one or more of: an instruction an actuator such as a clamp, to cause the actuator to inhibit fluid flow to the patient (e.g., close the clamp onto IV tubing to prevent flow); and transmit and instruction to an indicator (e.g., display, audible, tactile indicator) to cause an alert to be generated. Operation 1730 can include saving a no fluid event to the storage device or displaying a no fluid event on a display.

FIG. 18 is a flow chart illustrating an example technique 1800 of medication identification and measurement. In operation 1802 a provider inserts a medication syringe into an injection portal (e.g., 411, FIG. 4). In operation 1804 the medication can be identified by a sensor such as by at least one of the RFID, barcode or QR sensors described herein. In operation 1806 processing circuitry checks for medication errors by comparing the medication against one or more of: a doctor's orders, allergy history, medical history, other medications and current vital signs. In operation 1808, the results of the medication error check can be displayed on an electronic record display. The results can indicate no error, the presence of an error, specific details about the error, or present a link to access information including additional details about the error. In operation 1810, if a serious medication error is recognized, the error deploys (e.g., causes actuation of) IV tubing clamps (e.g., 1060A, 1060B of FIG. 10) to prevent injection of the medication.

If in operation 1812, such as when no errors are determined, the machine vision camera and software can measure the diameter of the syringe. In operation 1814, an image of, or representation of the image of the syringe, is displayed on the electronic record display. In operation 1816 the provider squeezes the plunger of the syringe. In operation 1818, the machine vision camera and software measure the distance traveled by the syringe's plunger seal (e.g., 548, FIG. 5). In operation 1820 the processing circuitry calculates the volume injected by multiplying the syringe diameter times the distance of plunger travel. The processing circuitry can also calculate the dose by multiplying the volume injected by the concentration of the medication. In operation 1822 the injected dose and volume are displayed on the electronic record display. In operation 1824 the injected dose and volume are time stamped and recorded in the electronic medical record.

Figure 19:
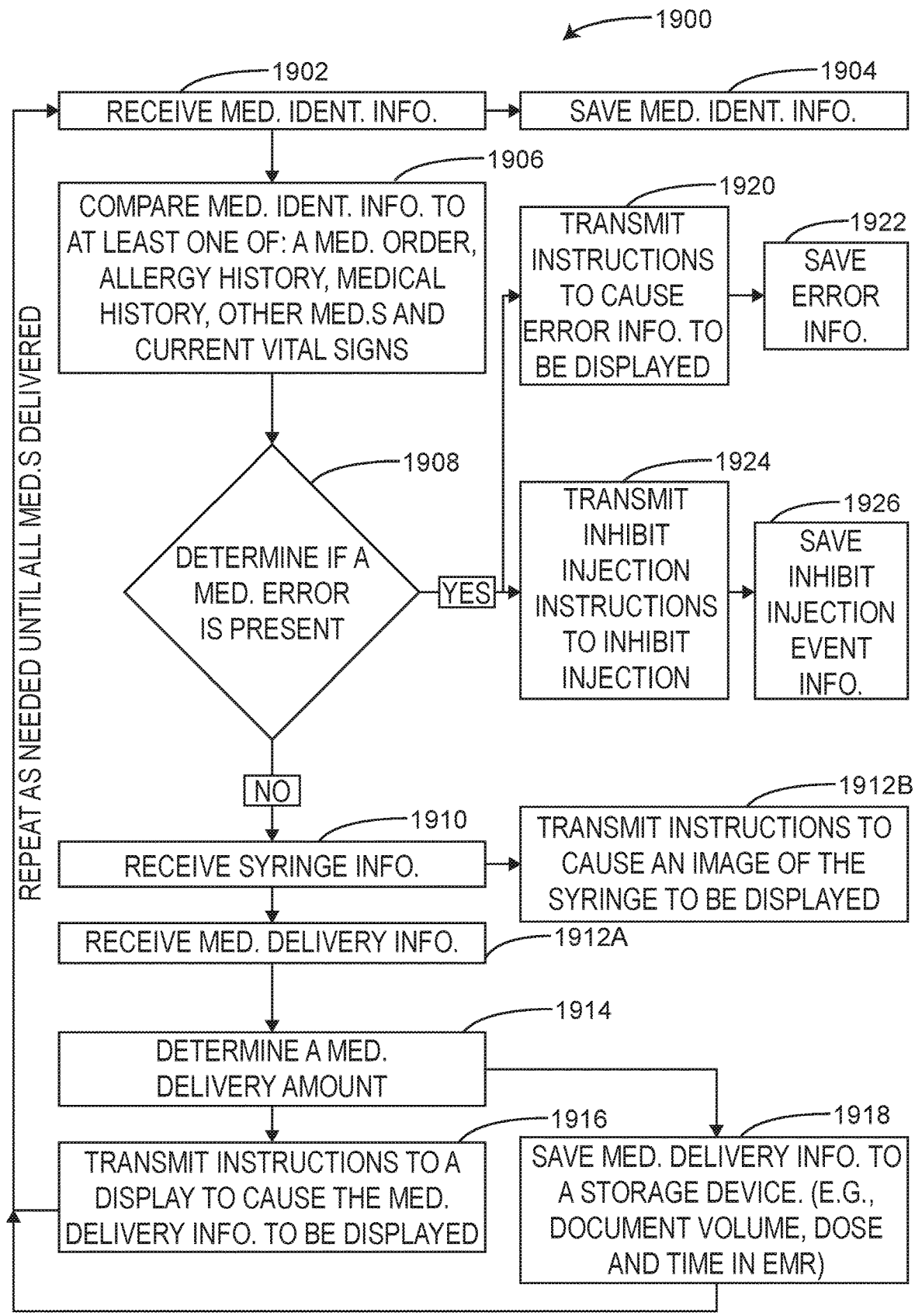
FIG. 19 is a second flow chart illustrating a technique of medication identification and measurement, in accordance with at least one example of this disclosure.

FIG. 19 is a second flow chart illustrating a technique 1900 including aspects of the technique 1800 of medication identification and measurement from the perspective of processing circuitry (e.g., 157, FIG. 1; 257, FIG. 2; 1502, FIG. 15).

Technique 1900 can include an operation 1902 to receive medication identification information such as medication type, concentration, brand, lot number or amount, from a first medication sensor (e.g., RFID, barcode or QR reader). Operation 1904 can include saving medication identification information to a storage device (e.g., one or more storage devices, memory). Operation 1906 can include comparing medication identification information to at least one of a medication order, allergy history, medical history, other medications ordered for the patient, and vital signs (e.g., previously obtained vital signs or current vital signs of the patient via continuous monitoring). Operation 1908 can include determining if a medication error is present. Operation 1910 can include receiving syringe information from a second medication sensor (e.g., a sensor configured to measure diameter, such as a machine vision camera). Operation 1912A can include receiving medication delivery information from the second medication sensor or another medication sensor. In some examples, the medication delivery information can include a distance of a syringe plunger travel.

Operation 1912B can include transmitting instructions to a display to cause an image of the syringe (e.g., actual image or representation of the syringe) to be displayed. A representation of the syringe can include an image communicating information about the syringe that is not an image of the actual syringe or can be a modified image of the syringe, such as to highlight or point out aspects of the syringe or medication within the syringe Using the medication delivery information obtained in operation 1912A, operation 1914 can include determining a medication delivery amount. Operation 1916 can include transmitting instructions to a display (e.g., display 226, FIG. 2) to cause the medication delivery information or medication delivery amount to be displayed.

If in operation 1908 it is determined that a medication error is present, operation 1920 can include transmitting instructions including error information to the display or another display to cause the error information to be displayed. In some examples, any of the instructions described herein that are sent to the display can be sent to one or more displays. Such displays can be located locally or remotely (e.g., in a different part of a room, in a separate room, in another building, in another state, in another country), to alert multiple providers. For example, a provider such as a nurse anesthetist located adjacent to the patient can be alerted to and provided with the information via display 226. In addition, a second provider, such as an anesthesiologist supporting the nurse anesthetist, and who may be supporting other nurse anesthetists working in different rooms, can also be alerted on a display of a mobile device, which may prompt them to check in with and potentially assist the nurse anesthetist. This concept can be applied outside the operating room to manage medication delivered by providers working in different rooms of a hospital or other care center, while a second provider such as a nurse manager, nurse practitioner, pharmacist or doctor oversees the work of the first provider. In operation 1922 the error information can be saved to one or more storage devices (e.g., 259, FIG. 2; 1516, FIG. 15).

Also in response to determining that a medication error has occurred in operation 1908, operation 1924 can include transmitting instructions to an actuator such as an IV tubing clamp to inhibit (e.g., prevent, reduce, limit) injection. In some examples, the actuator can reduce or limit the amount of the injection to a specified amount rather than completely inhibiting or preventing administration of the medication. Operation 1926 can include saving an inhibit injection event information to a storage device, such as any of the one or more storage devices (e.g., 259, FIG. 2; 1516, FIG. 15). The inhibit injection event information can include information such as the time of the event and the action taken to inhibit injection and how much the injection was inhibited (e.g., partially inhibited, completely inhibited, or amount of medication inhibited from injection).

If in operation 1908 it is determined that a medication error has not occurred, operation 1910 can include receiving syringe information including a syringe diameter from a sensor such as a machine vision camera. In some examples, the sensor can be the first medication sensor or can be a second medication sensor. Operation 1912A can include receiving medication delivery information from a sensor such as from the first medication sensor, the second medication sensor or another sensor. The medication delivery information can include a distance of plunger travel relative to a syringe body. Operation 1912B can include transmitting instructions to one or more displays such as, display 226, FIG. 2, to cause an image of the syringe or representation of the syringe to be displayed.

Operation 1914 can include determining a medication delivery amount, such as a volume or dose injected. For example, the volume injected can be calculated by multiplying the syringe diameter by the distance of plunger travel. The dose injected can be calculated by multiplying the volume injected by the concentration of the medication.

Operation 1916 can include transmitting instructions to the one or more displays to cause the medication delivery information to be displayed. Operation 1918 can include saving medication delivery information to the storage device (e.g., EMR). In some examples, the medication delivery information can include, but is not limited to, volume, dose, time of the injection, or time period of the injection.

Figure 20:
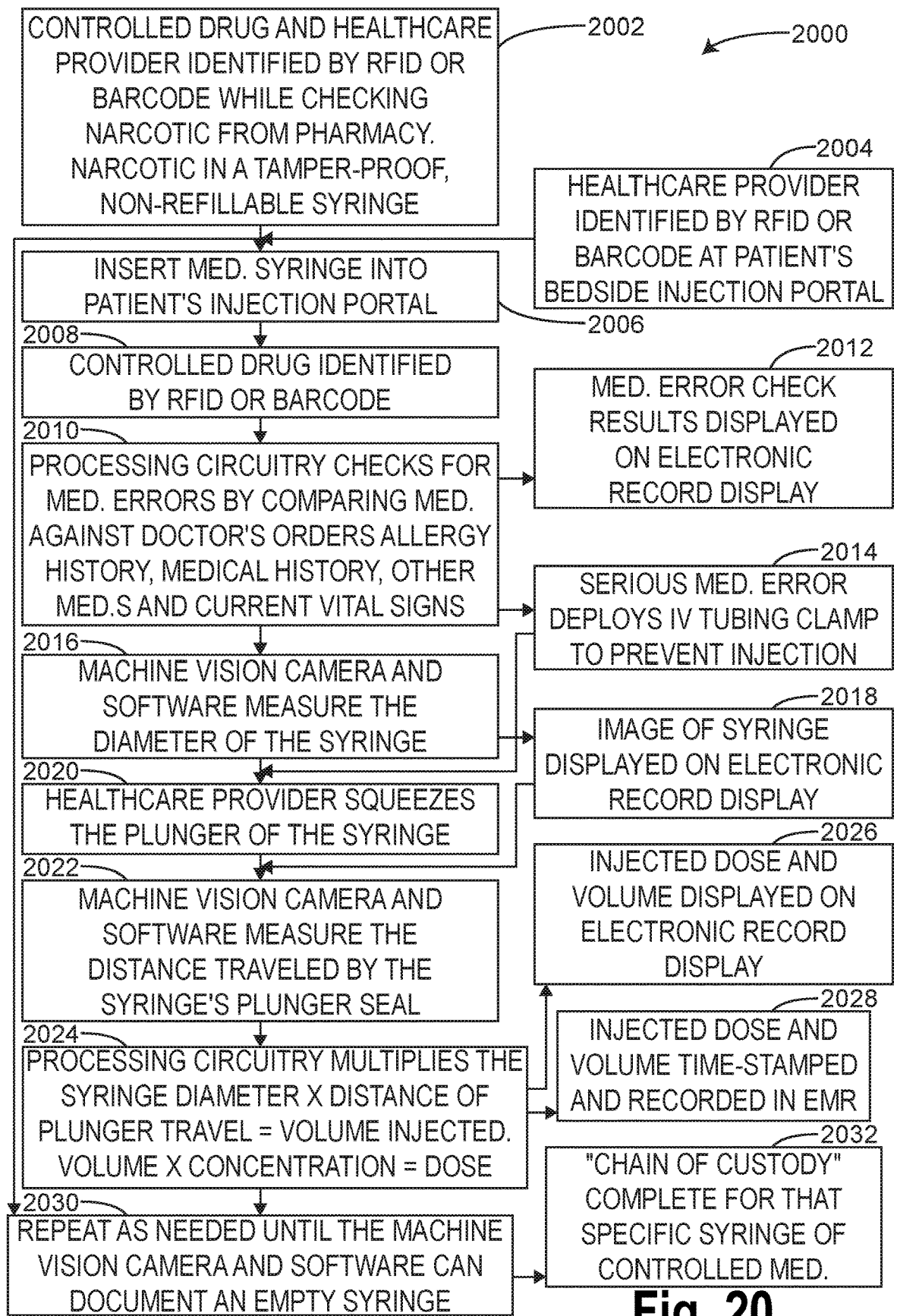
FIG. 20 is a flow chart illustrating a second technique of IV fluid identification and measurement including safety and security aspects, in accordance with at least one example of this disclosure.

FIG. 20 is a flow chart illustrating an example of a second technique of IV fluid identification and measurement including safety and security measures. Aspects of technique 2000 can be similar or the same as techniques 1800 and 1900, however, technique 2000 is particularly well-suited to the challenges of maintaining safety and security with controlled drugs such as narcotics. Technique 2000 can include operation 2002 of identifying a medication (e.g., a controlled drug) and identifying a health care provider, such as by RFID, barcode or QR code reader, retinal scanner, facial recognition, or fingerprint. Operation 2002 can occur at the time a provider checks out a drug from a pharmacy or a medication dispensing machine. The medication can include a narcotic in a tamper-proof, non-refillable syringe.

Operation 2004 can include identifying a provider such as by RFID, barcode or QR code reader, retinal scanner, facial recognition, or fingerprint at a patient's bedside, such as at an injection portal (e.g., 411, FIG. 4). The provider can be the same or a different provider as the provider in operation 2002. In operation 2006, the provider inserts the medication syringe into the patient's injection portal. In operation 2008, the controlled drug is identified, such as by an RFID, barcode or QR code reader associated with the injection portal. Operation 2010 can include processing circuitry checking for medication errors by comparing the medication against doctor's orders, allergy history, medical history, other medications and vital signs. Operation 2012 can include displaying medication error check results on a display, such as display 226, FIG. 2. If the medication error is of a serious nature, the error can cause IV tubing clamps to prevent injection in operation 2014. Operation 2016 can include machine vision camera and software measuring the diameter of the syringe. Operation 2018 can include an image, or an image representing the syringe being displayed on a display, such as display 226, FIG. 2. Operation 2020 can include a provider squeezing the plunger of the syringe. Operation 2022 can include the machine vision camera and software measuring the distance traveled by the syringe's plunger seal (e.g., 548, FIG. 5). Operation 2024 can include processing circuitry determining the volume of medication injected by multiplying the syringe diameter by the distance of plunger travel or determining the dose of medication injected by multiplying the volume of medication injected by the concentration of the medication. Operation 2026 can include displaying the injected volume or dose on a display, such as display 226, FIG. 2.

Operation 2028 can include saving the injected volume or dose along with a timestamp to the EMR. Operation 2030 includes repeating the operations of technique 2000 as necessary until the machine vision camera and software documents an empty syringe. Operation 2032 includes completing the "chain of custody" for a specific syringe of controlled medication. The operations of technique 2000 can be repeated as necessary for other syringes, thereby completing the "chain of custody" for each syringe.

Figure 21:
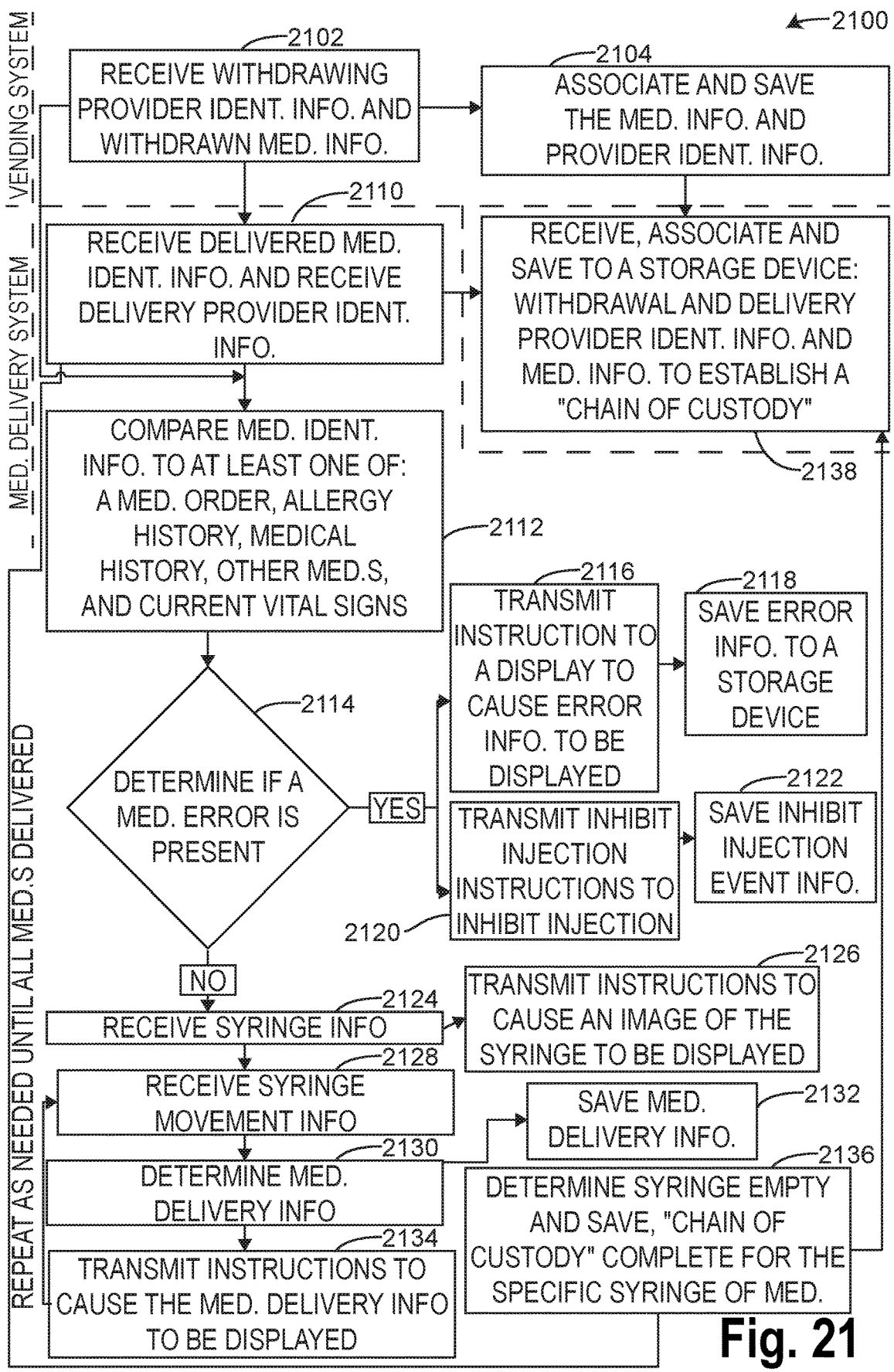
FIG. 21 is a second flow chart illustrating a second technique of IV fluid identification and measurement including safety and security aspects, in accordance with at least one example of this disclosure.
Figure 22:
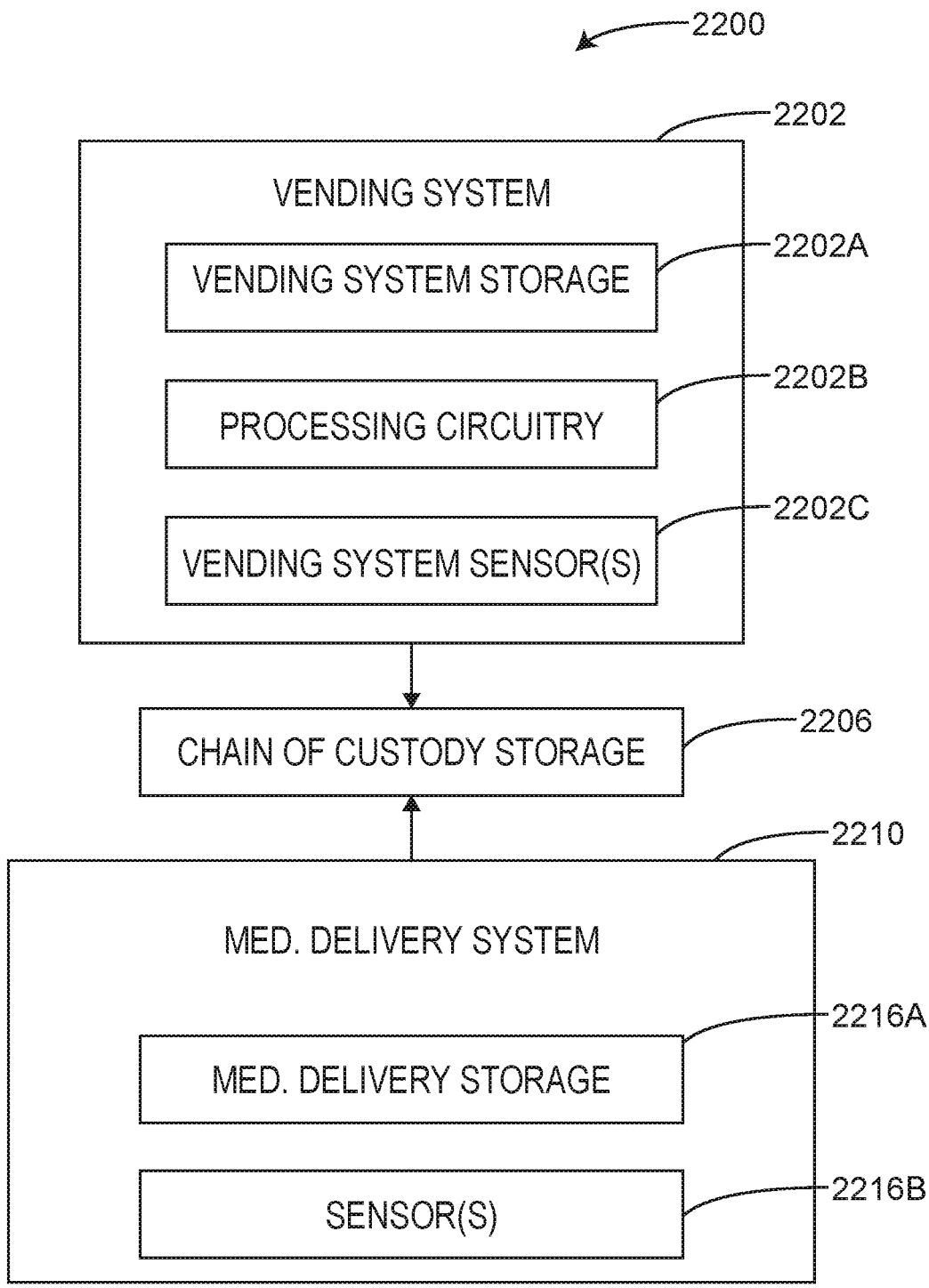
FIG. 22 illustrates generally an example of a block diagram of vending system and a medication delivery system of FIGS. 1-21 upon which any one or more of the techniques (e.g., methodologies) discussed herein may perform in accordance with at least one example of this disclosure.

FIG. 21 is a second flow chart illustrating a technique 2100 including aspects of the technique 2000 of IV fluid identification and measurement including safety and security measures from the perspective of processing circuitry, such as, but not limited to, processing circuitry 157, FIG. 1; 257, FIG. 2; 1502, FIG. 15. The technique may involve processing circuitry 2202B, such as may be part of a medication vending system 2200 as shown in FIG. 22. FIG. 22 illustrates generally an example of a block diagram of vending system and a medication delivery system of FIGS. 1-21 and 23 upon which any one or more of the techniques (e.g., methodologies) discussed herein may perform in accordance with some embodiments. FIGS. 21 and 22 are described together.

In some examples, operations 2102 and 2104 can be part of a vending system (2202, FIG. 22) for managing medication withdrawal from a pharmacy or other vending system. Operations 2110-2136 can be part of a medication delivery system (e.g., can be used with the bedside patient systems and modules shown and describe in FIGS. 1-15; medication delivery system 2210, FIG. 22). Operation 2138 can tie information, including data generated by the vending system 2202 and the medication delivery system 2210 together to facilitate tracking a "chain of custody" for a specific syringe of controlled medication from the pharmacy until the medication is completely injected into the patient. Chain of custody information can be stored to one or more of: the vending system storage 2202A, the medication delivery storage 2216A, and chain of custody storage device (e.g., 2206, FIG. 22) and the EMR. Any of the storage described herein can include one or more storage devices or memory as described herein and can include other storage devices in electrical communication with the vending system or the medication delivery system.

Operation 2102 of the vending system can include receiving withdrawing provider identification information from a medication dispensing sensor 2202C, such as a first RFID or barcode reader that reads a badge of a provider and reads the medication identification information from a syringe or other medication container, or any other type of suitable sensor described herein. Operation 2104 can include associating and saving the medication identification information and the withdrawing provider identification information to a vending system storage device (e.g., 2202A, FIG. 22).

Operation 2110 can include receiving medication identification information from a first identification sensor (e.g., RFID, QR, barcode reader, or machine vision camera reads information about a medication) and receiving delivery provider identification information from the first identification sensor or another identification sensor (e.g., a second identification sensor, another RFID, QR or barcode reader, machine vision camera, retinal scanner, facial recognition sensor or fingerprint reader). In some examples, patient identification information can also be obtained from one of the first identification sensor, second identification sensor or another identification sensor, such as by scanning patient identification information on a hospital wristband. In some examples receiving the medication identification, the provider identification information or the patient identification can cause the processing circuitry to send an instruction to a display to prompt the user for the other of the medication identification information, the provider identification information or the patient identification information.

Operation 2112 can include comparing the received identification information to one or more of: a medication order, allergy history, medical history, other medications and current vital signs. Operation 2114 can include determining if a medication error is present. If it is determined that a medication error is present, operation 2116 can include transmitting instructions including error information to a display to cause the error information to be displayed. Operation 2118 can include saving the error information to one or more storage devices. Further, if in operation 2114 it is determined that a medication error has occurred, operation 2120 can include transmitting inhibit injection instructions to an actuator such as, but not limited to, an IV tubing clamp (e.g., 1060A, 1060B; FIG. 10) to inhibit injection. Operation 2122 can include saving an inhibit injection event information to one or more storage devices.

Operation 2124 can include receiving syringe information from a second medication sensor (e.g., syringe diameter including syringe inner diameter, outer diameter, or wall thickness from a machine vision camera). Operation 2124 can include receiving syringe size information from a data storage device, the syringe size information provided by the syringe manufacturer that supplies the specific syringes used by the specific healthcare facility. Operation 2126 can include transmitting instructions to a display to cause an image of the syringe or a representation of the syringe to be displayed. Operation 2128 can include receiving syringe movement information from the second medication sensor or another sensor. Syringe movement information can include, for example, a distance of travel of the syringe plunger relative to the syringe barrel.

Operation 2130 can include determining medication delivery information based on the syringe movement information. Medication delivery information can include, for example, a volume or dose of medication delivered to the patient (e.g., ejected from the syringe). In some examples, the volume of medication delivered (e.g., ejected from the syringe) can be calculated by multiplying the syringe inner diameter by the distance of plunger travel. Likewise, the dose of medication delivered can be calculated by multiplying the calculated volume by a concentration of the medication. Operation 2132 can include saving medication delivery information to one or more storage devices. In other words, operation 2132 can include documenting volume, dose and time in an EMR, in some cases automatically without intervention from a provider.

Operation 2134 can include transmitting instructions to one or more displays described herein to cause the medication delivery information to be displayed. Operation 2136 can include determining that a syringe is empty and saving "chain of custody" complete for the specific syringe of medication (e.g., controlled drug) to one or more storage devices.

To complete and document the chain of custody, thereby ensuring the medication was delivered to the patient, operation 2138 can include one or more of receiving, associating and saving to one or more chain of custody storage devices (e.g., 2206, FIG. 22), information from both the pharmacy vending system 2202 (FIG. 22) and the bedside medication delivery system 2210 (FIG. 22)(e.g., 1516; FIG. 15). In some examples the one or more chain of custody storage devices or sensors is not necessarily separate from the vending system storage 2202A or the medication delivery storage 2216A or sensors 2216B, but rather can reside with one or the other systems, a different system, multiple systems or can be included as a single storage device.

Figure 23:
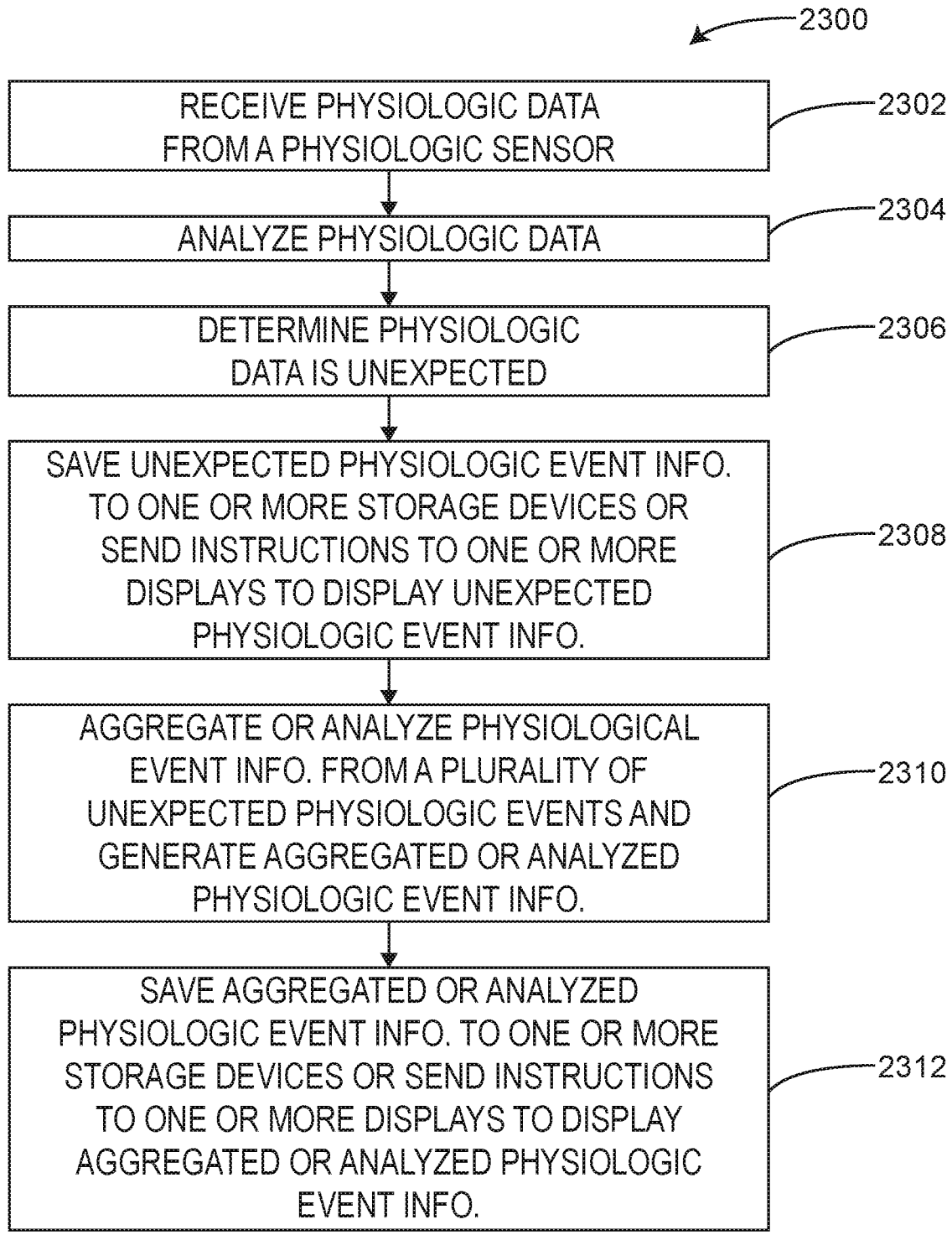
FIG. 23 is a flow chart illustrating a technique 2300 for assessing physiologic events, in accordance with at least one example of this disclosure.

FIG. 23 illustrates and example technique 2300 for assessing physiological events. In some examples, the EMRs created by the automated dose-response record system 100, 200, 400, 600, 800 can provide the most accurate and temporally correlated information about the relationship between any injected medication and the resulting physiologic response. In some examples, this is uniquely accurate dose-response data can be used as a final check of the chain of custody for controlled medications or any medication. The processing circuitry 157, 257 may include or be in electrical communication with artificial intelligence (AI) and/or machine learning that can compare the measured physiologic response in the several minutes after a medication is injected, to the expected physiologic response for that dose of that medication. For example, if the injected medication was a narcotic, it would be expected that the heart rate and blood pressure of the patient would decrease quickly after the injection.

In some examples, if the expected physiologic response does not occur, the AI software of the automated dose-response record system 100, 200, 400, 600, 800 may electronically "flag" that injection as suspicious. For example, if there is no physiologic response after injecting what was supposed to be a narcotic, it is possible that the drug had been stolen and replaced by saline. On the other hand, no response may simply mean that the patient is addicted to and tolerant of narcotics and that too is worth noting. An unpredicted response does not prove anything but multiple unpredicted responses in multiple patients can be suspicious. Therefore, aggregating or analyzing data over time for a particular patient or provider can alert management to issues. If any individual provider traverses a threshold number of flags (e.g., too many "flags") for unexpected physiologic responses (including no response), the automated dose-response record system 100, 200, 400, 600, 800 can generate an alert to notify management and an investigation of that provider may be warranted. Knowing that AI is "watching" the patients' response to a healthcare providers' injected medications, can be a significant deterrent to tempted drug thieves.

Technique 2300 can include determining if one or more unexpected physiological events has occurred, analyzing saving, aggregating and displaying such information, in any order. The method can be performed by processing circuitry 157, 257, 1502, including other processing circuitry, memories and databases in electrical communication with processing circuitry 157, 257, 1502 to one or more of: receive physiologic data, analyze physiologic data, determine physiologic data is unexpected, create and send instructions to cause an alert to the provider or another user, or save a physiological event information (e.g., data) to a storage device 1516 which may include a database. The physiological event information can include, but not limited to data generated by the various sensors and equipment described herein, including one more of: physiological information, patient information, provider information, medication information, time information, location information, facility information, equipment information, aggregated physiological event information and analyzed physiologic event information.

Operation 2302 can include receiving physiologic data from a physiologic sensor, Operation 2304 can include analyzing the physiologic data. Operation 2304 can include comparing the physiologic data to expected physiologic responses, such as the expected response based on the dose. Based on the outcome of the analysis in operation 2304, in operation 2306, the processing circuitry can determine if the physiologic data is unexpected, and if so, operation 2308 can include saving unexpected physiologic event information to one or more storage devices, or can include sending instructions to one or more displays to display unexpected physiologic event information.

Operation 2310 can include aggregating or analyzing physiologic event information from a plurality of unexpected physiological events and generating aggregated or analyzed physiologic event information. In some examples, aggregating can include aggregating a number of physiological events by counting the number of physiological events for a given provider, patient, group of patients, medical facility, type of medication, or any other suitable assessment. Operation 2312 can include saving aggregated or analyzed physiologic event information to one or more storage devices or sending instructions to one or more displays to display aggregated or analyzed physiologic event information. In some examples, the physiologic event information can include any type of physiologic event that occurs, including expected or desirable physiologic events.

The operations of technique 2300 can help provide safer care for patients, including providing narcotic medications when helpful, while keeping a close eye on drug abuse by providers or patients. Taken at a high level, technique 2300 can help medical facilities evaluate which medications are most often abused by patients or stolen by providers, and to mitigate risk for insurers.

Any operations of the various methods described herein can be used in combination with or separately from one another, depending on the desired features and in consideration of constraints such as financial, space, material and manufacturing availability.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including"

and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. The terms approximately, about or substantially are defined herein as being within 10% of the stated value or arrangement.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

NOTES AND VARIOUS EXAMPLES

Each of these non-limiting examples may stand on its own, or may be combined in various permutations or combinations with one or more of the other examples. The examples are supported by the preceding written description as well as the drawings of this disclosure.

Example Set A

Example 1 is an automated dose-response record system including a module for housing waste-heat producing electronic and electromechanical medical equipment including at least one physiologic monitor, and including a system to measure and record administration of one or more IV medications or fluids for IV administration via one or more of a syringe or IV tubing, the automated dose-response record system comprising: a housing configured to house the waste heat-producing electronic and electromechanical medical equipment; a cowling that substantially confines waste heat generated by the waste heat-producing electronic and electromechanical medical equipment; a barcode reader or an RFID interrogator configured to identify at least one of the one or more IV medications or fluids; processing circuitry in electrical communication with the barcode reader or an RFID interrogator and the at least one physiologic monitor; and a machine vision digital camera in electrical communication with the processing circuitry configured to determine a volume of medication administered from a syringe or fluid administered from an IV bag through an IV drip chamber into an IV tubing based on an image generated by the machine vision digital camera, wherein the processing circuitry is configured to receive dose data generated by the machine vision digital camera and to determine the volume of medication administered from a syringe or fluid administered from an IV bag through an IV drip chamber into an IV tubing constituting a dose event, wherein the processing circuitry is configured to receive response data generated by the at least one physiologic monitor constituting a response event, and wherein the processing circuitry is configured to temporally correlate the dose event and the response event and automatically save the temporally-correlated dose-response event to an electronic record or database.

In Example 2, the subject matter of Example 1 includes, an injection portal including an injection port that is configured to be in fluid communication with the IV tubing; and one or more orienting members configured to guide syringes of varying diameters through the injection portal to mate with the injection port.

In Example 3, the subject matter of Example 2 includes, wherein the system to measure and record the administration of the one or more IV medications or fluids further comprises: a display in electrical communication with the machine vision digital camera, wherein the machine vision digital camera is configured to capture an image of a syringe when the syringe is inserted inside the injection portal, and wherein the display is configured to output a visual image or representation of the syringe.

In Example 4, the subject matter of Examples 2-3 includes, wherein the machine vision digital camera is located to capture an image of an inside of the injection portal, and wherein the processing circuitry is configured to interpret the image of a syringe when the syringe is inserted into the injection portal to measure the volume of medication injected from the syringe by determining a size and an internal diameter of the syringe and measuring a distance a plunger of the syringe moves to calculate an injected volume.

In Example 5, the subject matter of Examples 1-4 includes, expired gases, respiratory rate, hemoglobin/hematocrit, cardiac output, central venous pressure, pulmonary artery pressure, brain activity monitor, sedation monitor, urine output, blood loss, blood electrolytes, blood glucose, blood coagulability, train-of-four relaxation monitor, IV extravasation monitor and body weight or any combination thereof.

In Example 6, the subject matter of Examples 1-5 includes, wherein the processing circuitry includes artificial intelligence or machine learning algorithms that compare the response event to the temporally correlated dose event and provide immediate feedback via a display or alert device.

In Example 7, the subject matter of Examples 1-6 includes, wherein the electronic record or database is configured to be accessed by artificial intelligence or machine learning algorithms to retrieve the temporally correlated dose-response event and compare the temporally correlated dose-response event to other temporally correlated dose-response events across a population of patients and output big data correlation insights to at least one storage device or display.

In Example 8, the subject matter of Examples 1-7 includes, a second machine vision digital camera to capture an image of a patient, wherein the second machine vision digital camera is in electrical communication with the processing circuitry and wherein the processing circuitry is configured to analyze the image of the patient to identify an image change including a change in one or more of: a movement, a secretion a skin color change, or any combination thereof.

In Example 9, the subject matter of Example 8 includes, wherein the response event can include one or more of: the movement, the secretion, the skin color change, or any combination thereof identified by the processing circuitry.

In Example 10, the subject matter of Examples 8-9 includes, wherein one or more of: the image, the movement, the secretion, the skin color change, or any combination thereof are automatically saved to the electronic record or database.

Example 11 is an automated dose-response record system including a module for housing waste-heat producing electronic and electromechanical medical equipment including at least one physiologic monitor, and including a system to measure, temporally correlate and record dose and response events, the automated dose-response record system comprising: a housing configured to house the electronic and electromechanical medical equipment; a cowling that substantially confines waste heat generated by the electronic and electromechanical medical equipment; and processing circuitry in electrical communication with the electronic and electromechanical medical equipment to receive dose digital data; and wherein the dose digital data is automatically delivered to the processing circuitry, constituting a dose event, and wherein the processing circuitry is in electrical communication with the at least one electronic physiologic monitor to receive response digital data constituting a response event, wherein the processing circuitry is configured to temporally correlate the dose event and the response event and automatically save the temporally-correlated dose-response event to an electronic record or database.

In Example 12, the subject matter of Example 11 includes, expired gases, respiratory rate, hemoglobin/hematocrit, cardiac output, central venous pressure, pulmonary artery pressure, brain activity monitor, sedation monitor, urine output, blood loss, blood electrolytes, blood glucose, blood coagulability, train-of-four relaxation monitor, IV extravasation monitor and body weight or any combination thereof.

In Example 13, the subject matter of Examples 11-12 includes, wherein the electronic and electromechanical medical equipment includes one or more of: a manual ventilator, a mechanical ventilator, an anesthesia machine, a pneumoperitoneum insufflator, patient warming devices, medication infusion pumps, fluid infusion pumps, blood and fluid warmers, electrosurgical units, continuous airway pressure device, bed and surgical table tilt controls, sequential compression device controls and pressure off-loading air mattress controls or any combination thereof.

In Example 14, the subject matter of Examples 11-13 includes, wherein the processing circuitry includes artificial intelligence or machine learning algorithms that can compare the response event to the temporally correlated dose event and provide immediate feedback via a display or alert device.

In Example 15, the subject matter of Examples 11-14 includes, wherein the electronic record or database is configured to be accessed by artificial intelligence or machine learning algorithms to retrieve the temporally correlated dose-response event and compare the temporally correlated dose-response event to other temporally correlated dose-response events across a population of patients and output big data correlation insights to at least one storage device or display.

Example 16 is an automated dose-response record system comprising: a housing configured to house waste heat-producing electronic and electromechanical medical equipment including an electronic physiologic monitor; a cowling that substantially confines the waste heat generated by the waste heat-producing electronic and electromechanical medical equipment; a system for monitoring administration of one or more IV medications and fluids, the system comprising: at least one of a sensor configured to identify the one or more IV medications or fluids, or an input configured to receive an identity of the one or more IV medications or fluids; a machine vision digital camera to capture an image of one or more of a syringe or a drip chamber; processing circuitry operably coupled to the sensor to receive an identity of one or more IV medications or fluids, the processing circuitry operably coupled to the machine vision digital camera to receive the captured image and determine a volume of medication administered from a syringe or fluid administered from an IV fluid bag based on the image, wherein the processing circuitry is configured to automatically output the identity and determined volume of medication administered from the syringe or fluid administered from the IV bag to an electronic record or database reflecting dose event data, and wherein the processing circuitry is configured to receive a response event data generated by the electronic physiologic monitor, wherein the dose event data and the response event data are temporally correlated by the processing circuitry and are recorded into an electronic record or database.

In Example 17, the subject matter of Example 16 includes, a system to measure and record the administration of the one or more IV medications or fluids via one or more of a syringe or IV tubing, the system further comprising: an injection portal including an injection port that is configured to be in fluid communication with the IV tubing; and one or more orienting members configured to guide syringes of varying diameters through the injection portal to mate with the injection port.

In Example 18, the subject matter of Examples 16-17 includes, an injection portal including an injection port that is configured to be in fluid communication with IV tubing; and a display in electrical communication with the machine vision digital camera, wherein the machine vision digital camera is configured to capture an image of a syringe when the syringe is inserted inside the injection portal, and wherein the display is configured to output a visual image or representation of the syringe.

In Example 19, the subject matter of Examples 16-18 includes, an injection portal including an injection port that is configured to be in fluid communication with IV tubing; and wherein the machine vision digital camera is located to capture an image of an inside of the injection portal, and wherein the processing circuitry is configured to interpret the image of a syringe when the syringe is inserted into the injection portal to measure the volume of medication injected from the syringe by determining a size and an internal diameter of the syringe and measuring a distance a plunger of the syringe moves to calculate an injected volume.

In Example 20, the subject matter of Examples 16-19 includes, expired gases, respiratory rate, hemoglobin/hematocrit, cardiac output, central venous pressure, pulmonary artery pressure, brain activity monitor, sedation monitor, urine output, blood loss, blood electrolytes, blood glucose, blood coagulability, train-of-four relaxation monitor, IV extravasation monitor and body weight or any combination thereof.

In Example 21, the subject matter of Examples 16-20 includes, wherein the processing circuitry includes artificial intelligence or machine learning algorithms that can compare the response event data to the temporally correlated dose event data and provide immediate feedback via a display or alert device.

In Example 22, the subject matter of Examples 16-21 includes, wherein the electronic record or database is configured to be accessed by artificial intelligence or machine learning algorithms to retrieve the temporally correlated dose-response event data and compare the temporally correlated dose-response event data to other temporally correlated dose-response event data across a population of patients and output big data correlation insights to at least one storage device or display.

In Example 23, the subject matter of Examples 16-22 includes, wherein the system to measure and record the administration of the one or more IV medications or fluids further comprises: a hanger configured to receive the IV bag; an electronic scale in electrical communication with a processor, wherein the hanger is configured to support the IV bag; and a float located in the IV drip chamber, wherein the machine vision digital camera is located adjacent to the IV drip chamber, and wherein the processing circuitry is configured to determine a volume of fluid flowing from the IV bag by determining a size of drops and a number of the drops per unit time to calculate a fluid flow rate, wherein the electronic scale is configured to measure a combined weight of the IV bag, an IV drip chamber, IV tubing and fluid in the IV bag, and wherein the processing circuitry is configured to determine a reduction in the measured combined weight over time to determine a weight of the IV fluids infused over time and convert the measured combined weight over time to at least one of a fluid flow rate or infused fluid volume, wherein at higher flow rates, when the drops in the IV drip chamber coalesce into a fluid stream that is un-interpretable by the machine vision camera and processing circuitry, the fluid stream causes a float in the IV drip chamber to move indicating that fluid is flowing, and wherein when the system fails to identify individual drops and detects that the float is moving, the processing circuitry is configured to measure a fluid flow rate by determining a reduction of the combined weight of the IV bag, the IV drip chamber, the IV tubing and the fluid in the IV bag over time.

Example 24 is an automated dose-response record system comprising: a housing configured to house waste heat-producing electronic and electromechanical medical equipment including an electronic physiologic monitor; a cowling that substantially confines waste heat generated by the waste heat-producing electronic and electromechanical medical equipment; a system for monitoring administration of one or more IV medications and fluids, the system comprising: at least one of a sensor configured to identify the one or more IV medications or fluids, or an input configured to receive an identity of the one or more IV medications or fluids; a machine vision digital camera to capture an image of one or more of a syringe or a drip chamber; processing circuitry operably coupled to the sensor to receive the identity of the one or more IV medications or fluids, the processing circuitry operably coupled to the machine vision digital camera to receive the captured image and determine a volume of medication administered from the syringe or fluid administered from an IV bag based on the image, wherein the processing circuitry automatically outputs the identity and determined volume of medication administered from the syringe or fluid administered from an IV bag to an electronic record or database constituting a dose event; and a machine vision digital camera to capture an image of a patient, wherein the machine vision digital camera is in electrical communication with the processing circuitry, wherein the machine vision camera and the processing circuitry analyzes the image of the patient to identify one or more of a movement, a secretion and a skin color change constituting a response event, and wherein the dose event and the response event are temporally correlated by the processing circuitry and automatically recorded into an electronic record or database.

In Example 25, the subject matter of Example 24 includes, wherein the machine vision camera and processing circuitry are configured to analyze an image of a patient's head during a surgical procedure to identify image changes that include one or more movements including: grimacing, coughing, secreting, lacrimation, sweating, drooling, skin color change, or any combination thereof.

In Example 26, the subject matter of Examples 24-25 includes, wherein the machine vision camera is located to capture the image of the patient in a bed and wherein the processing circuitry is configured to identify image changes that include one or more: movements including restlessness, trying to get out of bed without assistance, coughing, a rocking breathing pattern indicative of an airway obstruction; a secretion including, lacrimation, sweating, drooling; or skin color changes indicative of inadequate oxygen, poor perfusion, hypothermia, or any combination of the movements, secretions or skin color changes thereof.

In Example 27, the subject matter of Examples 24-26 includes, wherein the processing circuitry includes artificial intelligence or machine learning algorithms that compare the response event to the temporally correlated dose event and provide immediate feedback via a display or alert device.

In Example 28, the subject matter of Examples 24-27 includes, wherein the electronic record or database is configured to be accessed by artificial intelligence or machine learning algorithms to retrieve the temporally correlated dose-response event and compare the temporally correlated dose-response event to other temporally correlated dose-response events across a population of patients and output big data correlation insights to at least one storage device or display.

In Example 29, the subject matter of Examples 24-28 includes, wherein the processing circuitry analyzes the image of a head of the patient during surgery to identify therapeutic interventions provided by a healthcare provider including one or more of: mask ventilation, pharyngeal airway placement, endotracheal intubation and extubation, airway suctioning and eye taping, or any combination thereof, and wherein a result of the analysis is entered into the electronic record or database as the dose event.

In Example 30, the subject matter of Examples 24-29 includes, wherein the machine vision processing circuitry analyzes the image of the patient in bed to identify therapeutic interventions from a healthcare provider including one or more of: checking on the patient, repositioning the patient, administering medications, suctioning the patient's airway or any combination thereof, and wherein a result of the analysis is saved to the electronic record or database as the dose event.

Example 31 is at least one machine-readable medium including instructions that, when executed by processing circuitry, cause the processing circuitry to perform operations to implement of any of Examples 1-30.

Example 32 is an apparatus comprising means to implement of any of Examples 1-30

Example 33 is a system to implement of any of Examples 1-30.

Example 34 is a method to implement of any of Examples 1-30.

Example Set B

Example 1 is a dose-response medical system comprising: processing circuitry; and one or more storage devices including a memory, the memory including instructions which when executed on the processing circuitry cause the processing circuitry to perform operations including: receiving dose information and response information from one or more sensors, wherein the dose information includes, data corresponding to a dose provided to a patient, and wherein the response information includes data corresponding to a response of the patient; and temporally correlating the dose information and the response information and saving the temporally correlated dose-response information to at least one of the one or more storage devices.

In Example 2, the subject matter of Example 1 includes, wherein temporally correlating the dose-response information includes continuously temporally correlating the dose-response information.

In Example 3, the subject matter of Examples 1-2 includes, wherein temporally correlating the dose-response information includes temporally correlating the dose-response information in a range between every 0.1 seconds to 15 minutes.

In Example 4, the subject matter of Examples 1-3 includes, aggregating the temporally correlated dose-response information with temporally correlated dose-response information collected from other patients.

In Example 5, the subject matter of Examples 1-4 includes, aggregating the temporally correlated dose-response information with temporally correlated dose-response information collected from the patient over a different period of time.

In Example 6, the subject matter of Examples 1-5 includes, wherein the dose information includes data generated by one or more of: an RFID interrogator, a barcode reader, a QR code reader, a machine vision digital camera, or any combination thereof.

In Example 7, the subject matter of Examples 1-6 includes, wherein the response information includes data generated by a machine vision digital camera.

In Example 8, the subject matter of Examples 1-7 includes, wherein the response information includes an image of the patient and wherein the processing circuitry is configured to image changes that include one or more: movements including restlessness, trying to get out of bed without assistance, coughing, a rocking breathing pattern indicative of an airway obstruction; a secretion including, lacrimation, sweating, drooling; or skin color changes indicative of inadequate oxygen, poor perfusion, hypothermia, or any combination of the movements, secretions or skin color changes thereof.

In Example 9, the subject matter of Examples 1-8 includes, wherein the response information includes an image of one or more of a movement, a secretion or a skin color change, and wherein the processing circuitry is configured to identify changes in the response information.

In Example 10, the subject matter of Examples 1-9 includes, wherein the response information includes physiologic data generated by a physiologic monitor.

In Example 11, the subject matter of Example 10 includes, expired gases, respiratory rate, hemoglobin, hematocrit, cardiac output, central venous pressure, pulmonary artery pressure, brain activity monitor, sedation monitor, urine output, blood loss, blood electrolytes, blood glucose, blood coagulability, train-of-four relaxation monitor data, IV extravasation monitor data and body weight.

In Example 12, the subject matter of Examples 1-11 includes, wherein the processing circuitry includes artificial intelligence or machine learning algorithms that can analyze the temporally correlated dose-response information and output feedback on a display or cause an alert to be activated.

In Example 13, the subject matter of Examples 1-12 includes, wherein the processing circuitry is configured to output to a display at least a portion of the temporally-correlated dose-response information.

In Example 14, the subject matter of Examples 1-13 includes, an analysis system configured to receive the temporally correlated dose-response information and to compare the temporally correlated dose-response information to other temporally correlated dose-response information across a population of patients and to output a correlation or comparison to at least one of the one or more storage devices or a display.

Example 15 is at least one machine-readable medium including instructions that, when executed by processing circuitry, cause the processing circuitry to perform operations to implement of any of Examples 1-14.

Example 16 is an apparatus comprising means to implement any of Examples 1-14.

Example 17 is a system to implement any of Examples 1-14.

Example 18 is a method to implement any of Examples 1-14.

What is claimed is:

1. A module for housing waste-heat producing electronic and electromechanical medical equipment including an automated dose-response record system, at least one physiologic monitor and at least one machine vision camera, the module comprising:
    a housing configured to house waste heat-producing electronic and electromechanical medical equipment;
    a cowling that substantially confines waste heat generated by the waste heat-producing electronic and electromechanical medical equipment; and
    the automated dose-response record system comprising:
    at least one machine vision camera positioned to detect at least one of dose events or response events,
    at least one physiologic monitor to detect response events, and
    processing circuitry in electrical communication with the at least one machine vision camera and the at least one physiologic monitor;
    wherein
    the processing circuitry is configured to receive dose data generated by the machine vision digital camera constituting a dose event,
    the processing circuitry is configured to receive response data generated by the at least one physiologic monitor or machine vision digital camera constituting a response event, and
    the processing circuitry and software is configured to timestamp both the dose event and response event data and automatically store the time-stamped data in memory, an electronic record or database allowing artificial intelligence analysis of the temporally correlated dose event and the response event data.

2. The automated dose-response record system of claim 1, wherein the processing circuitry and software analyze the image of a head of the patient during surgery to identify therapeutic interventions provided by a healthcare provider constituting dose events including one or more of: mask ventilation, pharyngeal airway placement, endotracheal intubation and extubation, and airway suctioning, or any combination thereof, and wherein a result of the analysis is timestamped and entered into the electronic record or database as a dose event.

3. The automated dose-response record system of claim 1, wherein the processing circuitry and software analyze the image of the patient in bed to identify therapeutic interventions from a healthcare provider constituting dose events including one or more of: checking on the patient, repositioning the patient, administering medications, suctioning the patient's airway, feeding the patient or any combination thereof, and wherein a result of the analysis is timestamped and saved to the electronic record or database as a dose event.

4. The automated dose-response record system of claim 1, wherein the machine vision camera, processing circuitry and software are configured to analyze an image of a patient's head during a surgical procedure to identify image changes constituting response events that include one or more of: grimacing, coughing, lacrimation, sweating, skin color change, or any combination thereof, and wherein a result of the analysis is timestamped and entered into the electronic record or database as a response event.

5. The automated dose-response record system of claim 1, wherein
the machine vision camera is located to capture the image of the patient in a bed and wherein the processing circuitry and software is configured to identify image changes constituting response events that include one or more of movements that include at least one of restlessness, trying to get out of bed without assistance, coughing, a rocking breathing pattern indicative of an airway obstruction; a secretion including, lacrimation, sweating, drooling; or skin color changes indicative of inadequate oxygen, poor perfusion, hypothermia, any combination of the movements, and secretions or skin color changes, and
a result of the analysis is timestamped and entered into the electronic record or database as a response event.

6. The automated dose-response record system of claim 1, wherein the electronic physiologic monitor includes or measures one or more of the following response events: electrocardiogram, pulse oximetry, blood pressure, temperature, end-tidal $CO_2$, expired gases, respiratory rate, hemoglobin/hematocrit, cardiac output, central venous pressure, pulmonary artery pressure, brain activity monitor, sedation monitor, urine output, blood loss, blood electrolytes, blood glucose, blood coagulability, train-of-four relaxation monitor, IV extravasation monitor and body weight or any combination thereof, and wherein a result of the analysis is timestamped and entered into the electronic record or database as a response event.

7. The automated dose-response record system of claim 1, wherein the processing circuitry and software include artificial intelligence or machine learning algorithms that can compare the time-stamped response event data to the temporally correlated timestamped dose event data and provide immediate point of care clinical decision support feedback via a display or alert device.

8. The automated dose-response record system of claim 1, wherein the electronic record or database is configured to be accessed by artificial intelligence or machine learning algorithms to retrieve the temporally correlated dose-response event data and compare the temporally correlated dose-response event data to other temporally correlated dose-response event data across a population of patients and output big data correlation insights to at least one storage device or display.

9. The automated dose-response record system of claim 1, wherein the electronic and electromechanical medical equipment includes one or more of: a manual ventilator, a mechanical ventilator, an anesthesia machine, gas flow meters, a pneumoperitoneum insufflator, patient warming devices, medication infusion pumps, fluid infusion pumps, blood and fluid warmers, electrosurgical units, continuous airway pressure device, bed and surgical table tilt controls, sequential compression device controls and pressure off-loading air mattress controls or any combination thereof, and wherein the operational data from the electronic and electromechanical medical equipment is timestamped and entered into the electronic record or database as a dose event.

10. An automated dose-response record system, including a module for housing electronic and electromechanical medical equipment including at least one physiologic monitor and at least one machine vision digital camera, and including a system to measure, timestamp and record dose and response events, the automated dose-response record system comprising:
a housing configured to house electronic and electromechanical medical equipment;
a cable and hose management system located on a patient side of the module, wherein the patient side of the module is configured to face a patient and provide the closest and most direct access to the patient;
at least one machine vision camera positioned to detect at least one of dose events or response events; and
processing circuitry in electrical communication with the electronic and electromechanical medical equipment and machine vision digital camera to receive dose event digital data, the processing circuitry in electrical communication with the at least one electronic physiologic monitor and machine vision digital camera to receive response event digital data,
wherein the processing circuitry and software is configured to timestamp both the dose event and response event data and automatically store the timestamped data in memory, an electronic record or database allowing artificial intelligence analysis of the temporally correlated dose event and a response event data.

11. The automated dose-response record system of claim 10, wherein the processing circuitry and software analyze the image of a head of the patient during surgery to identify therapeutic interventions provided by a healthcare provider constituting dose events including one or more of: mask ventilation, pharyngeal airway placement, endotracheal intubation and extubation, airway suctioning and eye taping, or any combination thereof, and wherein a result of the analysis is timestamped and entered into the electronic record or database as a dose event.

12. The automated dose-response record system of claim 10, wherein the processing circuitry and software analyze the image of the patient in bed to identify therapeutic interventions from a healthcare provider constituting dose events including one or more of: checking on the patient, repositioning the patient, administering medications, suctioning the patient's airway, feeding the patient or any combination thereof, and wherein a result of the analysis is timestamped and saved to the electronic record or database as a dose event.

13. The automated dose-response record system of claim 10, wherein the machine vision camera, processing circuitry and software are configured to analyze an image of a patient's head during a surgical procedure to identify image changes constituting response events that include one or more of: grimacing, coughing, secreting, lacrimation, sweating, skin color change, or any combination thereof, and wherein a result of the analysis is timestamped and entered into the electronic record or database as a response event.

14. The automated dose-response record system of claim 10,
the machine vision camera is located to capture the image of the patient in a bed and wherein the processing circuitry and software is configured to identify image changes constituting response events that include one or more of movements that include at least one of restlessness, trying to get out of bed without assistance, coughing, a rocking breathing pattern indicative of an airway obstruction; a secretion including, lacrimation, sweating, drooling; or skin color changes indicative of inadequate oxygen, poor perfusion, hypothermia, any combination of the movements, and secretions or skin color changes, and
a result of the analysis is timestamped and entered into the electronic record or database as a response event.

15. The automated dose-response record system of claim 10, wherein the electronic physiologic monitor includes or measures one or more of the following response events: electrocardiogram, pulse oximetry, blood pressure, temperature, end-tidal $CO_2$, expired gases, respiratory rate, hemoglobin/hematocrit, cardiac output, central venous pressure, pulmonary artery pressure, brain activity monitor, sedation monitor, urine output, blood loss, blood electrolytes, blood glucose, blood coagulability, train-of-four relaxation monitor, IV extravasation monitor and body weight or any combination thereof, and wherein a result of the analysis is timestamped and entered into the electronic record or database as a response event.

16. The automated dose-response record system of claim 10, wherein the processing circuitry and software include artificial intelligence or machine learning algorithms that can compare the timestamped response event data to the temporally correlated timestamped dose event data and provide immediate point of care clinical decision support feedback via a display or alert device.

17. The automated dose-response record system of claim 10, wherein the electronic record or database is configured to be accessed by artificial intelligence or machine learning algorithms to retrieve the temporally correlated dose-response event data and compare the temporally correlated dose-response event data to other temporally correlated dose-response event data across a population of patients and output big data correlation insights to at least one storage device or display.

18. The automated dose-response record system of claim 10, wherein the electronic and electromechanical medical equipment includes one or more of: a manual ventilator, a mechanical ventilator, an anesthesia machine, gas flow meters, a pneumoperitoneum insufflator, patient warming devices, medication infusion pumps, fluid infusion pumps, blood and fluid warmers, electrosurgical units, continuous airway pressure device, bed and surgical table tilt controls, sequential compression device controls and pressure off-loading air mattress controls or any combination thereof, and wherein the operational data from the electronic and electromechanical medical equipment is timestamped and entered into the electronic record or database as a dose event.

19. An automated dose-response record system that includes at least one physiologic monitor and machine vision digital camera, and includes a system to measure, timestamp and record dose and response events, the automated dose-response record system comprising:
at least one machine vision camera positioned to detect at least one of dose events or response events;
processing circuitry in electrical communication with the machine vision digital camera to receive dose event digital data;
at least one physiologic monitor to detect response events; and
the processing circuitry is also in electrical communication with the at least one electronic physiologic monitor and the machine vision digital camera to receive response event digital data,
wherein the processing circuitry and software is configured to timestamp both the dose event and response event data and automatically store the timestamped data in memory, an electronic record or database allowing artificial intelligence analysis of the temporally correlated dose event and a response event data.

20. The automated dose-response record system of claim 19, wherein the processing circuitry and software analyze the image of a head of the patient during surgery to identify therapeutic interventions provided by a healthcare provider constituting dose events including one or more of: mask ventilation, pharyngeal airway placement, endotracheal intubation and extubation, airway suctioning and eye taping, or any combination thereof, and wherein a result of the analysis is timestamped and entered into the electronic record or database as a dose event.

21. The automated dose-response record system of claim 19, wherein the processing circuitry and software analyze the image of the patient in bed to identify therapeutic interventions from a healthcare provider constituting dose events including one or more of: checking on the patient, repositioning the patient, administering medications, suctioning the patient's airway, feeding the patient or any combination thereof, and wherein a result of the analysis is timestamped and saved to the electronic record or database as a dose event.

22. The automated dose-response record system of claim 19, wherein the machine vision camera, processing circuitry and software are configured to analyze an image of a patient's head during a surgical procedure to identify image changes constituting response events that include one or more of: grimacing, coughing, secreting, lacrimation, sweating, skin color change, or any combination thereof, and wherein a result of the analysis is timestamped and entered into the electronic record or database as a response event.

23. The automated dose-response record system of claim 19, wherein
the machine vision camera is located to capture the image of the patient in a bed and wherein the processing circuitry and software is configured to identify image changes constituting response events that include one or more of movements that include at least one of restlessness, trying to get out of bed without assistance, coughing, a rocking breathing pattern indicative of an airway obstruction; a secretion including, lacrimation, sweating, drooling; or skin color changes indicative of inadequate oxygen, poor perfusion, hypothermia, any combination of the movements, and secretions or skin color changes, and a result of the analysis is timestamped and entered into the electronic record or database as a response event.

24. The automated dose-response record system of claim 19, wherein the electronic physiologic monitor includes or measures one or more of the following response events: electrocardiogram, pulse oximetry, blood pressure, temperature, end-tidal $CO_2$, expired gases, respiratory rate, hemoglobin/hematocrit, cardiac output, central venous pressure, pulmonary artery pressure, brain activity monitor, sedation monitor, urine output, blood loss, blood electrolytes, blood glucose, blood coagulability, train-of-four relaxation monitor, IV extravasation monitor and body weight or any combination thereof, and wherein a result of the analysis is timestamped and entered into the electronic record or database as a response event.

25. The automated dose-response record system of claim 19, wherein the processing circuitry and software include artificial intelligence or machine learning algorithms that can compare the timestamped response event data to the temporally correlated timestamped dose event data and provide immediate point of care clinical decision support feedback via a display or alert device.

26. The automated dose-response record system of claim 25, wherein the processing circuitry and software can report the point of care clinical decision support feedback to a remote display or alert device for remote supervision or consultation.

27. The automated dose-response record system of claim 25, wherein the processing circuitry and software are configured to report the point of care clinical decision support feedback to a central monitoring station that includes the nurses' station.

28. The automated dose-response record system of claim 19, wherein the electronic record or database is configured to be accessed by artificial intelligence or machine learning algorithms to retrieve the temporally correlated dose-response event data and compare the temporally correlated dose-response event data to other temporally correlated dose-response event data across a population of patients and output big data correlation insights to at least one storage device or display.

29. The automated dose-response record system of claim 19, wherein the electronic and electromechanical medical equipment includes one or more of: a manual ventilator, a mechanical ventilator, an anesthesia machine, gas flow meters, a pneumoperitoneum insufflator, patient warming devices, medication infusion pumps, fluid infusion pumps, blood and fluid warmers, electrosurgical units, continuous airway pressure device, bed and surgical table tilt controls, sequential compression device controls and pressure off-loading air mattress controls or any combination thereof, and wherein the operational data from the electronic and electromechanical medical equipment is timestamped and entered into the electronic record or database as a dose event.

30. The automated dose-response record system of claim 19, wherein the machine vision camera is located to capture the image of the patient in a bed and wherein the processing circuitry and software is configured to identify image changes in remote photoplethysmography (rPPG) which relies on the varying absorption of different wavelengths of light caused by blood volume changes and the oxygen saturation of the blood in the small blood vessels beneath the skin to determine blood oxygen saturation.

* * * * *